(12) United States Patent
Hammer et al.

(10) Patent No.: US 11,884,469 B2
(45) Date of Patent: Jan. 30, 2024

(54) PACKAGING SYSTEM

(71) Applicant: Fisher & Paykel Healthcare Limited, Auckland (NZ)

(72) Inventors: Jeroen Hammer, Auckland (NZ); Mark Arvind McLaren, Auckland (NZ); Abby Rebecca Farrow, Auckland (NZ); Jonathan Neil Ritchie, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 16/595,216

(22) Filed: Oct. 7, 2019

(65) Prior Publication Data
US 2020/0108989 A1    Apr. 9, 2020

Related U.S. Application Data

(60) Provisional application No. 62/742,551, filed on Oct. 8, 2018.

(51) Int. Cl.
| | |
|---|---|
| *A61M 16/06* | (2006.01) |
| *B65D 73/00* | (2006.01) |
| *B65D 75/00* | (2006.01) |
| *B65D 77/04* | (2006.01) |
| *B65D 65/46* | (2006.01) |
| *B65D 85/18* | (2006.01) |
| *B65D 25/10* | (2006.01) |

(52) U.S. Cl.
CPC ..... *B65D 73/0085* (2013.01); *A61M 16/0683* (2013.01); *B65D 25/10* (2013.01); *B65D 65/466* (2013.01); *B65D 75/008* (2013.01); *B65D 77/04* (2013.01); *B65D 85/18* (2013.01); *A61M 2209/06* (2013.01); *B65D 2203/02* (2013.01)

(58) Field of Classification Search
CPC .......... A61M 2209/06; A61M 16/0683; B65D 73/0085; B65D 25/10; B65D 75/008; B65D 2203/02; B65D 85/18; B65D 77/04
USPC ................................................. 206/438, 495
See application file for complete search history.

(56) References Cited

U.S. PATENT DOCUMENTS

| | | | | |
|---|---|---|---|---|
| 4,700,833 A * | 10/1987 | Smith | ............... | A61B 17/06138 229/87.5 |
| 5,050,735 A * | 9/1991 | Levy | ...................... | B65D 75/52 600/572 |
| 6,345,716 B1 * | 2/2002 | Chapman | ............... | B65D 75/32 206/458 |
| 8,408,394 B2 * | 4/2013 | Mesika | .................... | A45D 8/36 206/495 |
| 2003/0029737 A1 * | 2/2003 | Alpern | ............. | A61B 17/06133 206/63.3 |
| 2005/0035019 A1 * | 2/2005 | Luo | ...................... | A45C 7/0054 206/477 |

(Continued)

*Primary Examiner* — Steven A. Reynolds
(74) *Attorney, Agent, or Firm* — Knobbe Martens Olson and Bear, LLP

(57) ABSTRACT

A packaging system for a respiratory mask has a first compartment configured to receive at least a first portion of the respiratory mask, and a second compartment configured to receive at least a second portion of the respiratory mask, the first and second compartments being separated by an internal wall including at least respiratory mask retention feature that may be configured to retain at least the respiratory mask to the packaging system.

28 Claims, 30 Drawing Sheets

(56) References Cited

U.S. PATENT DOCUMENTS

2015/0166218 A1\* 6/2015 Banducci ............ G06K 19/005
                                                                         206/471

\* cited by examiner

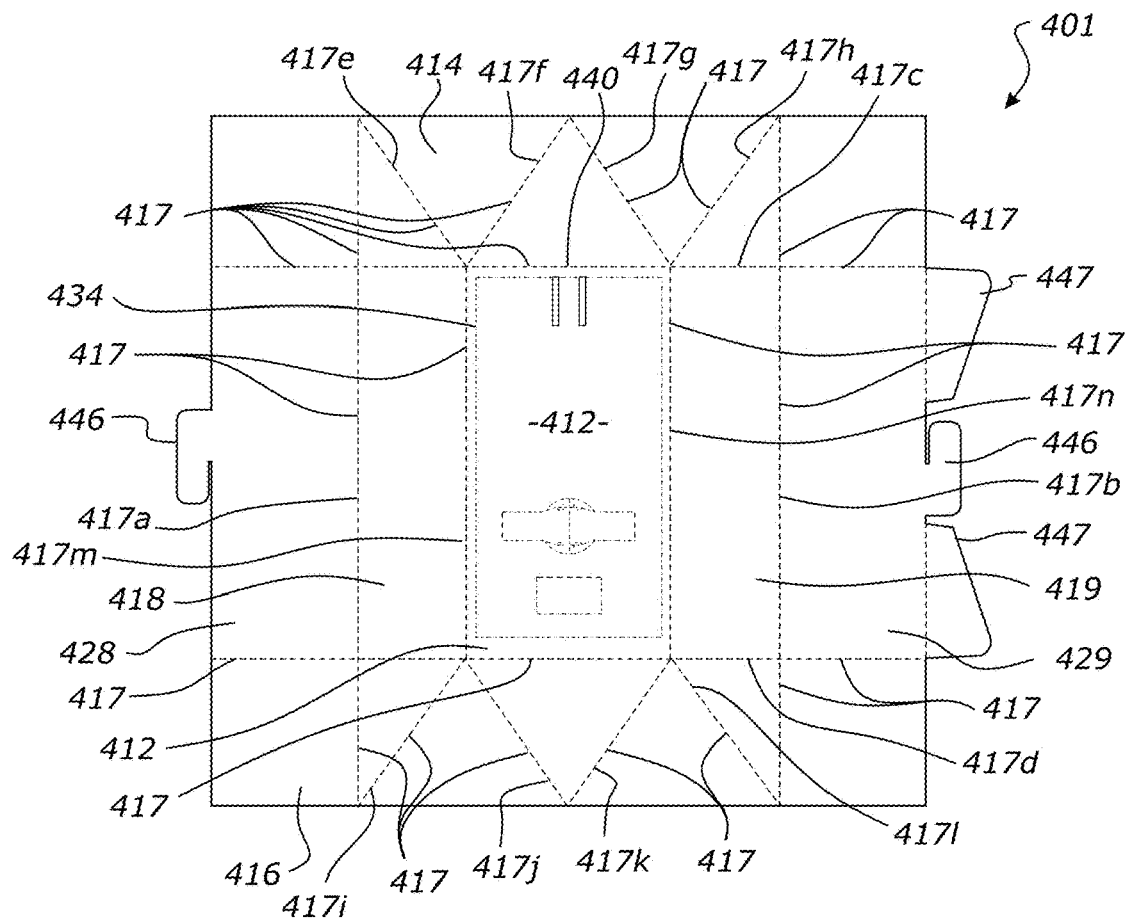
FIGURE. 28
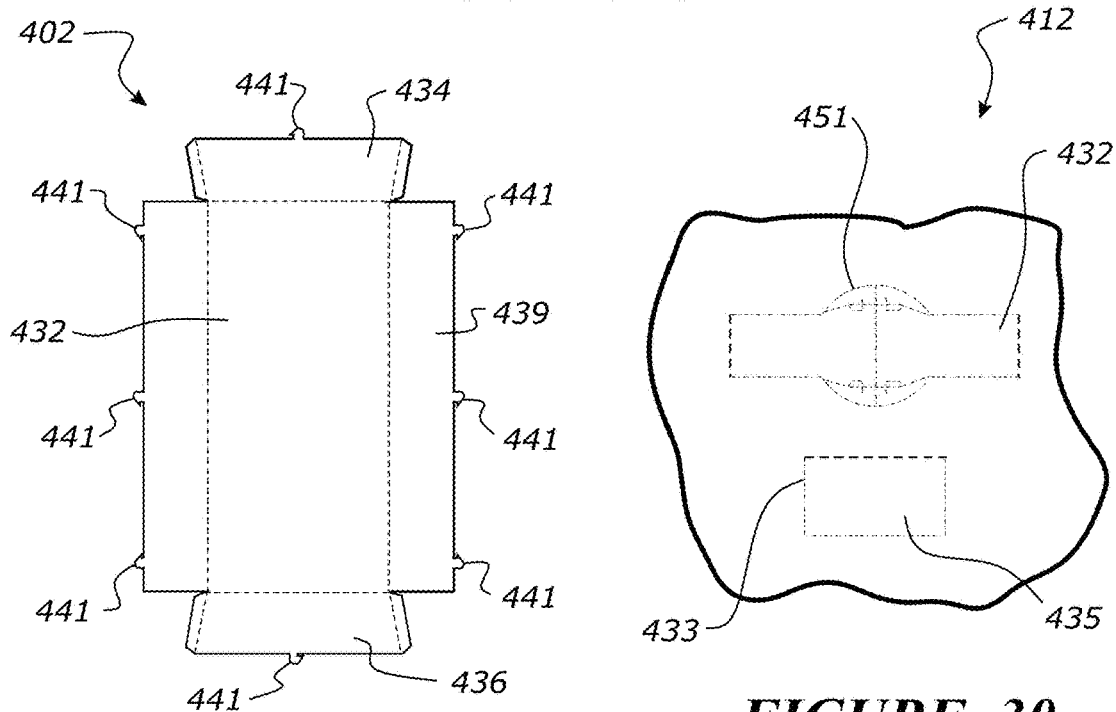
FIGURE. 29
FIGURE. 30

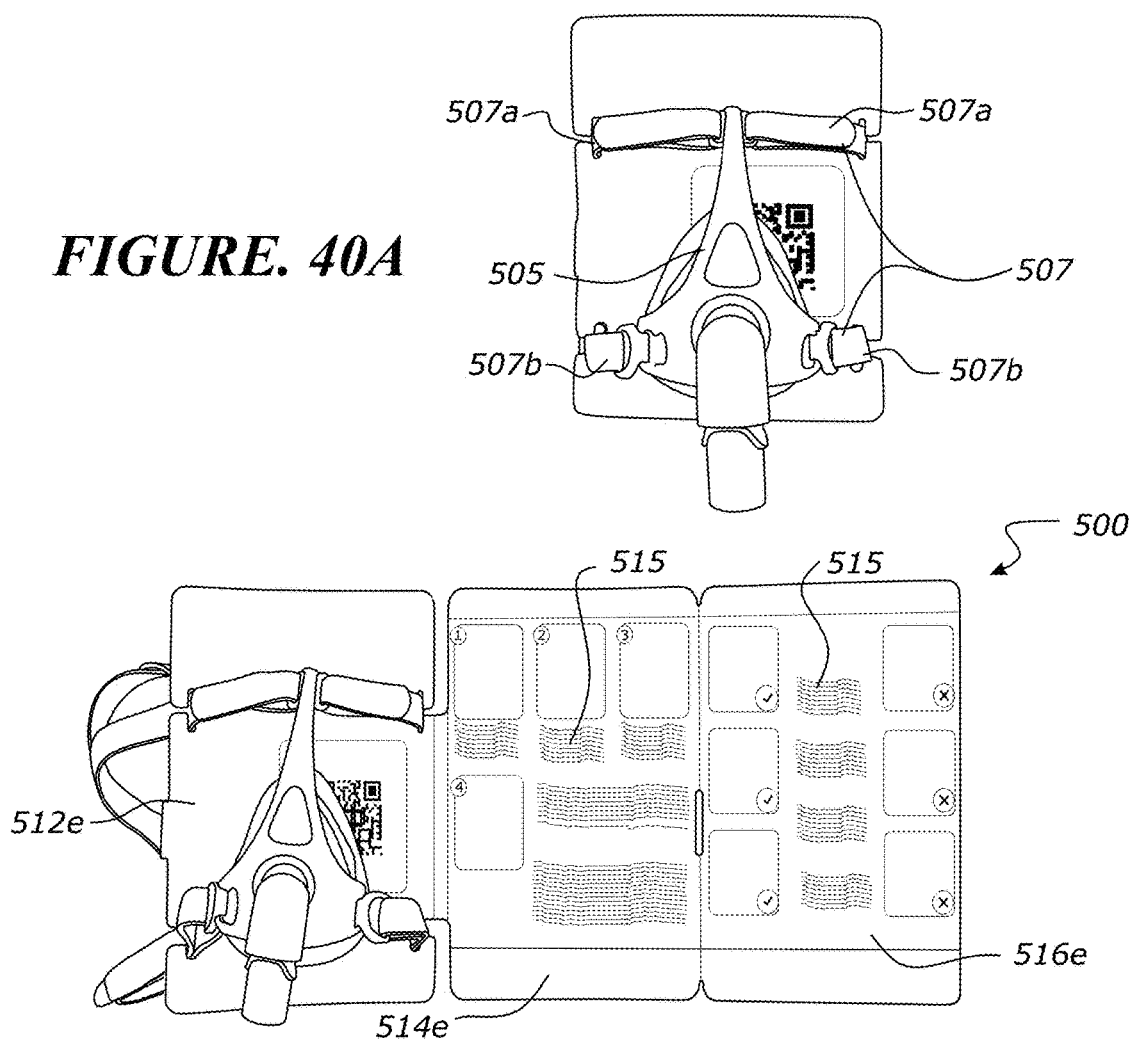
FIGURE. 40A
FIGURE. 40B
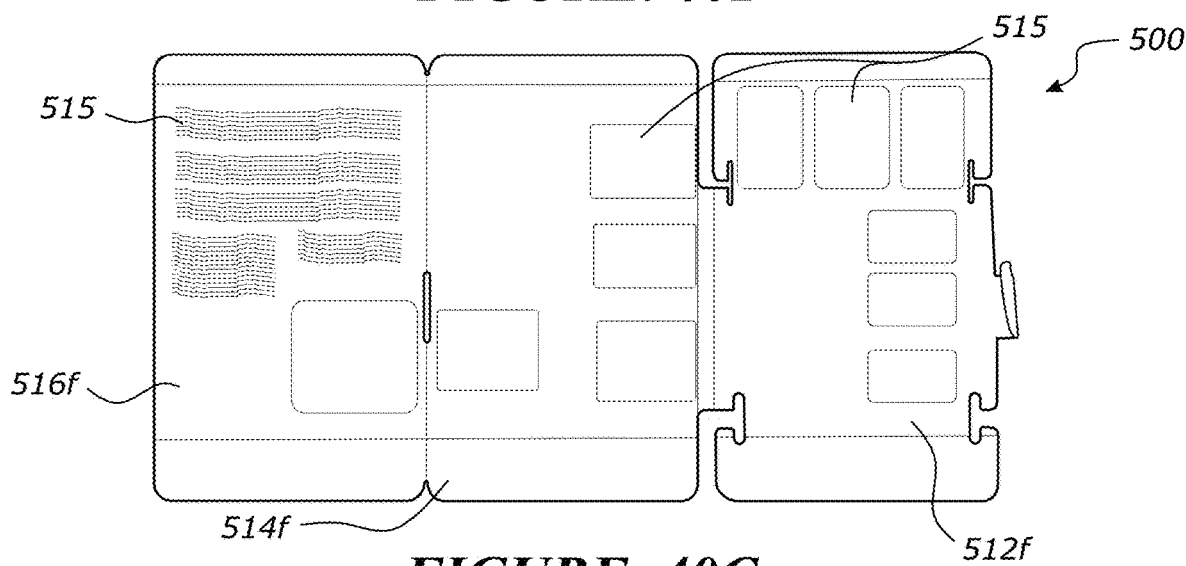
FIGURE. 40C

PACKAGING SYSTEM

FIELD OF THE INVENTION

The present invention relates to a packaging system. More particularly, but not exclusively, the present invention relates to a packaging system for a respiratory mask.

BACKGROUND TO THE INVENTION

Conventional packaging systems present an entire product and its accompanying user instructions to a user at the same time and leave the user free to handle the product and/or read the instructions in their own time and in whatever order they choose, to determine proper use of the product. Where the product is a medical device, such as respiratory mask for use in positive airway pressure (PAP) therapy, continuous positive airway pressure (CPAP) therapy, and/or obstructive sleep apnoea (OSA) therapy, and regardless of whether the user is accustomed to such therapies, this style of packaging may present a steep learning curve with minimal guidance and reassurance that the user is fitting and using the respiratory mask correctly. As a consequence, users may become frustrated, leading to poor treatment compliance.

SUMMARY OF THE INVENTION

Accordingly, in one aspect, the invention broadly resides in a packaging system for a respiratory mask, the packaging system comprising:

a first compartment that is configured to receive at least a first portion of the respiratory mask, and a second compartment that is configured to receive at least a second portion of the respiratory mask, wherein the first and second compartments are at least partially separated by an internal wall and the internal wall includes at least one respiratory mask retention feature that is configured to retain at least the respiratory mask to the packaging system.

In various embodiments, the first compartment is configured to at least partially enclose the respiratory mask.

In various embodiments, the second compartment is configured to retain a user instruction booklet.

In various embodiments, the first portion of the respiratory mask includes at least a respiratory mask frame, a seal, or a conduit connector.

In various embodiments, the second portion of the respiratory mask includes at least a portion of a headgear.

In various embodiments, the first compartment is formed by the internal wall, a pair of opposing side flaps and a top flap extending from the internal wall.

In various embodiments, the side flaps and the top flap are foldable over the internal wall.

In various embodiments, the central panel, opposing side flaps, and the top flap have surfaces provided with the printed information. The surfaces may be internal or external surfaces. Preferably the surfaces are internal surfaces. The printed information may comprise instructional text and/or images.

In various embodiments, the second compartment are formed by at least a central panel and a rear panel.

In various embodiments, the second compartment comprises open sides.

In various embodiments, the second compartment includes rear side flaps configured to fold such that the second compartment is enclosed at the sides.

In various embodiments, the first and second compartments are formed from a single sheet of material.

In various embodiments, the first and second compartments are formed from two different sheets of material.

In various embodiments, the first and second compartments are formed from a cardboard and/or a punched sheet(s) of a cardboard and/or a plastic material.

In various embodiments, the first and second compartments are formed without adhesives or permanent fasteners.

In various embodiments, the carton are configured to be placed in a bag.

In various embodiments, the bag is made from a recyclable, biodegradable and compostable material.

In various embodiments, the internal wall has an aperture or a cut-out that is configured to allow the headgear of the mask to pass through the internal wall.

In another aspect, the invention resides in a packaging system for a respiratory mask, the packaging system comprising:

a carton configured to be retained within the bag and to receive and retain the mask, wherein the carton comprises a first compartment configured to receive a frame and patient interface (such as a cushion module) of the respiratory mask, and a second compartment configured to receive at least part of a headgear of the mask.

In various embodiments, the first and second compartments are at least partially separated by an internal wall and the internal wall includes at least one respiratory mask retention feature that is configured to retain the respiratory mask to the packaging.

In various embodiments, the second compartment is configured to retain a user instruction booklet.

In various embodiments, the first compartment is formed by an internal wall, a pair of opposing side flaps and a top flap extending from the internal wall.

In various embodiments, the side flaps and the top flap is foldable over the internal wall.

In various embodiments, the internal wall, opposing side flaps, and the top flap have surfaces are provided with printed information. The surfaces may be internal or external surfaces. Preferably the surfaces are internal surfaces. Preferably the surfaces are internal surfaces. The printed information may comprise instructional text and/or images.

In various embodiments, the second compartment is formed by at least the internal wall and a rear panel.

In various embodiments, the second compartment comprises open sides.

In various embodiments, the second compartment includes rear side flaps configured to fold such that the second compartment is enclosed at the sides.

In various embodiments, the first and second compartments are formed from a single sheet of material.

In various embodiments, the first and second compartments are formed from two different sheets of material.

In various embodiments, the first and second compartments are made from a cardboard and/or a punched sheet(s) of a cardboard and/or a plastic material.

In various embodiments, first and second compartments are formed without adhesives or permanent fasteners.

In various embodiments, the packaging system comprises a bag, and the carton is retained within the bag.

In another aspect, the invention resides in a packaging carton for a respiratory mask, the packaging carton comprising:

a central panel, having a respiratory mask retaining feature configured to retain a respiratory mask to the central panel; and at least one flap extending from an edge of the central panel, wherein, the at least one flap is configured to be folded towards the central panel and over at least a portion of the respiratory mask in a closed configuration, and to be folded away from the central panel in an open configuration, and the respiratory mask retaining feature is configured to retain the respiratory mask to the central panel when the at least one flap is in either of the open or closed configurations.

In various embodiments, in the closed configuration, the carton is adapted to form a first compartment configured to receive a first portion of the respiratory mask, and a second compartment configured to receive the second portion of the respiratory mask.

In various embodiments, the first compartment is configured to at least partially enclose the respiratory mask, and the second compartment is configured to retain a user instruction booklet.

In various embodiments, the first portion of the respiratory mask includes at least a respiratory mask frame, a seal, or a conduit connector.

In various embodiments, the second portion of the respiratory mask includes at least a portion of a headgear.

In various embodiments, the first compartment is formed by the central panel, a pair of opposing side flaps and a top flap extending from the central panel.

In various embodiments, the side flaps and the top flap are foldable over the central panel.

In various embodiments, the central panel, opposing side flaps, and the top flap have surfaces provided with printed information. The surfaces may be internal or external surfaces. Preferably the surfaces are internal surfaces. Preferably the surfaces are internal surfaces. The printed information may comprise instructional text and/or images.

In various embodiments, the second compartment is formed by at least the central panel and a rear panel.

In various embodiments, the second compartment comprises open sides.

In various embodiments, the second compartment includes rear side flaps configured to fold such that the second compartment is enclosed at the sides.

In various embodiments, the first and second compartments are formed from a single sheet of material.

In various embodiments, the first and second compartments are formed from two different sheets of material.

In various embodiments, the first and second compartments are made from a cardboard and/or a punched sheet(s) of a cardboard and/or a plastic material.

In various embodiments, the first and second compartments are formed without adhesives or permanent fasteners.

In various embodiments, in the closed configuration, the carton is adapted to form a single compartment that is configured to receive at least a portion of the respiratory mask.

In various embodiments, the compartment is configured to at least partially enclose the portion of the respiratory mask.

In various embodiments, the portion of the respiratory mask includes at least a portion of a headgear.

In various embodiments, the at least one flap is foldable over the central panel.

In various embodiments, the central panel and the at least one flap have surfaces provided with printed information. The surfaces are internal or external surfaces or both. Preferably the surfaces are internal surfaces. Preferably the surfaces are internal surfaces. The printed information may comprise instructional text and/or images. The printed information may comprise a machine-readable code such as a Quick Response code (QR code).

In various embodiments, the compartment is formed by at least the central panel and the at least one flap.

In various embodiments, the at least one flap comprises at least two panels, the at least two panels being an intermediate panel and a rear panel, the intermediate panel being located between the central panel and the rear panel and is foldable towards the central panel and the rear panel.

In various embodiments, the compartment comprises at least one open side.

In various embodiments, the carton comprises at least one retention tab that is configured to be received by at least one retention slot.

In various embodiment, the at least one retention tab is located on the central panel and the at least one retention slot is located on the at least one flap.

In various embodiment, the at least one retention tab is located on the at least one flap and the at least one retention slot is located on the central panel.

In various embodiments, the carton is formed from a single sheet of material.

In various embodiments, the carton is made from a cardboard and/or a punched sheet(s) of a cardboard and/or a plastic material.

In various embodiments, the compartment is formed without adhesives or permanent fasteners.

In various embodiments, the central panel and the at least one flap each comprise at least one cut-out that is suitable for securing the respiratory mask inside the compartment.

In various embodiments, the at least one respiratory mask retaining feature comprises a plurality of cutouts configured to receive and frictionally retain straps of the respiratory mask or straps of a headgear of the respiratory mask.

In various embodiments, the respiratory mask retaining feature comprises a headgear retention tab for securing a positioning of the rear panel of a headgear of the respiratory mask.

In various embodiments, the packaging is configured to be placed in a bag.

In various embodiments, the bag is made from a recyclable, biodegradable and/or compostable material.

In another aspect, the invention broadly resides in a carton that is formed of a single sheet material configured to form at least two compartments for use in packaging a respiratory mask, the carton comprising:

a central panel connected to a plurality of flaps configured to be folded over the central panel to form a first compartment and a second compartment.

In various embodiments, the central panel comprises a front surface and a rear surface, a first side, a second side, a third side and a fourth side and the plurality of flaps comprise:

a top flap that is hinged and extends from the first side of the central panel;

a first side flap and a second side flap that are hinged and extend from the third side and the fourth side of the central panel respectively where the third and fourth sides are lateral sides of the central panel and are located opposite to each other.

In various embodiments, the central panel comprises a rear panel that is hinged and extends from the second side of the central panel that is opposite to the first side.

In various embodiments, the first and second side flaps and the top flap are configured to be folded over the front surface to form the first compartment; and the rear panel is configured to be folded over the rear surface to form the second compartment.

In various embodiments, the sheet material is a cardboard.

In various embodiments, the cardboard is a punched sheet of cardboard.

In various embodiments, the sheet material is a plastic.

In various embodiments, the carton comprises fold lines to allow the top flap, the rear panel, the first side flap and the second side flap to be hinged to the respective side of the central panel.

In various embodiments, the first compartment is configured to be partially enclosed or is configured to be open at one edge which is a bottom edge.

In various embodiments, the rear panel comprises at least one rear panel retention feature and the central panel comprises at least one complementary feature that is adapted to engage with the rear panel retention feature thereby allowing the rear panel and the central panel to be fastened together.

In various embodiments, the at least one rear panel retention feature is a rear panel retention tab and the complementary feature is a rear panel retention slot adapted to receive the rear panel retention tab.

In various embodiments, the rear panel retention feature comprises a single hook shaped tab that is set into a lower edge of the rear panel and is configured to engage with a retention slot that is centrally located at or near a top edge of the rear panel.

In various embodiments, the second compartment is configured to provide a partially enclosed space, or is configured to be closed only on top and bottom edges.

In various embodiments, the top flap is configured to fold over the first and second side flaps and comprises top flap retention features, and each of the side flaps comprise at least one complementary feature adapted to engage with at least one of the top flap retention features thereby allowing the top flap and the side flaps to be fastened together.

In various embodiments, the top flap retention features are top flap fastening tabs and the at least one complementary feature on each of the side flaps is a top flap retention slot adapted to receive one of the top flap fastening tabs.

In various embodiments, the top flap retention features are located along an edge of the top flap.

In various embodiments, wherein the item is the respiratory mask having a respiratory mask frame and wherein top flap includes a U-shaped notch or a cut-out.

In various embodiments, the top flap includes a first information panel that is adapted to present a user with an information regarding use of the item.

In various embodiments, the first information panel is located on an external surface of the top flap such that the first information panel is visible when the carton is in closed configuration.

In various embodiments, each of the central panel, side flaps and the top flap provide space for printing information or instructions for the user.

In various embodiments, diagonal fold lines are formed on the first and second side flaps and the top flap.

In various embodiments, two diagonal fold lines are formed on the top flap and one diagonal fold line is formed on each of the first and second side flaps.

In various embodiments, the carton comprises rear side flaps extending from lateral sides of the rear panel to form side walls and thereby enclose the second compartment.

In various embodiments, the carton comprises fold lines allowing rear side flaps to be hinged and extend from lateral sides of the rear panel.

In various embodiments, each of the rear side flaps comprise one or more rear side fastening features adapted to secure the rear flaps in the closed configuration.

In various embodiments, the rear side fastening features comprise tabs adapted to insert into at least one complementary slot formed at the central panel.

In various embodiments, the carton comprises a bottom panel that is hinged and disposed between the central panel and the rear panel.

In various embodiments, the bottom panel is formed by folding the central panel and the rear panel so as to create a flat base such that the carton can stand upright on when place on a flat surface.

In various embodiments, the central panel includes at least one item retention feature configured to retain the respiratory mask.

In various embodiments, the at least one item retention feature is located in a central location of the central panel.

In various embodiments, the at least one item retention feature is a respiratory mask retention feature configured to retain a respiratory mask.

In various embodiments, the respiratory mask retention feature comprises a number of features configured to work together to retain the respiratory mask.

In various embodiments, the respiratory mask retention feature comprises a first aperture or cut-out that allows a headgear of a respiratory mask to pass from the first compartment to the second compartment.

In various embodiments, the aperture comprises a rectangular window that is configured to reveal printed information located in the second compartment.

In various embodiments, the respiratory mask retention feature comprises upper and lower strap slots that are configured to receive and frictionally retain straps of the respiratory mask or straps of a headgear of the respiratory mask.

In various embodiments, the respiratory mask retention feature comprises an inlet component support tab having a second aperture adapted to receive an inlet component of the respiratory mask.

In various embodiments, the inlet component support tab begin either at the same height or below the lower strap slots.

In various embodiments, the inlet component support tab form inner edges of the lower strap slots.

In various embodiments, the lower strap slots are angled to retain the straps of respiratory mask or head gear of the respiratory mask in the assembled state with a respiratory mask frame.

In various embodiments, inlet component support tab comprises a circular head portion and an elongated neck portion extending between the circular head portion and the central panel.

In various embodiments, the first aperture is a rectangular or a substantially rectangular window.

In various embodiments, the respiratory mask retention feature retains a patient interface (such as a cushion module) and a frame on the front surface of the central panel.

In various embodiments, the rear panel includes one or more additional retention features configured to hold at least one item.

In various embodiments, the at least one item is a quick reference guide or a user instruction manual.

In various embodiments, the one or more additional retention features comprise tabs that are configured to overhang edges of the at least one item held on the tabs.

In various embodiments, the respiratory mask retention feature comprise a single upper strap slot configured to receive and frictionally retain straps of the respiratory mask.

In various embodiments the strap slot is configured to receive straps of a headgear of the respiratory mask.

In various embodiments, wherein the carton is configured to remain in a closed configuration without adhesives or permanent fasteners.

In various embodiments, the carton is configured to be placed in a bag.

In various embodiments, the bag is made from a recyclable, biodegradable and/or compostable material.

In various embodiments, the carton is a packaging system or part of the packaging system.

In another aspect, the invention broadly resides in a carton having at least two compartments for use in packaging a respiratory mask, the carton comprising:

a first compartment sheet adapted to form a first compartment; and a second compartment sheet adapted to form a second compartment; wherein the first compartment sheet and second compartment sheet each comprises at least one fastener configured to engage with each other to fasten the first and second compartments together in use.

In various embodiments, the first compartment sheet comprises a central panel that is adapted to form a rear wall to the first compartment, the central panel having a first lateral side and a second lateral side that is located opposite to each other.

In various embodiments, the first compartment sheet comprises a first side panel extending from the first lateral side of the central panel, and a second side panel extending from the second lateral side of the central panel.

In various embodiments, the first compartment sheet comprises a first front flap extending from a lateral side of the first side panel and a second front flap extending from a lateral side of the second side panel.

In various embodiments, the first compartment sheet comprises a collapsible top and bottom flaps configured to fold to enclose a top portion and a bottom portion of the first compartment.

In various embodiments, the second compartment sheet comprises a rear panel configured to form a rear wall, the rear panel having a first lateral side and a second lateral side located opposite to each other.

In various embodiments, the second compartment sheet comprises a first side flap extending from the first lateral side of the rear panel and a second side flap extending from the second lateral side of the rear panel.

In various embodiments, the second compartment sheet comprises a top flap extending from a top of the rear panel and a bottom flap located opposite to the top flap and extending from the bottom of the rear panel.

In various embodiments, the fastener of the first compartment sheet comprises a plurality of fastener slots spaced around an edge of the central panel.

In various embodiments, the fastener of the second compartment sheet comprises a plurality of fastener tabs spaced around the perimeter of the second compartment sheet.

In various embodiments, the plurality of fastener tabs of the second compartment sheet are configured to engage with the plurality of fastener slots on the first compartment sheet to fasten the first and second compartments together during use.

In various embodiments, the plurality of fastener slots are configured to engage with the plurality of fastener tabs with a friction fit.

In various embodiments, the carton is configured to remain in a closed configuration without adhesives or permanent fasteners.

In various embodiments, the carton is configured to be placed in a bag.

In various embodiments, the bag is made from a recyclable, biodegradable and/or compostable material.

In various embodiments, the first and second compartment sheets are each made from a cardboard.

In various embodiments, the first and second compartment sheets are each made out of a punched sheet of a cardboard.

In various embodiments, the first and second compartment sheets are each made out of a plastic.

In various embodiments, the central panel includes at least one item retention feature configured to retain the respiratory mask.

In various embodiments, the at least one item retention feature comprises a plurality of features configured to retain the respiratory mask.

In various embodiments, the at least one item retention feature is located in a central location of the central panel.

In various embodiments, the respiratory mask retention feature comprises an aperture or cut-out through which an elbow or an inlet tube of a respiratory mask can pass, and arms configured to be bent away from the central panel to engage with a lower headgear of a respiratory mask frame.

In various embodiments, the frame and the seal of a respiratory mask is configured to be fully enclosed within the front/first compartment with the seal facing the front.

In various embodiments, headgear straps of the respiratory mask is configured to be attached to the frame at one location.

In various embodiments, the seal of the respiratory mask is presented towards a user so that the seal is presented towards the user so that the seal is the first part of the respiratory mask that is visible to the user when opening the carton.

In various embodiments, the central panel includes a removable panel region configured to be removed to detach the mask from the carton.

In various embodiments, the removable panel includes the respiratory mask retention feature.

In various embodiments, the central panel includes a removable panel region configured to be removed to detach the respiratory mask from the carton.

In various embodiments, the removable panel includes the mask retention feature.

In various embodiments, the central panel comprises a perforated feature or a perforated line that defines the removable panel and enables the removable panel to be removed from the central panel.

In various embodiments, the removable panel comprises a finger grip region to provide a means for gripping the removable panel.

In various embodiments, the first and second front flaps include interlocking means such as fastener tabs adapted to interlock and secure the front/first compartment in a closed configuration.

In various embodiments, the interlocking means comprises closure tabs extending from an edge of one of the front flaps that are configured to be overlapped by the other front flap when in the closed configuration.

In various embodiments, the rear wall of the carton is formed by the rear panel includes information. The information may be at least one of a manufacturing, traceability and legal information.

In various embodiments, the carton is a packaging system or part of the packaging system.

In another aspect, the invention broadly resides in a carton formed of a sheet material that is configured to be folded to retain and at least partially enclose a respiratory mask, wherein the carton is adapted to fold to form a first compartment and a second compartment, wherein the first and second compartments are configured to contain at least a portion of the respiratory mask wherein the first compartment is configured to be opened first to reveal at least the portion of the respiratory mask and present information in stages; and wherein the second compartment is configured to be accessible from both the first compartment and the sides.

In various embodiments, the first compartment is configured to contain a respiratory mask and the second compartment is configured to contain head gear, quick reference guide and/or user instructions guide.

In various embodiments, the carton is the one as described in any one of the statements above.

In another aspect, the invention broadly resides in a carton that comprise two sheets of material that are folded to enclose and retain at least a respiratory mask, the carton comprising:

a first compartment and a second compartment, each of which are adapted to contain at least part of the respiratory mask, wherein the first compartment is configured to be opened first to reveal at least part of the respiratory mask and present information relating to the respiratory mask in stages; and a second compartment that is configured to be accessible from within the first compartment.

In various embodiments, the two sheets of material that are made from one cardboard, punched sheets of cardboard or plastic.

In various embodiments, the carton is pentagonal in shape when assembled and viewed from at least one direction.

In various embodiments, the second compartment is trapezoidal when assembled and viewed from at least one direction.

In various embodiments, the first compartment is configured to contain a respiratory mask and the second compartment is configured to contain a head gear, quick reference guide and user instructions.

In another aspect, the invention resides in a method of using a packaging system, the method further comprises at least the following steps:

revealing or exposing respiratory mask packaged inside or by the packaging or packaging system in sequential steps or stages;

revealing or exposing instructions presented in the packaging system in sequential steps or stages; and concealing information or at least part of the information until a particular or appropriate step or stage has been reached.

In various embodiments, the packaging system is the one as described in any one of the statements above relating to any one of the above-mentioned aspects.

In various embodiments, the packaging system comprises a carton as described in any one of the statements above relating to any one of the above-mentioned aspects.

In another aspect, the invention resides in a method of packaging respiratory mask in a packaging system comprising a carton having a central panel comprising at least one retention feature and a plurality of flaps, the method comprising at least the following steps:

providing the carton, retaining the respiratory mask in the retention feature, folding the plurality of flaps over the central panel to form a first compartment that encloses a first portion of the item or item assembly, and a second compartment that encloses a second portion of the respiratory mask, wherein the first and second compartments are separated by an internal wall formed by the central panel.

In various embodiments, the method comprises creating a respiratory mask retaining feature on the central panel, the respiratory mask retaining feature being configured to retain the respiratory mask.

In another aspect, the invention broadly resides in a bag for use in packaging, the plastic bag comprising:

an opening at a top portion, a foldable base at a bottom portion opposite the opening configured to enable the bag to stand up on a surface, at least a front wall extending from the base to the opening and a rear wall extending from the base to the opening;

the base, the front wall and the rear wall defining an enclosure;

a transparent region at both the front and rear walls at or near the top portion with the remaining portions of the front and rear walls being opaque;

the opaque portion of the front wall comprising a transparent viewing window that is configured to allow at least a part of an item stored inside the bag to be visible from outside.

In various embodiments, the bag is made from a recyclable, biodegradable and/or compostable material.

In various embodiments, the bag comprises minimal information on it other than regulatory, manufacturing or legal information and possibly generic branding information.

In various embodiments, the opening comprises a zip lock.

In various embodiments, the bag is adapted to be used as a part of a packaging system or to be used to package a carton.

In various embodiments, the transparent region extends in each of the first and second walls laterally between two opposite sides of the bag and longitudinally from top portion of the bag up to a point that is between quarter to half of the total length of the bag.

In various embodiments, the transparent viewing window extend orthogonally from the transparent region in a direction that is towards the bottom of the bag.

In various embodiments, the transparent viewing window extend orthogonally from the transparent region in a direction that is towards the bottom of the bag and extends to a point that is proximal to the bottom portion of the bag.

In various embodiments, the transparent viewing window is narrower that the transparent region.

In various embodiments, the bag is used for packaging a carton, the carton being the one as defined in any one of the above-mentioned aspects.

In another aspect, the invention broadly resides in a packaging system for a respiratory mask, the packaging system comprising a first compartment that retains or is configured to retain at least a first portion of the respiratory mask, and a second compartment that retains or is configured to retain at least a second portion of the respiratory mask, wherein the first and second compartments are at least partially be separated by an internal wall and the internal wall include at least one respiratory mask retention feature that retains or is configured to retain at least the respiratory mask to the packaging.

In various embodiments, the packaging system comprises the carton as defined in any one of the above-mentioned aspects.

In various embodiments, the packaging system is the packaging system as defined in any one of the above-mentioned aspects.

In another aspect, the invention broadly resides in a method of using a packaging system that is configured to retain a respiratory mask, the packaging system being configured to provide information to the user in a sequential order pre-determined by a manufacturer/supplier of the respiratory mask, the method comprises at least the following steps:

providing the packaging system in a closed configuration in which the respiratory mask is retained within the packaging system and wherein a first portion of the packaging system at least partly conceals a first portion of the respiratory mask and at least partly conceals a first portion of information that is printed or retained in the packaging system, and wherein a second portion of the packaging system at least partly conceals a second portion of the respiratory mask and at least partly conceals a second portion of information that is printed or retained in the packaging system; and opening the packaging system from the closed configuration to an open configuration in a defined sequence such that the first portion and the second portion of the respiratory mask and the first portion and the second portion of the printed or retained information are sequentially revealed;

wherein at least the second portion of the respiratory mask and the second portion of information remain concealed after the first portion of the respiratory mask and the first portion of information have been revealed.

In various embodiments, the packaging system is the packaging system as defined in any one of the above-mentioned aspects.

In various embodiments, the packaging system comprises the carton as defined in any one of the above-mentioned aspects.

In another aspect, the invention broadly resides in respiratory mask packaging carton that is formed of a single sheet material configured to form at least one compartment for use in packaging a respiratory mask, the carton comprising a main panel that is connected to at least one flap that is configured to be folded over the main panel to form the at least one compartment, the main panel comprising at least one respiratory mask retaining feature that is configured to retain the respiratory mask to the main panel.

In various embodiments, the carton comprises at least three foldable panels, including the main panel, each of the panels having a front surface and a rear surface.

In various embodiments, the main panel is configured to retain the mask and folded over an adjacent panel that is an intermediate panel form a compartment that is adapted to contain at least a portion of headgear of the mask.

In various embodiments, at least one of the surfaces of the at least three panels contain printed information or instructions for the user.

In various embodiments, the carton comprises a retention tab and a retention slot, wherein the retention tab is configured to be opened or released from the retention slot to reveal inner surfaces of the panel to present printed information in stages.

In various embodiments, the at least one compartment is formed by the main panel folding in a direction towards an intermediate panel that is located adjacent the main panel and between the main panel and a rear panel, and by inserting the retention tab that is connected to the main panel into the retention slot located at or near a fold line formed between the intermediate panel and the rear panel.

In various embodiments, the retention tab is adapted to prevent the carton from unfolding thereby maintaining the at least one compartment for headgear straps of the mask to be retained.

In various embodiments, the at least one mask retaining n feature comprises a plurality of slots or cut-outs that can are configured to receive and frictionally retain the straps of headgear of the mask.

In various embodiments, the plurality of slots or cut-outs comprises two upper cut-outs and two lower cut-outs.

In various embodiments, one of the at least three panels is foldable or unfoldable without the need to remove the retention tab.

In various embodiments, the compartment is partially enclosed and can be opened along a top and a bottom edge of the carton.

In various embodiments, the mask is configured to be secured onto the main panel by feeding headgear straps behind the main panel into the compartment through the mask retaining feature that is in the form of a plurality of cutouts or slots located at the main panel.

In various embodiments, the carton comprises at least two foldable panels each having a front surface and a rear surface.

In various embodiments, the main panel is configured to retain the mask and folded over an adjacent panel that is a front panel to form a compartment that is adapted to contain at least a portion of headgear of the mask.

In various embodiments, at least one of the surfaces of the at least two panels contain printed information or instructions for the user.

In various embodiments, at least one of the surfaces of the at least two panels contain printed information or instructions for the user.

In various embodiments, the carton comprises at least two retention tabs and at least two retention slots, wherein the retention tabs are configured to be opened/released from the retention slots to reveal inner surfaces of the panels to present printed information in stages.

In various embodiments, the at least one compartment is formed by folding the front panel that is located adjacent the main panel in a direction towards the main panel, and by inserting the retention tabs that are located at the front panel into the retention slots located at the main panel.

In various embodiments, the retention tabs are configured to prevent the carton from unfolding and maintaining the at least one compartment for headgear straps of the mask to be retained.

In various embodiments, the at least one mask retaining feature comprises a plurality of slots/cut-outs that are configured to receive and frictionally retain the straps of headgear of the mask.

In various embodiments, the plurality of slots/cut-outs comprises two upper slots and two lower slots.

In various embodiments, the mask is configured to be secured onto the main panel by feeding headgear straps behind the main panel into the compartment through the at least one respiratory mask retaining feature that is in the form of a plurality of slots located at the main panel.

In various embodiments, first cut-out is formed on the main panel and the mask is configured to be secured by the cut out formed on main panel and a cushion module or a seal of the mask is configured to at least partially protrude out from the first cut-out.

In various embodiments, a second the cut-out is formed at the front panel to allow the further securing and also to allow at least a portion of the frame of the mask to protrude out through the second cut-out when the carton is in a closed position, wherein in the closed position the front panel of the carton is folded towards a front surface of the main panel to which the mask is retained/secured.

In another aspect, the invention broadly resides in a bag for use in packaging, the plastic bag comprising:

an opening at a top portion, an expandable base formed at a bottom portion opposite the opening configured to enable the bag to stand up on a surface, at least a front wall extending from the base to the opening and a rear wall extending from the base to the opening;

the base, the front wall and the rear wall defining an enclosure;

a viewing window located at the rear wall of the bag, wherein the bag is laser scored along the top portion and at least the rear wall or the front wall of the bag is covered with a sticker or label.

In various embodiments, the bag is made from a recyclable, biodegradable and/or compostable material.

In various embodiments, the bag comprises minimal information on it other than regulatory, manufacturing or legal information and possibly generic branding information.

In various embodiments, the opening comprises a zip lock.

In various embodiments, at least one air outlet is located underneath the zip lock.

In various embodiments, the expandable base comprises a gusset formation.

In various embodiments, bottom corners of the gusset formation are not heat sealed.

In various embodiments, the bag is adapted to be used as a part of a packaging system or to be used to package a carton.

In various embodiments, the bag is used for packaging a carton, the carton being the one as defined in any one of the above-mentioned aspects.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following description are simply exemplary embodiments of the invention. Hence, specific dimensions and other physical characteristics related to the embodiments disclosed herein are not to be considered as limiting.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprises' or 'comprised' or 'comprising' is used in relation to the apparatus or to one or more steps in a method or process.

As used hereinbefore and hereinafter, the term "and/or" means "and" or "or", or both.

As used hereinbefore and hereinafter, "(s)" following a noun means the plural and/or singular forms of the noun.

As used hereinbefore and hereinafter, and unless stated otherwise, the words "retaining" and "retention" immediately preceding a noun mean the same thing and these words are used interchangeably throughout the specification.

When used in claim and unless stated otherwise, the word 'for' is to be interpreted to mean only 'suitable for', and not for example, specifically 'adapted' or 'configured' for the purpose that is stated.

BRIEF DESCRIPTION OF THE DRAWINGS

The invention will now be described by way of example only and with reference to the drawings in which:

FIG. 28 shows a front/first compartment sheet of the carton of FIG. 25 in an open position.

FIG. 29 shows a rear/second compartment sheet of the carton of FIG. 25 in an open position.

FIG. 30 shows the central panel and the respiratory mask retention feature of the carton of FIG. 25

FIG. 40A shows carton of FIG. 39A in a closed configuration with the respiratory mask retained by the carton.

FIG. 40B shows carton of FIG. 39A in an open configuration with the respiratory mask retained by the carton. The printed information on the front surfaces of the panels of the carton is also shown.

FIG. 40C shows a rear-view carton of FIG. 39A in an open configuration without the respiratory mask retained by the carton. The printed information on the front surfaces of the panels of the carton is shown.

DETAILED DESCRIPTION

Figure 1:
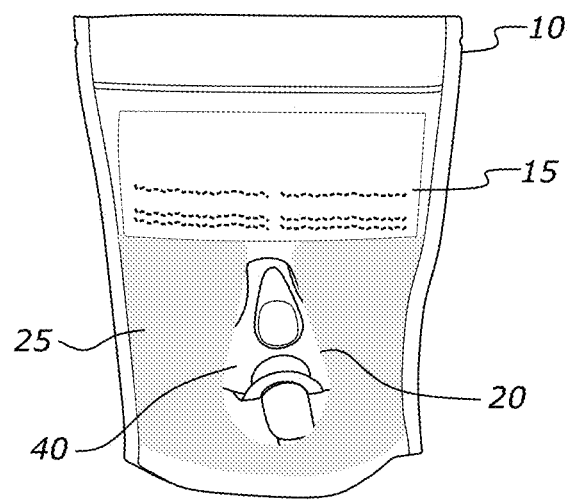
FIG. 1 shows a front side elevation view of a bag that can be used in a packaging system according to the present invention, during use.

Conventional packaging for items such as in-home medical devices present new and existing users with a large amount of information to ensure proper fitment and use, frequently leading to patient confusion, dissatisfaction, and poor treatment compliance. Therefore, it is desirable to provide packaging and collateral for items such as medical devices, including for example respiratory masks for positive airway pressure (PAP) therapy, continuous positive airway pressure (CPAP) therapy, and/or obstructive sleep apnoea (OSA) therapy that may enable patients to independently fit and use their respiratory mask, and to continue to use their respiratory mask effectively. In other words, it is desirable to provide a product or packaging system that can enable a patient to effectively independently set up and use an item such as respiratory mask, without assistance from clinical staff, or medical device company sales or support staff. Successful set up and use is important in providing the best opportunity for the patient to accept and be compliant with the therapy. Successful set up and use of the mask can be especially important for new patients with minimal or no experience of using respiratory masks.

Reference to a respiratory mask herein is intended to be reference to the combination of components that would make up such a mask including a patient interface that generally comprises a patient seal, a frame, and an inlet component. Optionally the respiratory mask may further include a headgear that generally includes one or more headgear straps and optionally one or more headgear connectors. The respiratory mask optionally also includes a conduit for connection to a flow generator.

Several preferred examples/embodiments of a packaging system according to the present invention will be described below.

In some embodiments, the present invention may provide a packaging system that may slow the pace of a user opening and removing items from the packaging system, e.g. respiratory masks, to provide a paced learning process. In comparison to current packaging or packaging systems, the packaging system of the present invention may control the amount and order of information presented to the user.

In some embodiments, the present invention may provide a packaging system with two compartments. Each compartment may serve to isolate one component or part of the respiratory mask from another component or part of the respiratory mask, or from accessories or printed information accompanying the mask. For example, the interface of the respiratory mask may be isolated from the headgear so that the headgear of the respiratory mask is not tangled and also so that the headgear (which the user/patient does not need to see initially) is hidden thereby restricting or reducing the number of items or information initially provided to the user/patient.

In some embodiments, the present invention may allow presentation of the contents of the packaging in stages that may be appropriate for the learning stage that the user is at. For example, a respiratory mask frame, and seal assembly may be presented with basic quick start user instructions in a first stage and then headgear and further instructions are provided in a second stage.

In some embodiments, the present invention may provide a more interactive opening experience that can engage the user and build confidence. The packaging of the present invention may be configured to be opened in stages or steps to reveal portions of the product and/or accompanying instructions and/or accessories, which is more engaging than the conventional packaging or packaging techniques.

In some embodiments, the present invention may provide a packaging system that is easy to use, and/or may allow efficient and effective storage/shipping of the items, and/or may provide protection against soiling and damage of the product, and at the same time may also enable the patient to:

set up their respiratory mask and equipment and be confident to start their therapy, fit and adjust their respiratory mask, displaying a basic understanding of the function of the headgear parts, and/or remain engaged or have increased engagement in their therapy, and be willing to learn more.

In some embodiments, the invention may provide packaging for the respiratory mask, that may:

prepare the user/patient for their first night of treatment/ therapy, be used as a means to educate the patient or can provide an active learning experience, prevent patient from becoming overwhelmed or frustrated when they open their respiratory mask for the first time, allow the patient to have the skill level required to successfully use the respiratory mask on the first night of treatment/therapy thereby assisting patients to feel confident to use the respiratory mask, and/or provide all information required for the first-time set-up and also information to the patient on where to go for further learning.

Figure 2:
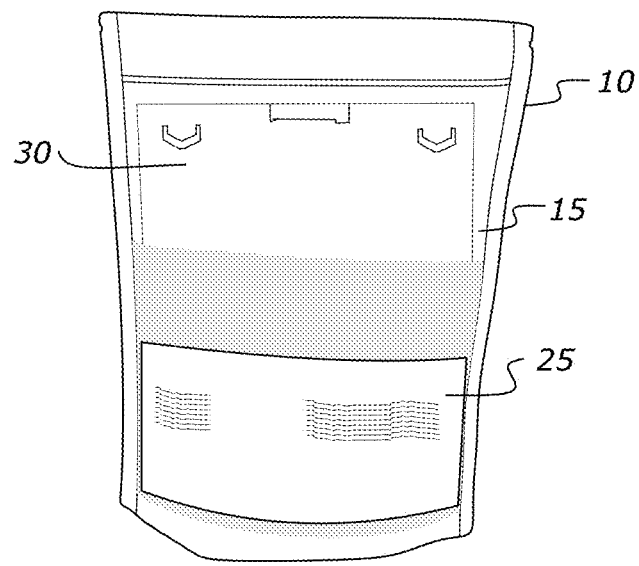
FIG. 2 shows a rear side elevation view of a bag of FIG. 1
Figure 3:
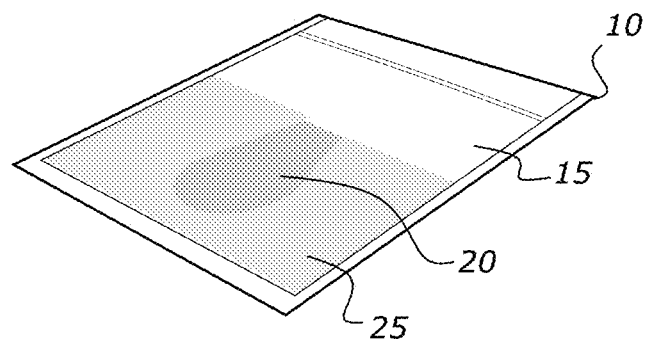
FIG. 3 shows a perspective view of the bag of FIG. 1 when empty and in collapsed position.

Reference will now be made to the accompanying drawings in which FIGS. 1 to 3 show one preferred example/embodiment of a bag 10 that may be suitable to be used in a packaging system according to an example of the present invention during use.

Bag 10 may be disposable but can be made from a material that is recyclable, biodegradable and/or compostable. As can be seen from FIGS. 1-3, bag 10 may not provide any information that the user requires to set-up and use the contained product. Bag 10 may have an expandable base to allow it to stand on a shelf.

As it can be seen in FIGS. 1-2, bag 10 may comprise a packaging insert. The packaging insert which is a carton 30 may be configured to retain item such as respiratory mask 40.

The carton 30 may comprise a first/front compartment and a second/rear compartment. The first/front compartment may contain a front portion of respiratory mask 40. The carton may display initial set up-instructions, reveal part of respiratory mask 40 and may have a window for revealing information once respiratory mask 40 is removed.

The second/rear compartment may contain a headgear of respiratory mask 40. Alternatively or additionally, it may contain a quick reference guide and/or user instructions, and retention features for securing the quick reference guide and/or user instructions to the packaging such that the quick reference guide and user instructions may be properly secured inside the second compartment.

The packaging carton 30 may also comprise at least one item retaining feature which in this example is a respiratory mask retaining feature(s) adapted to secure the respiratory mask 40 to/within the packaging carton 30. The respiratory mask retaining feature(s) may also maintain the respiratory mask 40 in an assembled configuration and may help to prevent other components such as headgear straps from tangling.

The packaging carton 30 may further comprise self-retaining fasteners/closures that can retain the packaging carton 30 in a closed configuration without the need for adhesives or separate fasteners.

Several preferred examples/embodiments of a packaging carton 40 will be described later in more detail.

Bag 10 may have minimal information on it other than regulatory, manufacturing or legal information and possibly generic company branding. This can reduce the information presented to the patient when respiratory mask 40 is received, to reduce confusion. All the patient need know is that bag 10 contains respiratory mask 40.

As it can be seen from FIGS. 1-3, bag 10 may have a transparent region 15 at the top of bag 10. The transparent region 15 can allow product branding and sizing information on the packaging carton 40 to be visible through bag 10. That may enable the user to identify the contents of bag 10.

Bag 10 may further comprise a transparent viewing window 20 on the front so that part of the item such as respiratory mask 40 is visible through the transparent viewing window 20 as shown in FIG. 1.

Bag 10 can protect items such as respiratory mask 40 from contamination and damage and to keep the item, associated instructions any other collateral together during shipping.

Reducing the information on bag 10, i.e., removing product information and instructions, may help to communicate to the user that bag 10 is not intended to be kept and can be thrown away once the item and other collateral has been removed from within bag 10.

Bag 10 may have a foldable base that can enable it to stand up on a surface and can include a closure means such as zip lock at the opening.

FIGS. 4-7 show an example/embodiment of carton 100 according to one preferred embodiment of the present invention.

Figure 4:
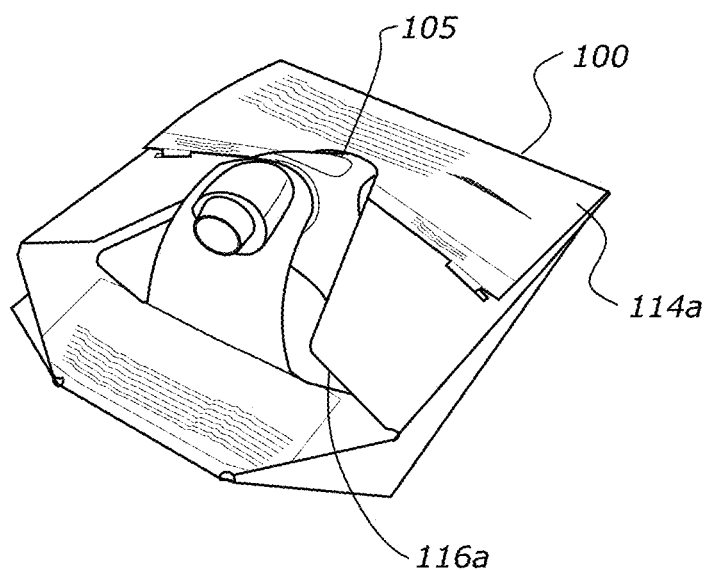
FIGS. 4-6 show an example/embodiment of a carton according to a first preferred embodiment of the present invention in closed configuration.
Figure 5:
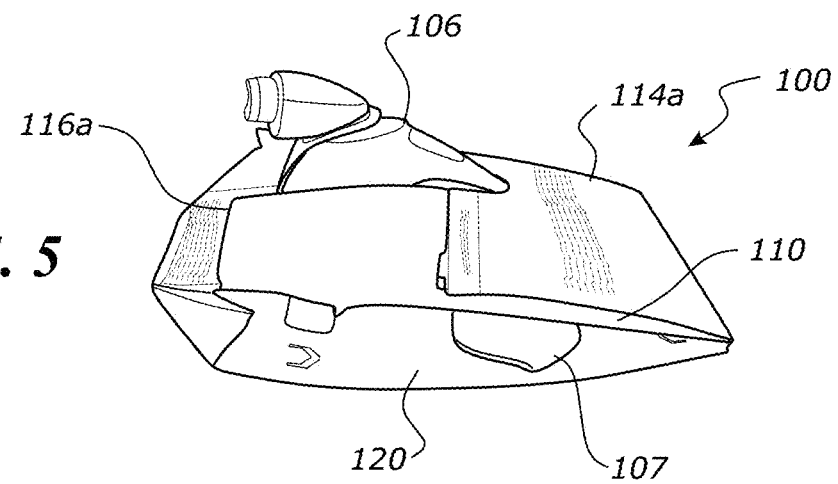
Figure 6:
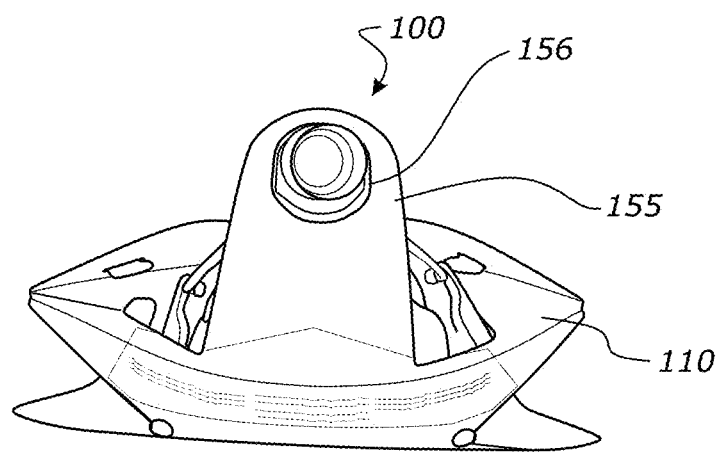

The carton 100 is formed of a sheet material, preferably a cardboard or a punched sheet of cardboard that may be folded to retain and at least partially enclose respiratory mask 105 comprising a patient interface and headgear, and any other collateral such as user instructions. As shown in FIGS. 4-6, the carton 100 may fold to form two compartments 110, 120. The first compartment 110 is a front compartment that is adapted to contain patient interface 106 of the respiratory mask 105 and the second compartment 120 is a rear compartment that is adapted to contain the headgear 107, quick reference guide and other user instructions. The second compartment 120 may also contain spare respiratory mask components. The first compartment 110 is configured to be opened first to reveal the respiratory mask 105 and present information in sequential order or stages. The sequential order may be predetermined by the manufacturer/supplier of the respiratory mask. The second compartment 120 is configured to be accessible from both the first compartment and the sides. In an alternative embodiment, the second compartment 120 can be configured to be fully opened.

Figure 7:
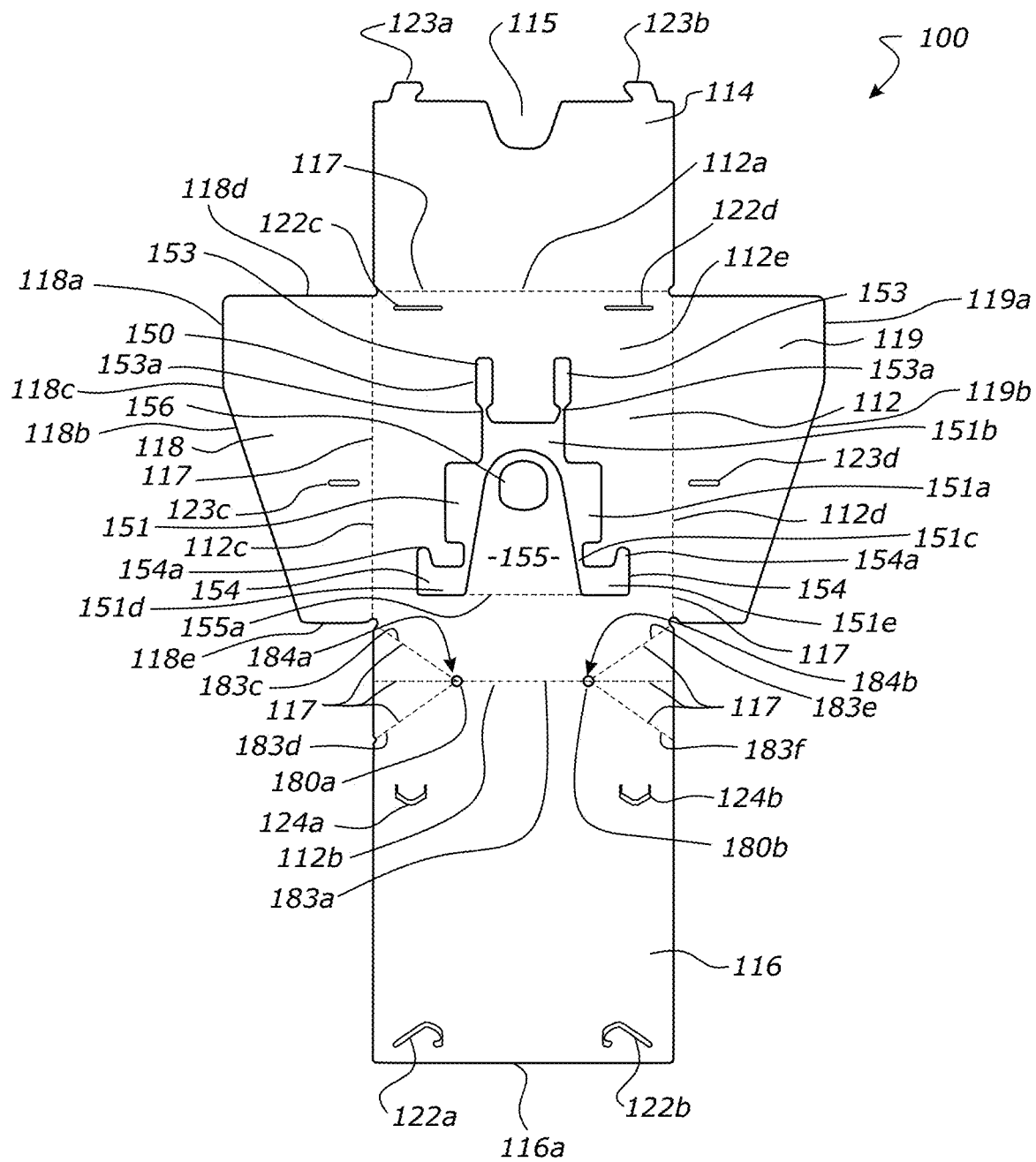
FIG. 7 shows an example/embodiment of a carton of FIGS. 4-6 in an open configuration.

The carton 100 is formed of a sheet material that is configured to form at least two compartments for use in packaging an item such as respiratory mask 105. As shown in FIG. 7, the carton 100 may comprise a main panel 112 which is a central panel 112. The central panel 112 is an internal panel having at least a first side 112a, a second side 112b, a third side 112c and a fourth side 112d). The central panel 112 also has a front surface 112e and a rear surface not shown. As shown in FIG. 7, the first side 112a is a first edge, the second side 112b is the second edge, the third side 112c is the third edge and the fourth side 112d is the fourth edge of the central panel 112.

A top flap 114 is hinged and extends from the first side 112a of the central panel 112. Similarly, a rear panel 116 is hinged and extends from the second side 112b of the central panel 112. The second side 112b is opposite to the first side 112a.

There are first and second side flaps 118 and 119 that are hinged and extend from the third side 112c and the fourth side 112d of the central panels respectively where the third and fourth sides 112c and 112d are lateral sides of the central panel 112 and are located opposite to each other.

Figure 7A:
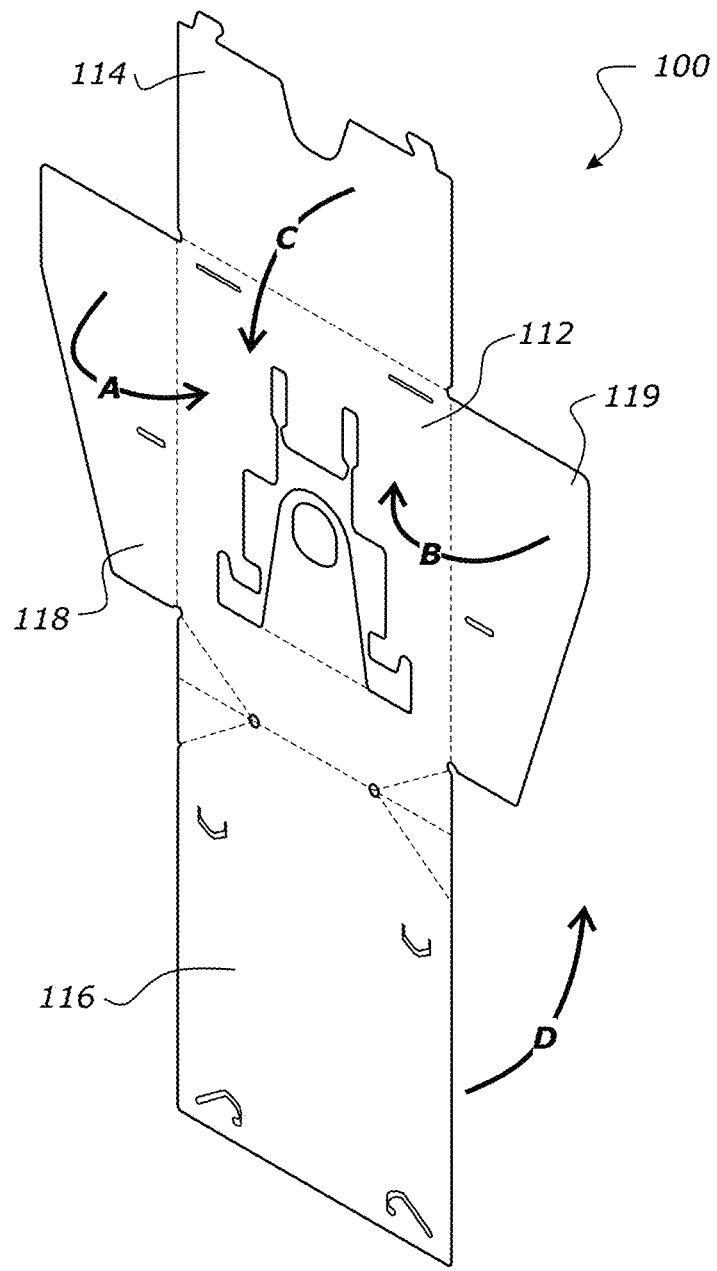
FIG. 7a shows an example/embodiment of how carton of FIG. 7 may be folded to be in a closed configuration.

When the carton 100 is in a closed configuration as shown in FIGS. 4-6, the central panel 112, the first and second side flaps 118, 119 are configured to be folded over the front surface or in a first direction. This is as shown by arrows A and B in FIG. 7A. Similarly, the top flap 114 is also configured to be folded over the front surface 112e or in a first direction. This is shown by arrow C in FIG. 7A. When folded, the central panel 112, the first and second side flaps 118, 119 and the top flap 114 are configured to form a first compartment 110. Similarly, the rear panel 116 is configured to be folded over the rear surface of the central panel 112 or in a second direction. This is shown by arrow D in FIG. 7A. When folded, the central panel and rear panel are configured to form a second compartment 120.

The carton 100 may be formed of a single sheet material such as cardboard, a punched sheet of cardboard or plastic or many other suitable materials.

As shown in FIG. 7, the carton 100 may comprise fold lines 117. The fold lines 117 may allow the top flap 114, the rear panel 116, the first side flap 118 and the second side flap 119 to be hinged to the respective side of the central panel 112. As shown in FIG. 7, the fold lines 117 may be formed at the perimeter of the central panel 112 and therefore horizontal fold line 183a may be formed between the central panel 112 and the rear panel 114. The horizontal fold line 183a may extend laterally across the rear panel 116. Two diagonal fold lines 183c, 183e may extend from outermost lateral edges of the central panel 112 to the horizontal fold line 183a at a junction 184a, 184b respectively. Similarly, two diagonal fold lines 183d, 183f may extend from outermost lateral edges of the rear panel 116 to the horizontal fold line 183a at a junction 184a, 184b respectively. As shown, circular holes 180a, 180b may be formed at or near the junctions 184a, 184b to reduce stress within the junction 184a, 184b and prevent tearing.

The first compartment 110 may be configured to be partially enclosed. For example, the front compartment 110 may be configured to be open at one edge such as a bottom edge 116a.

The rear panel 116 may comprise at least one rear panel retention feature and the central panel comprises at least one complementary feature that is adapted to engage with the rear panel retention feature thereby allowing the rear panel 116 and the central panel 112 to be fastened together.

As shown in FIG. 7, the rear panel retention feature can be in the form of two rear panel retention tabs 122a, 122b that are adapted to be received by complementary feature in the form of two rear panel retention slots 122c, 122d. Preferably, rear panel tab 122a is configured to be received by rear panel retention slot 122c and the other rear panel retention tab 122b is configured to be received by rear panel retention slot 122d.

The second compartment 120 may be configured to provide a partially enclosed space, more preferably is configured to closed only on top and bottom edges, as shown in FIG. 5. Alternatively, the second compartment 120 may be sealed on at least one side.

The top flap 114 may be configured to fold over the first and second side flaps 118, 119. The top flap 114 may comprise top flap retention features, and each of the side flaps 118, 119 may comprise at least one complementary feature adapted to engage with at least one of the top flap retention features thereby allowing the top flap and the side flaps to be fastened together.

As shown in FIG. 7, the top flap retention features may be in the form of hooks, tabs or top flap fastening tabs 123a, 123b and the at least one complementary feature on each of the side flaps 118, 119 is a top flap retention slot 123c, 123d adapted to receive one of the top flap fastening tabs 123a, 123b. Preferably, tab 123a is configured to be received by slot 123c and the tab 123b is configured to be received by slot 123d.

The top flap retention features or tabs 123a, 123b may be located along an upper edge of the top flap 114 as shown in FIG. 7.

The top flap 114 may include a U-shaped notch 115 or a cut-out that is configured to reveal an upper portion of a mask frame of the respiratory mask 105 when the carton 100 in closed configurations shown in FIGS. 4-6. The U-shaped notch 115 may form part of a window in the first compartment 110 and is configured to reveal part of the respiratory mask, particularly the patient interface. As shown in FIG. 7, each of the side flaps 118, 119 may be of a polygonal shape, and the lateral edges of the side flaps 118,119 may have an upper edge portion 118a,119a and a lower edge portion 118b,119b. The lower edge portions are angled to form an acute angle with the lateral sides of the central panel 112. The upper edge portion 118a,119a may extend further from the central panel 112 than the lower edge portion 118b,119b. By way of example, the upper edge portion 118a may begin at a top edge 118d of side flap 118 and continue until an intermediate point 118c along a side edge of the side flap 118, preferably about one quarter to one third the length of a side edge of the side flap 118. The lower edge portion 118b may begin at the intermediate point 118c of side flap 118 and continue until the bottom 118e of the side edge of the side flap 118, preferably about two thirds to three quarters the length of a side edge of the side flap. Side flap 119 may have the same structure. Having such side flaps 118, 119 can form a window to reveal part of the respiratory mask, when the packaging is folded or in a closed configuration, the window being defined by the opposing lower edge portions of side flaps 118,119 and the U-shaped notch 115. The window is generally triangular in shape to follow a generally triangular shape of the respiratory mask. The side panels 118, 119 may be of any suitable polygonal shape, but are generally triangular or trapezoidal (preferably acute trapezoidal) in shape. In alternative embodiments the window can have any shape suitable for revealing a front of a different mask.

The top flap 114 may include a first information panel 114a that is adapted to present a user with an information regarding use of the item. The first information panel may be located on an external surface of the top flap such that the first information panel is visible when the carton 100 is in closed configuration.

Each of the central panel 112, side flaps 118, 119 and the top flap 114 may provide space for printing information or instructions for the user.

The central panel 112 may include at least one item retention feature that is configured to retain an item or an assembly of an item. The at least one item retention feature may comprise a plurality of features or geometries that are configured to work together to retain an item or an assembly of an item.

In FIG. 7, the item retention feature 150 is a respiratory mask retention feature 150 configured to retain respiratory mask 105. The respiratory mask retention feature 150 may comprise a plurality of features that are configured to work together retain respiratory mask 105 to the carton 100.

As shown, the respiratory mask retention feature 150 may be located at a central location of the central panel 112. The respiratory mask retention feature 150 may comprise a first cut-out 151 hereinafter referred to as a first aperture 151 or window that can allow portions of the respiratory mask, including any headgear of respiratory mask 105 to pass from the first compartment 110 to the second compartment 120.

As shown in FIG. 7, the first aperture 151 has a stepped perimeter that may include or define a rectangular window or window region. Specifically, the first aperture 151 may comprise a central rectangular portion 151a, a top rectangular portion 151b that is proximal to the top flap 114 and a bottom inverted T-shaped portion 151c that is proximal to the rear panel 116. The central rectangular portion 151a, top rectangular portion 151b and bottom inverted T-shaped portion 151c may be configured to be a continuous window or opening and form a single aperture, namely the first aperture 151, in the central panel 112. The rectangular window may be configured to reveal printed information (such as quick reference guide) located in the second compartment 120. Preferably, the window or window region is shaped and sized to reveal certain information of the informative material, particularly once the respiratory mask is removed during opening and unpacking. A quick reference guide may be an item such as sheet(s) of paper that provides user with just enough information without having to read entire user manual. The sheets(s) may be folded.

Respiratory mask retention feature 150 may comprise upper strap slots 153 and a lower strap slots 154 which may be configured to receive and optionally frictionally retain straps of respiratory mask 105 or more preferably, straps of a headgear 107 of respiratory mask 105. The upper strap slots 153 may be of substantially rectangular shape extending longitudinally from the first aperture 151 towards top flap 114. The upper strap slots 153 may include narrow regions 153a extending between the upper strap slots 153 and the first aperture 151. In use, the narrow regions 153a are configured to retain the straps of the respiratory mask in the upper strap slots 153. Narrow regions 153a provide a path through which the headgear straps can enter strap slots 153 and provide a retention feature to prevent the straps from falling out of strap slots 153. Similarly, the lower strap slots 154 may extend orthogonally from each of left and right extension slots 151d,151e of the lower T-shaped portion 151c of the first aperture 151 towards the direction of the top flap 114. Left and right extension slots 151d,151e are transverse to and lead into lower strap slots 154, and provide a path through which the headgear straps can enter the strap slots 154. Left and right extension slots 151d,151e provide a retention feature, in the form of a shoulder or stepped portion at the transition between the strap slot and the extension slot, to prevent the straps from falling out of strap slots 154. The upper strap slots 153, the lower strap slots 154, the narrow regions 153a and the first aperture 151 may be formed as continuous window or opening, in other words formed as a single aperture/cut-out in the central panel 112.

Respiratory mask retention feature 150 may comprise an inlet component support tab 155 having a second cut-out, hereinafter referred to as a second aperture 156 that is adapted to receive an inlet component such as elbow, conduit etc. of respiratory mask 105, as shown in FIG. 6. As shown in FIG. 7, the inlet component support tab 155 may be formed as a tongue extending from the central panel 112 at a location that is between the two lower strap slots 154. The inlet component support tab 155 may extend from fold line 255a formed between the inlet component support tab 155 and the central panel 112 so that it can hinge with respect to the central panel 112. The inlet component support tab 155 may be wider at a bottom portion that is proximal to the fold line 155a and gradually taper upwards so that the width at the top portion that is distal to the fold line 155a is narrower in width than the bottom portion. In the depicted embodiment, the support tab 155 is generally triangular or trapezoidal in shape and has a rounded top portion. The inlet component support tab 155 is configured to bend away from central panel 112 and curve over front of respiratory mask to provide a support that holds the respiratory mask in a vertical direction and can prevent respiratory mask from falling out the bottom of front compartment 110.

Inlet component support tab 155 may begin at the same height as the lower strap slots 154. In other words, similar to lower strap slots 154, the inlet component support tab 155 may also extend from the lower edge of the first aperture 151, as shown in FIG. 7.

In combination, the mask retention feature 150 and inlet component support tab 155 may retain a patient interface, optionally including a patient seal and a frame, on the front surface of the central panel 112. The patient seal may be in the form of a cushion module.

The rear panel 116 may include one or more additional retention features that may be configured to hold at least one item such as but not limited to a quick reference guide, a user instruction manual in pamphlet form etc.

As shown in FIG. 7, the one or more additional retention features comprise tabs 124a, 124b that may be configured to overhang edges of the at least one item held on the tabs 124a, 124b.

The positioning and shape of any retention features such as tabs and slots described above may be varied to suit any respiratory masks that require packaging.

From the above, it can be appreciated that no adhesives or permanent fasteners may be required for the carton 100 to remain in a closed configuration as shown in FIGS. 4-6. In alternative embodiments, it may be desirable to seal the carton, such as with adhesive or mechanical fasteners (for example, pins, clips, or staples).

The carton 100 may be configured to be placed in a bag 10 as an insert.

Figure 8:
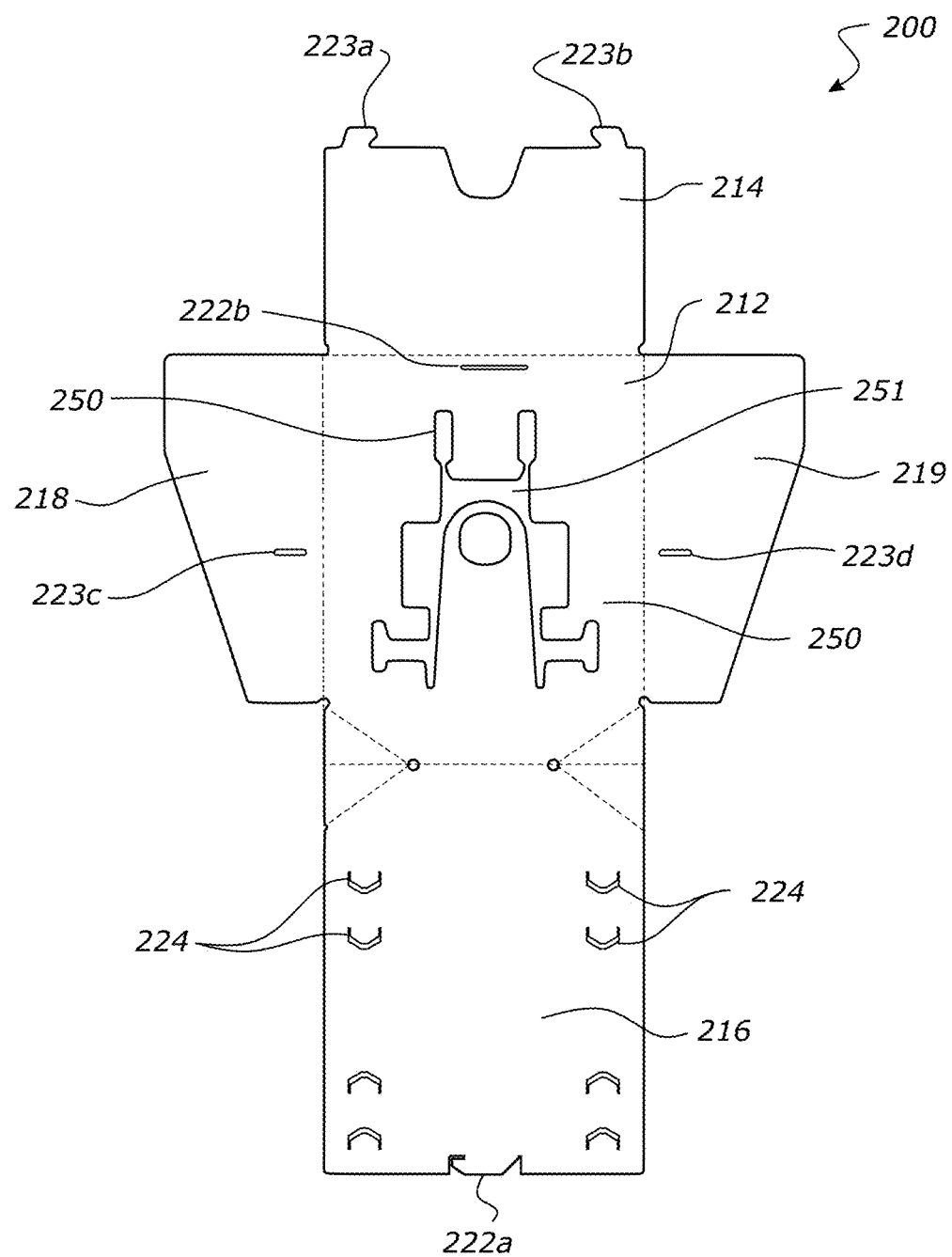
FIG. 8 shows an example/embodiment of a carton according to a second preferred embodiment of the present invention in an open configuration.
Figure 9:
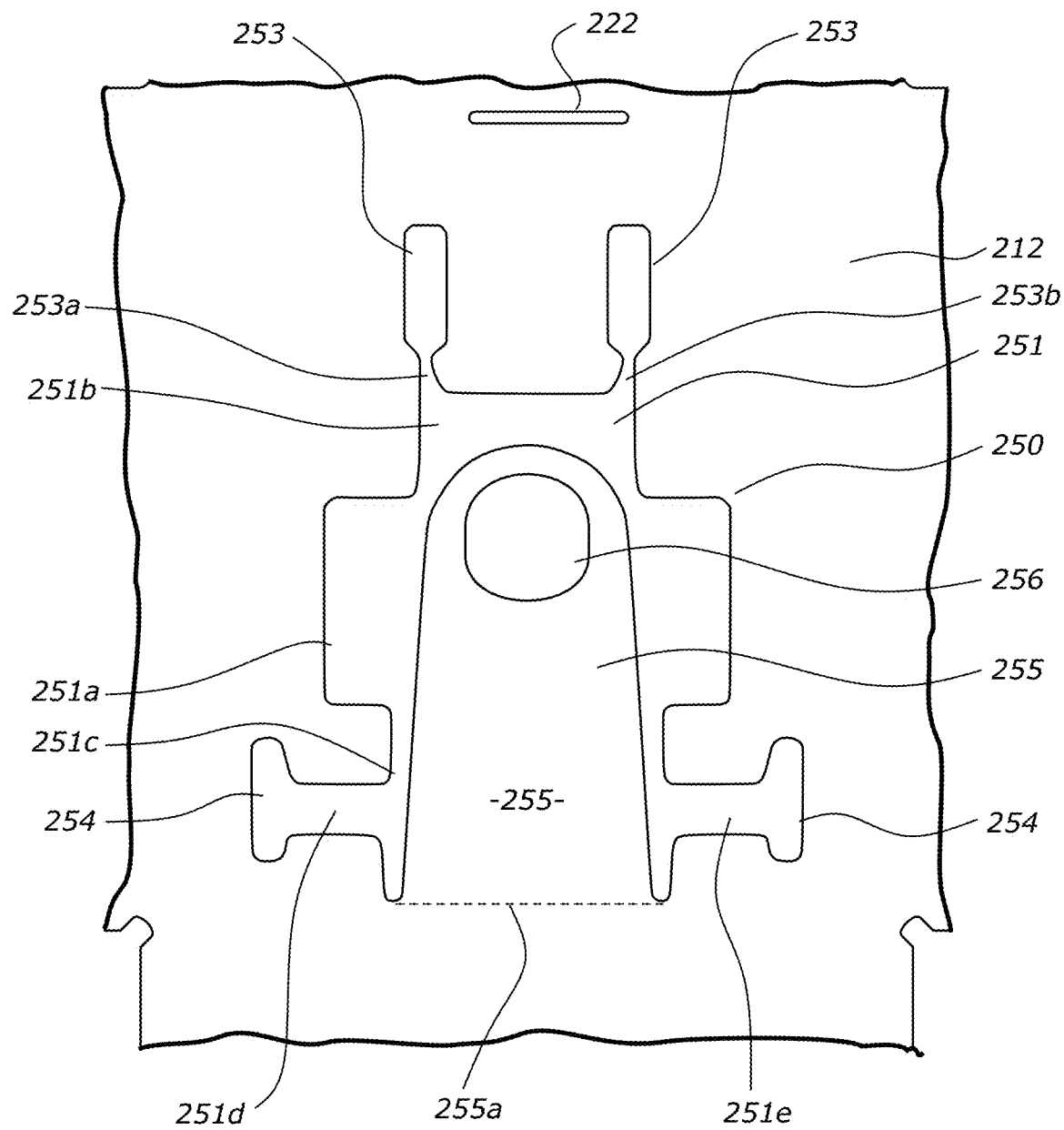
FIG. 9 shows the central panel and the respiratory mask retention feature of the carton of FIG. 8

FIG. 8 shows an example/embodiment of a carton 200 according to second preferred embodiment of the present invention in an open configuration. FIG. 9 shows a main panel 212 which is a central panel 212 and the respiratory mask retention feature 250 of the carton 200 of FIG. 8.

The carton 200 of the second preferred embodiment is substantially the same as the carton 100 as described above with reference to FIGS. 4-7 with some variations in the respiratory mask retention feature 250, the rear panel retention feature 222 and the user instruction retention features 224. These variations can be identified by comparing FIG. 7 with FIGS. 8 and 9. In FIGS. 8 and 9, items of mask retention feature 251 similar to those shown in FIG. 7 are identified with the same reference numeral, incremented by 100.

As shown in FIGS. 8 and 9, the first aperture 251 may comprise a central rectangular portion 251a, a top rectangular portion 251b that is proximal to the top flap 214 and a bottom rectangular portion 251c that is proximal to the rear panel 216. A left extension slot 251d and a right extension slot 251e extend respectively from the left and right sides of the bottom rectangular portion 251. The central rectangular portion 251a, top rectangular portion 151b, bottom rectangular portion 251c, the left extension slot 251d and the right extension slot 251e may be configured to be a continuous window or opening and form a single aperture/cut-out, namely the first aperture 251, in the central panel 212.

The upper strap slots 253 may be of substantially rectangular shape extending longitudinally towards the top flap 214. The upper strap slots 253 may include narrow regions 253a extending from the upper strap slots 253 and the first aperture 251. In use, the narrow regions 253a are configured to retain the straps of the respiratory mask in the upper strap slots 253. Narrow regions 253a provide a path through which the headgear straps can enter strap slots 253 and provide a retention feature to prevent the straps from falling out of strap slots 253. Similarly, the lower strap slots 254 may extend orthogonally from each of left and right extension slots 251d,251e of the lower rectangular portion 251c of the first aperture 251, and towards both the top flap 214 and the bottom flap 216 such that the slots 254 project beyond, and orthogonally to the side slots 251d,251e. Left and right extension slots 251d,251e are transverse to and lead into lower strap slots 254, and provide a path through which the headgear straps can enter the strap slots 254. Left and right extension slots 251d,251e provide a retention feature, in the form of a neck or corresponding stepped portions or shoulders at the transition between the strap slot and the extension slot, to prevent the straps from falling out of strap slots 254. The upper strap slots 253, the lower strap slots 254, the narrow regions 253a and the first aperture 251 may be formed as continuous window or opening, in other words formed as a single aperture in the central panel 212.

As shown, like the first preferred embodiment, the respiratory mask retention feature 250 of this second preferred embodiment also includes an inlet component support tab 255. The inlet component support tab 255 of begins below a lower strap slots 254 as shown in FIGS. 8 and 9. In other words, the inlet component support tab 155 extends from a lower edge of the first aperture 251 and that lower edge is more proximal to the rear flap 216 than the lower strap slots 254.

Also, the rear panel retention feature of this second preferred embodiment comprises a single hook shaped tab 222a that is set into the lower edge of the rear panel 216 as shown in FIG. 8. The single hook shaped tab 222 is configured to engage with a retention slot 222b that is centrally located near the top edge of the central panel 212.

Figure 17:
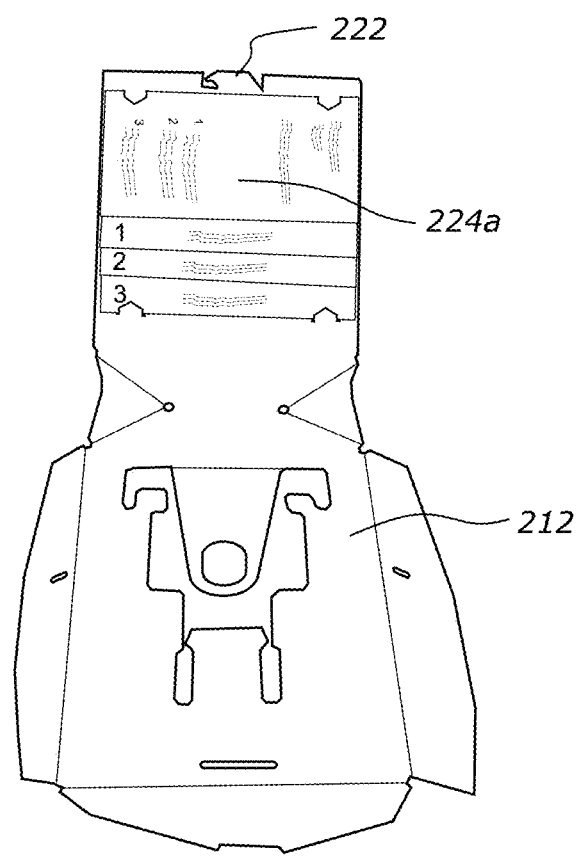

As seen in FIG. 8, the rear panel 216 includes additional retention features configured to hold at least one item such as but not limited to a quick reference guide, a user instruction manual in pamphlet form etc. These retention features comprise tabs 224 that overhang edges of the items such as a quick reference guide 224a as shown in FIG. 17.

Of course, it will be appreciated that the top flap tabs 223a, 223b and the rear panel retention features can be of any suitable shape and size to retain the carton 200 in a closed configuration.

Also, the positioning and shape and number of any retention features such as tabs and slots may be varied to suit respiratory masks that require packaging.

Again, similar to the carton 100, it can be appreciated that no adhesives or permanent fasteners may be required for the carton 200 to remain in a closed configuration.

One example of a process of unpacking the packaging system that uses the second preferred embodiment of the carton 200 will now be described with reference to FIGS. 10-17. However, this may equally apply to the packaging system that uses the first preferred embodiment of the carton 100 or a third preferred embodiment of the carton 300 that is described later in the specification.

Figure 10:
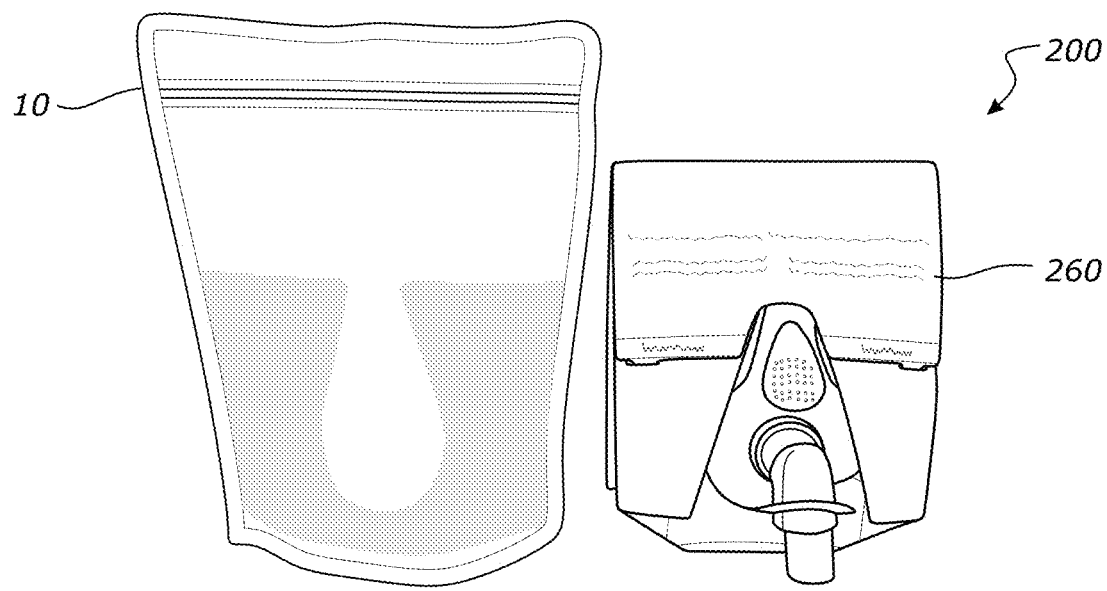
FIGS. 10-17 shows an example of a process of unpacking where the packaging system uses the carton of FIGS. 8-9.
Figure 11:
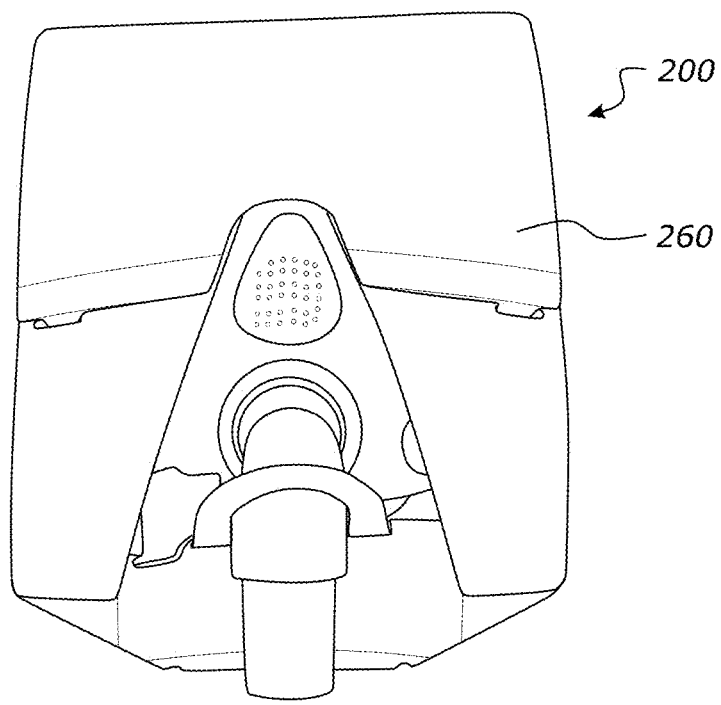
Figure 12:
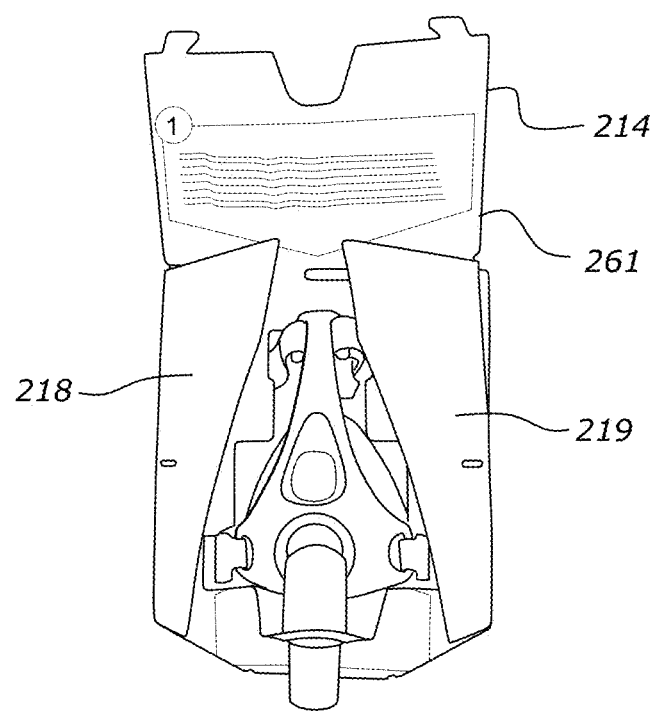
Figure 13:
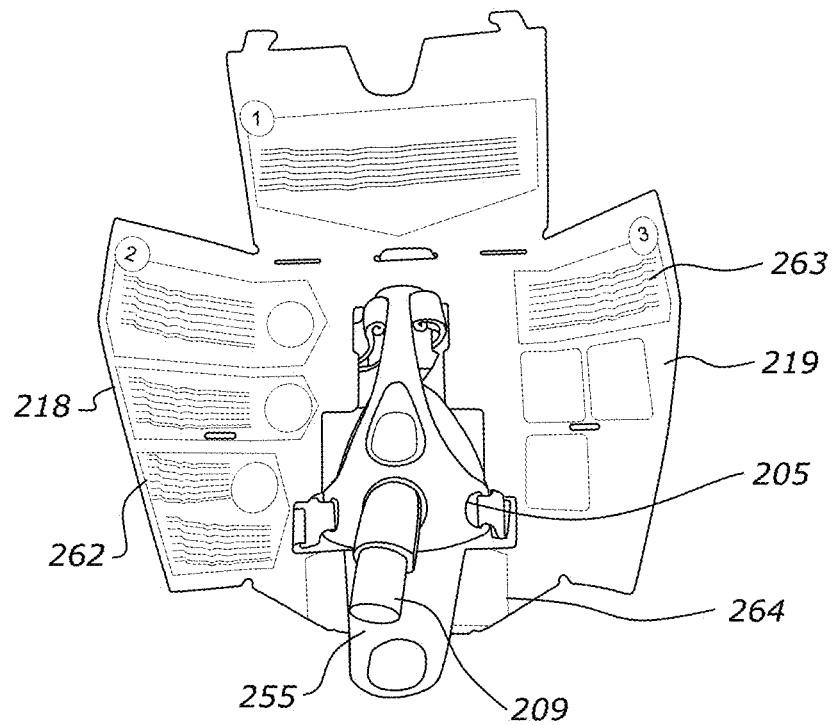
Figure 14:
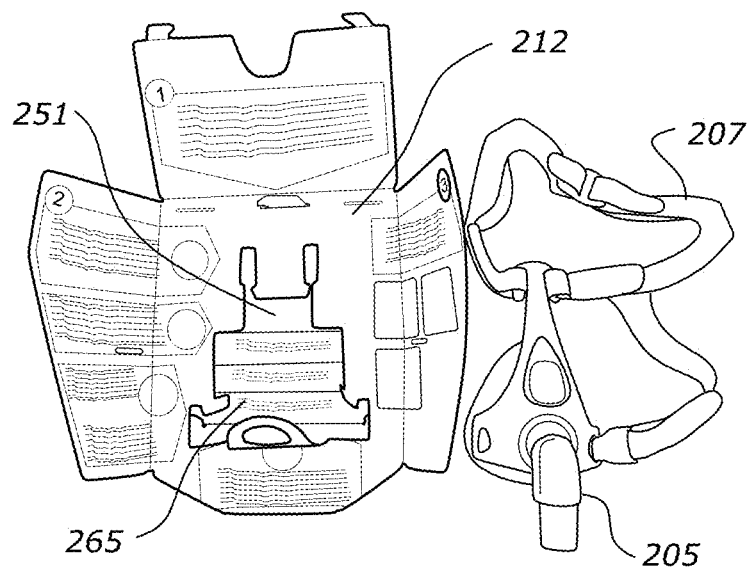
Figure 15:
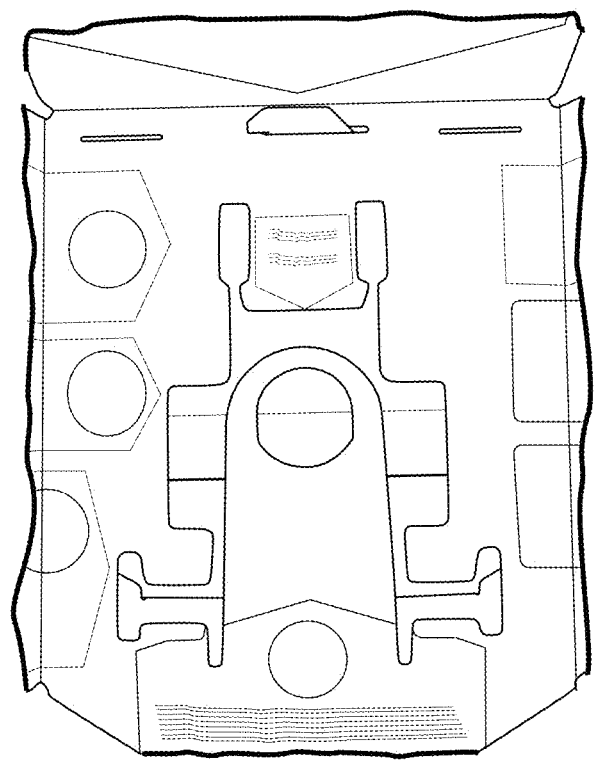
Figure 16:
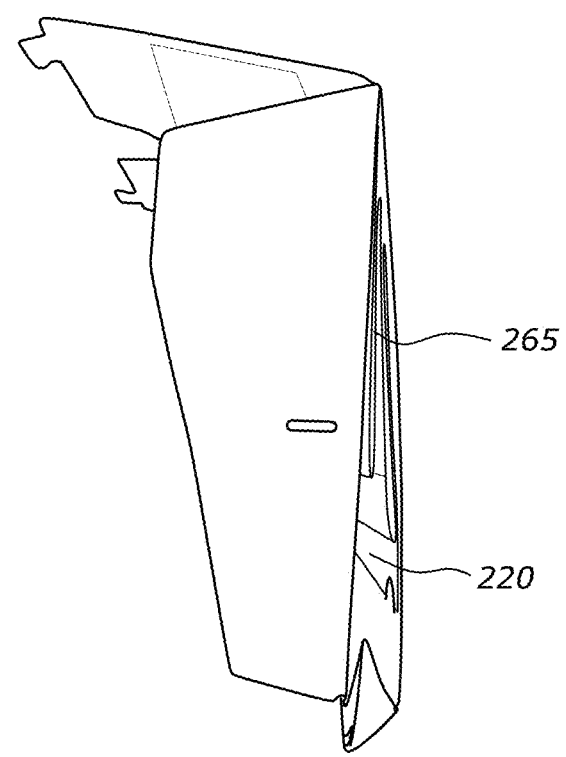

The following steps may be performed for unpacking where the packaging system uses carton 200:

1. Remove respiratory mask and insert/carton 200 from bag 10 as shown in FIG. 10. When this step is performed, first opening instructions 260 are revealed as shown in FIGS. 10 and 11.
2. Unfasten and lift top flap 214 as shown in FIG. 12. When this step is performed, the first information block 261 is revealed and the side flaps 218, 219 will be released. The information block 261 may contain basic initial setup instructions or part of basic initial setup instructions.
3. Unfold side flaps as shown in FIG. 13. When this step is performed, further information blocks 262, 263, 264 surrounding respiratory mask 205 that is retained to the carton 200 may be revealed. The information blocks 262,263,264 may be arranged in such a way that it can guide the user through them in an appropriate order. More of respiratory mask may also be revealed in this step.
4. Release inlet component 209 of respiratory mask 205 from the inlet component support tab 255. For example, the inlet component support tab 255 may be pivoted/ hinged away from respiratory mask retention feature 250 until a suitable position is reached in which the inlet component 209 of respiratory mask 205 may be easily removed through the second aperture 256 of the inlet component support tab 255.
5. Remove the respiratory mask 205 from the carton 200 as shown in FIG. 14. To perform this step, headgear 207 of the respiratory mask 205 may be pulled through the aperture 251 located at or near the centre of the central panel 212. When the respiratory mask 205 is removed from the carton 200, further information such as a quick reference guide 265 that may be positioned behind the internal panel may be revealed through the window/ aperture 251. Also, see FIG. 15.
6. Remove quick reference guide 265 from the rear compartment 220 as shown in FIGS. 16 and 17. The quick reference guide 265 can be slid out of a side of the rear/second compartment 220, or the rear compartment 220 may be opened by releasing the rear panel retention feature such as tab 222a from engagement with the central panel 212, more specifically with slot 222b. The quick reference guide 265 may duplicate information already contained in the carton, which means once the quick reference guide has been removed, the carton 200 may be discarded or thrown away. User instructions, spare respiratory mask component and/or other collateral can be removed from the rear compartment.

An example/embodiment of a packaging carton 300 according to third preferred embodiment of the present invention will now be described with reference to FIGS. 18 to 24.

Figure 18:
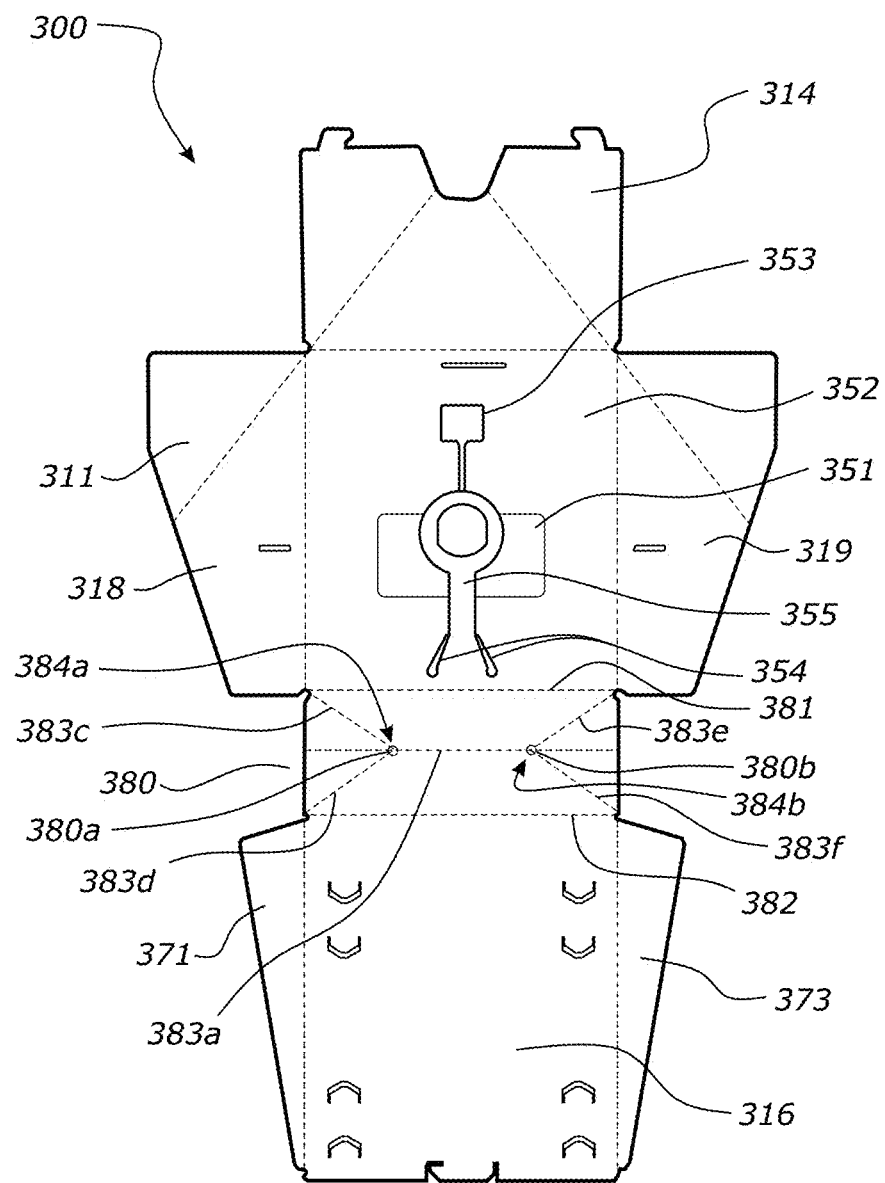
FIG. 18 shows an example/embodiment of a carton according to a third preferred embodiment of the present invention in an open configuration.
Figure 19:
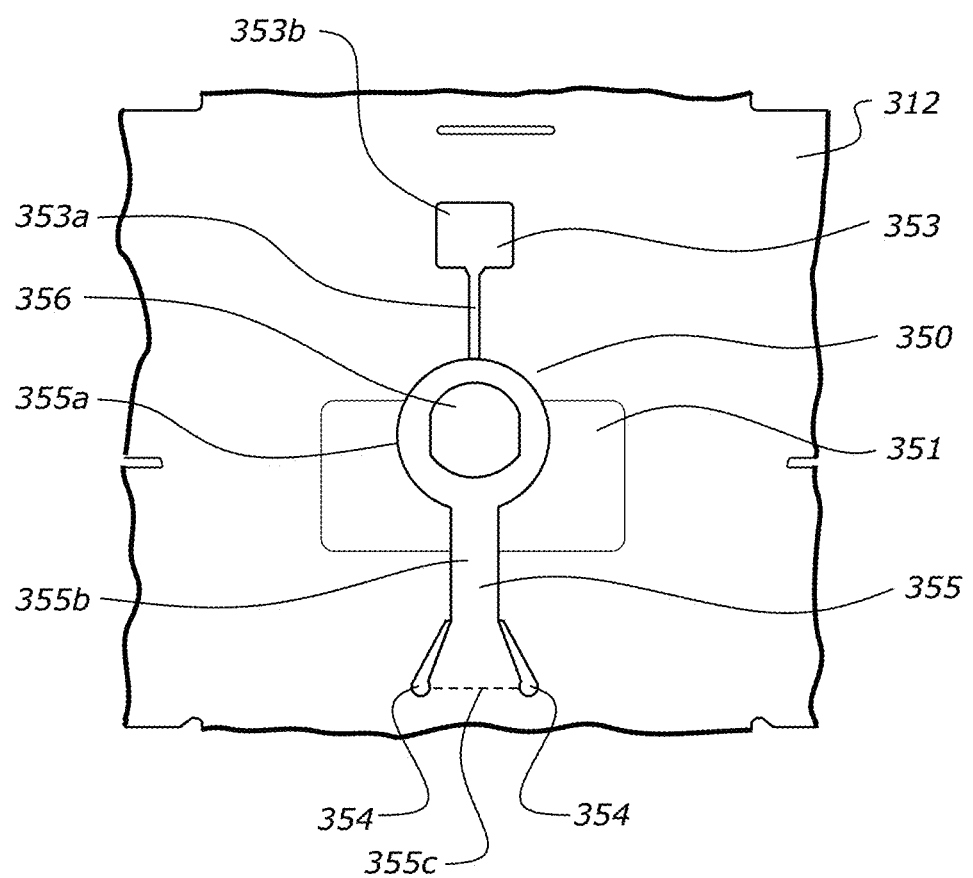
FIG. 19 shows the central panel and the respiratory mask retention feature of the carton of FIG. 18
Figure 20:
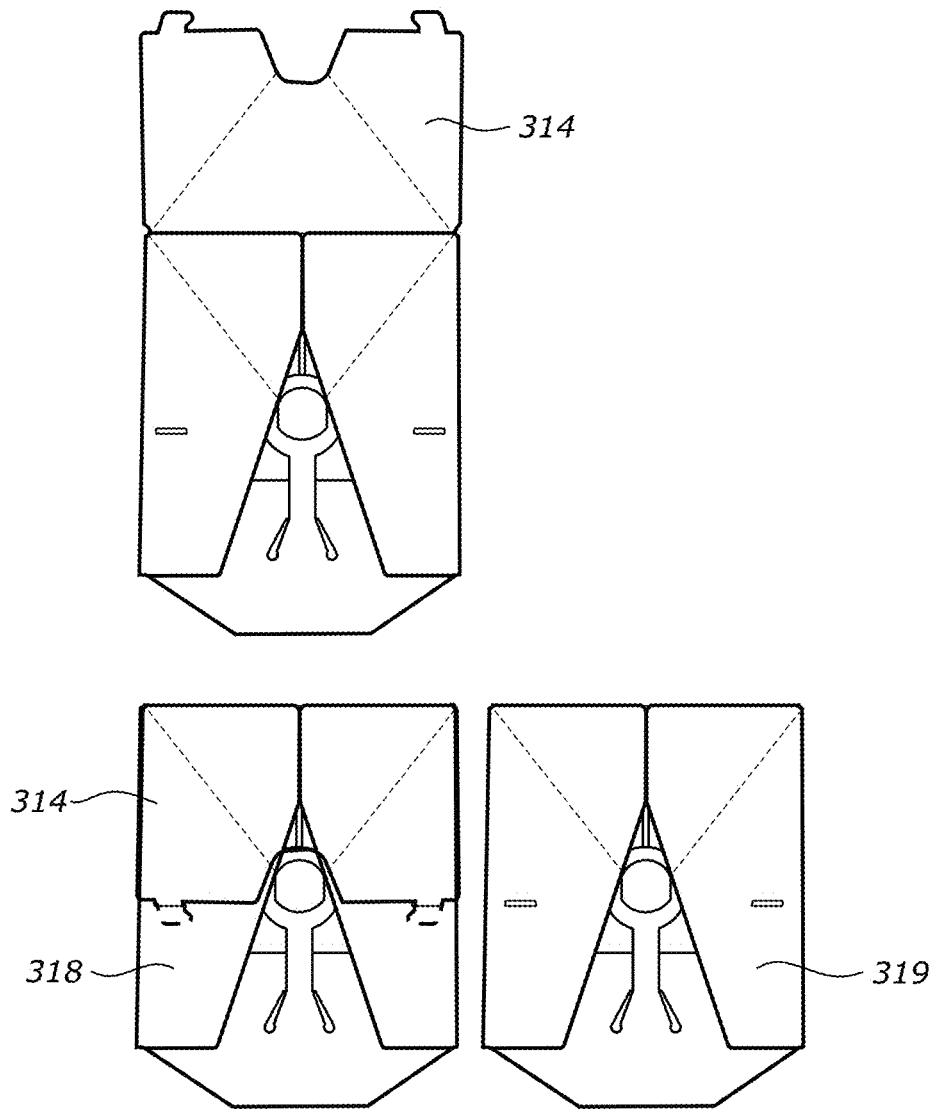
FIG. 20 shows the carton of FIG. 18 in a partially folded condition.

FIG. 18 shows an example/embodiment of a packaging carton 300 according to third preferred embodiment of the present invention in an open configuration. FIG. 19 shows a main panel 312 which is a central panel 312 and respiratory mask retention feature 350 of the carton 200 of FIG. 18. FIG. 20 shows how top flap 314 may be folded and secured with side flaps 318, 319. FIGS. 21-24 show carton 300 or part of that carton when in closed configuration.

The carton 300 of the third preferred embodiment is substantially the same as the carton 100,200 as described above but with some variations. Therefore, only those variations will be described below.

Those variations can also be identified by comparing each of the FIGS. 7 and 8 with FIG. 18.

Figure 22:
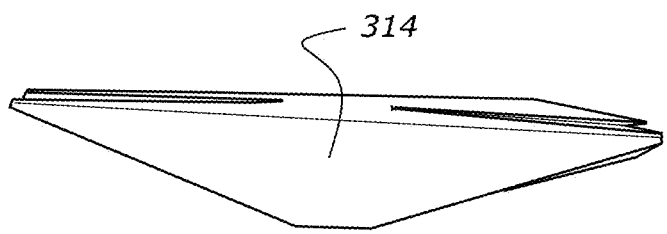

One variation is in the fold lines. These the fold lines are shows as dotted in FIG. 18. As shown in FIG. 18, there are diagonal fold lines on the side flaps 318, 319 and a top flap 314. Specifically, the diagonal fold lines may extend from the edges of each side flaps 218, 319 to a lower portion of the U-shaped notch 315 as shown in FIG. 18. the diagonal fold lines can form a more defined space for respiratory mask in the front compartment as opposed to not having the fold lines and the panels are curved and tend to be biased towards a flat state. As shown in FIG. 22, the shape of the front or first compartment 310 formed using the carton 300 is more triangular when viewed from above. This can create more internal space near the lateral central of the front/first compartment 310 for respiratory mask to be positioned inside without being crushed. See FIGS. 23-24.

Respiratory mask retention feature 350 comprises features that include a single upper strap slot 353 unlike two upper strap slots in the previous two embodiments. The single upper strap slot 353 may extend from the first cut-out 351, hereinafter referred to as a first aperture 351 and may comprise a neck portion 353a that is proximal to the first aperture 351 and a rectangular head portion 353b that is distal to the first aperture 351. The single upper strap slot may be formed to be continuous opening with the first aperture 351. The single upper strap slot 353 may receive and frictionally retain straps of respiratory mask or more preferably, straps of a headgear of respiratory mask. In other words, the single upper strap slot 353 may receive and frictionally retain a pair of straps that attach to a forehead support of respiratory mask. This arrangement may help to retain respiratory mask more centrally and securely.

The inlet component support tab 355 of this third preferred embodiment is also narrower than those of the first and second preferred embodiments. The shape of the inlet component support tab 355 of this third preferred embodiment differs from those of the first and second preferred embodiments. Specifically, as shown in FIG. 19, the inlet component support tab 355 comprises a circular head portion 355a and an elongated neck portion 355b extending between the circular head portion 355a and the central panel 312. A second cut-out, hereinafter referred to as a second aperture 356 is formed in the circular head portion 355a, and is configured to receive an inlet component of a respiratory mask. The inlet component support tab is hinged with respect to the central panel due to fold line 355c. The narrower inlet component support tab 355 can reduce size of first aperture 351 in the central panel 352 such that the seal of respiratory mask can be better supported within the front compartment 310. Reducing the size of the aperture 300 can provide better support for the mask in the front or first compartment 310 so that respiratory mask does not slip or push into the rear or second compartment 320. The lower strap slots 354 are angled to better retain the lower straps in an assembled state with respiratory mask frame. As shown in FIG. 19, bottom portion of each lower strap slots 354 extend from or near the elongated neck portion 355b of inlet component support tab 355 at an angle, projecting outwardly from the inlet component support tab 355. Each of the lower strap slots 354 are rounded at an outer end in order to reduce the likelihood of tearing. The first aperture 351 through which the headgear passes into the rear compartment (during packaging) is a substantially rectangular window as shown in FIGS. 18 and 19. This can further reduce the overall size of the first aperture 351 while maintaining the window for information display. The inlet component support tab 255 may form the inner edges of the lower strap slots 354 as shown in FIGS. 18 and 19.

As shown in FIG. 18, the carton 300 may include rear side flaps 371, 373 that may extend from lateral sides of the rear panel 316. Those rear side flaps 371, 373 may form side walls and better enclose rear/second compartment 320 during use. The rear side flaps 371, 373 can be substantially triangular. Although not shown in FIG. 18, the rear side flaps may include fastening features to secure them in a closed position. For example, tab(s) could insert into slot(s) in the central panel 312.

Figure 21:
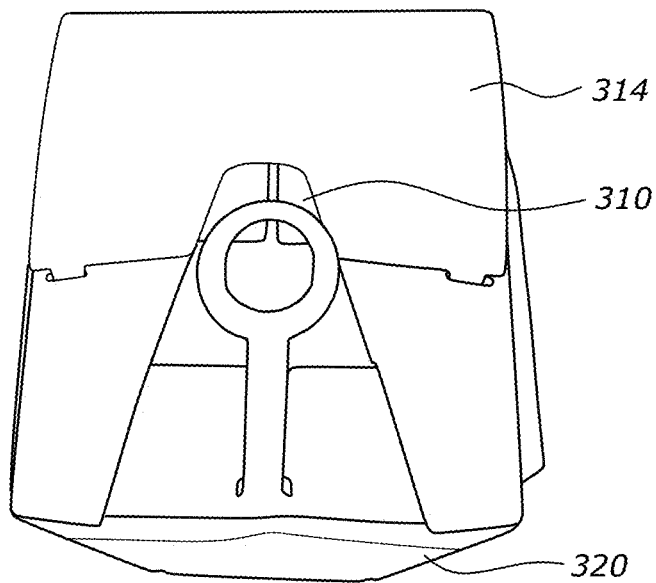
FIGS. 21-24 show the carton of FIG. 18 in closed configuration.
Figure 23:
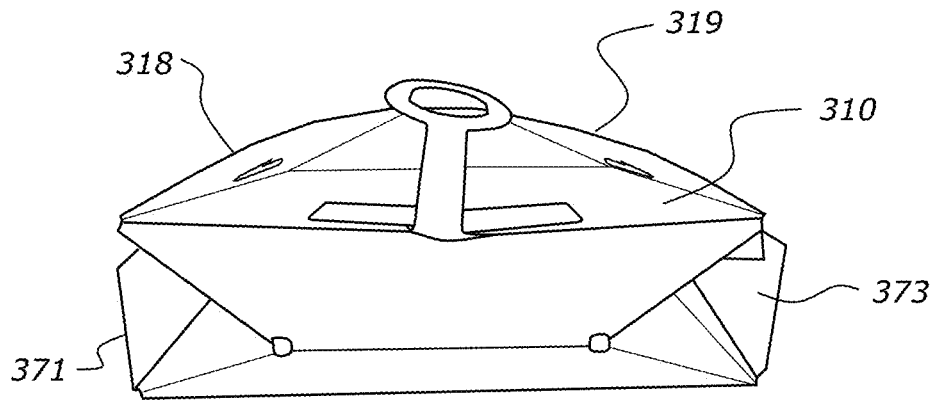
Figure 24:
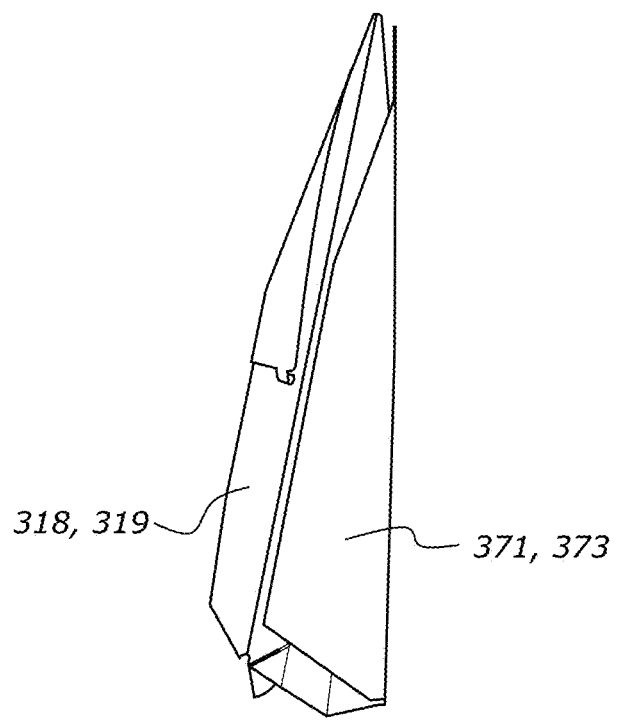

Also, as shown in FIG. 18, the carton may comprise a bottom panel 380 which may be hinged and disposed between the central panel 312 and the rear panel 314. The bottom panel 380 may be formed by folding the central panel 312 and the rear panel 316 along the laterally extending fold lines 381, 382 which may create a flat base that the carton 300 can stand upright on. The bottom panel 380 may comprise a horizontal fold line 383a that is parallel to the laterally extending fold lines 381, 382. Two diagonal fold lines 383c, 383d may extend from one of the two outermost edges of the bottom panel 380 to the horizontal fold line 383a at a junction 384a. Similarly, further two diagonal fold lines 383e, 383f may extend from another outermost edge of the bottom panel 380 to the horizontal fold line 383a at a junction 384b. As shown, circular holes 380a, 380b may be formed at or near the junctions 384a, 384b of the fold lines to reduce stress within the junction 384a, 384b and prevent tearing. Alternatively, instead of creating a flat base, the bottom panel 380 may be formed by folding the central panel 312 and the rear panel 316 along the laterally extending fold lines 381, 382 in a slightly bent manner as shown in FIGS. 21 and 23. A base that is flat or slightly bent can help to define more space/depth within the bottom of the rear compartment.

A fourth preferred embodiment of the invention will now be described.

This fourth embodiment relates to carton 400 (see FIG. 27) having at least two compartments, namely the front/first compartment 410 and a rear/second compartment 420. The carton 400 may be suitable for use in packaging an item namely, a respiratory mask.

Figure 27:
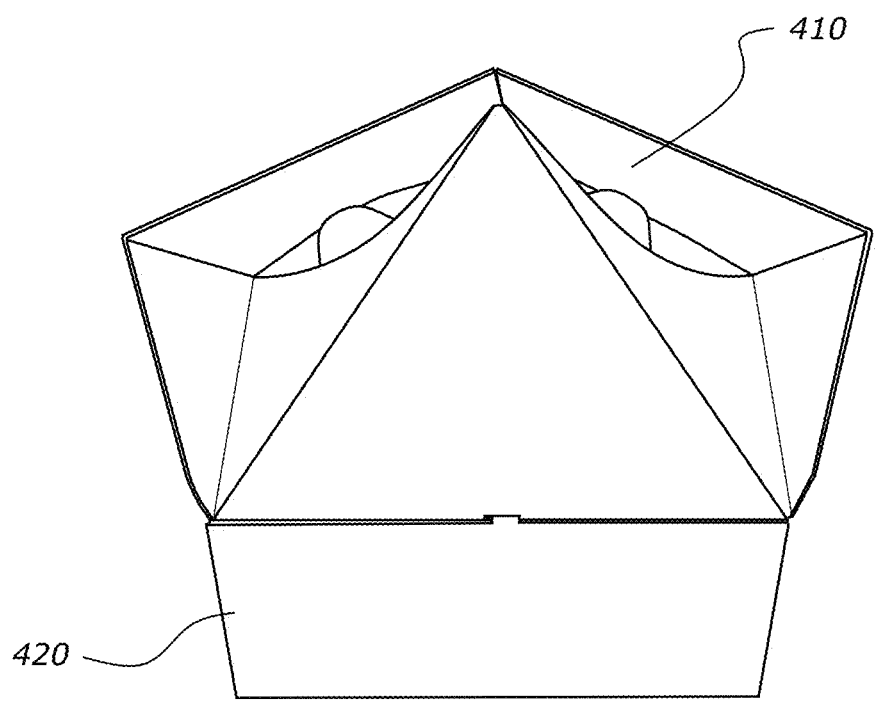

The carton 400 may basically comprises two nets punched from a sheet of cardboard that are folded to enclose and retain respiratory mask and any collateral such as user instructions. As shown in FIG. 27 and as mentioned above, when assembled, the carton may include two compartments 410, 420. The first compartment 410 may be adapted to contain respiratory mask and the second compartment 420 may be adapted to contain headgear, quick reference guide, user instructions and possibly spare respiratory mask components.

The first compartment 410 may be configured to be opened first to reveal respiratory mask and present information in stages. The second compartment 420 may be configured to be accessible from within the first compartment 410 once respiratory mask is removed. The carton may have a pentagonal shape when viewed end on as shown in FIG. 27. The second compartment can be trapezoidal in shape.

Figure 25:
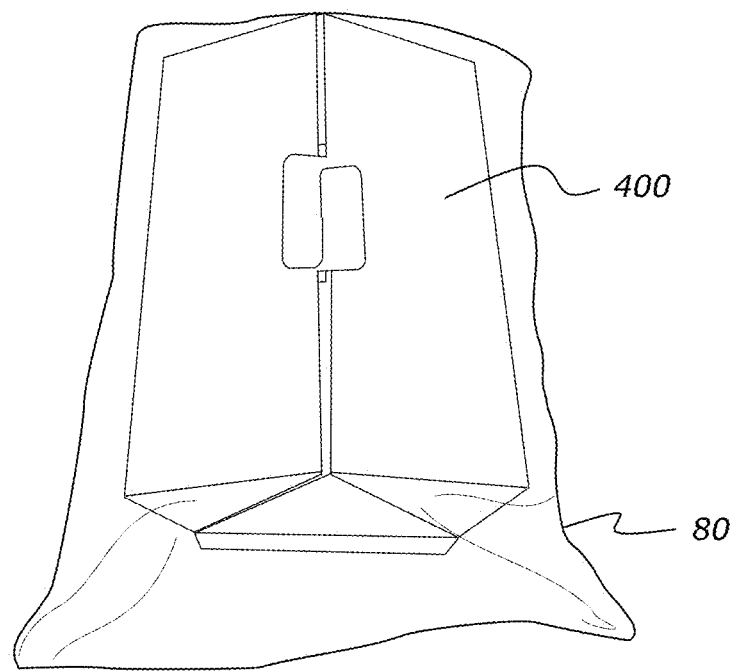
FIG. 25 shows a carton according to a fourth preferred embodiment of the present invention that may be packaged inside a bag, where the carton is assembled.

FIG. 25 shows how the carton 400 may be packaged inside a bag 80) during use. Although, it may be possible that carton 400 may also be packaged inside bag 10 described with previously.

As it can be from FIG. 25, the bag 80 may have no information on it. Information and branding may be provided on the carton 400 which may contain respiratory mask and other collateral.

One of the main purposes of the bag 80 can be to protect the mask from contamination and damage and keep the respiratory mask, instruction and any other collateral together during shipping.

Also, omitting the information from the bag 80, i.e. not printing or providing product information and instructions on the bag 80 may help to communicate to the user that the bag 80 is not intended to be kept and can be discarded or thrown away once respiratory mask and other collateral has been removed from within the bag 80. It can also make the bag 80 generic across all respiratory mask product lines, which can reduce parts and costs. Also, using a clear bag 80 can reduce cost than a printed bag.

Reference will now be made to FIGS. 28 to 30 to describe the carton 400 in more detail.

Figure 26:
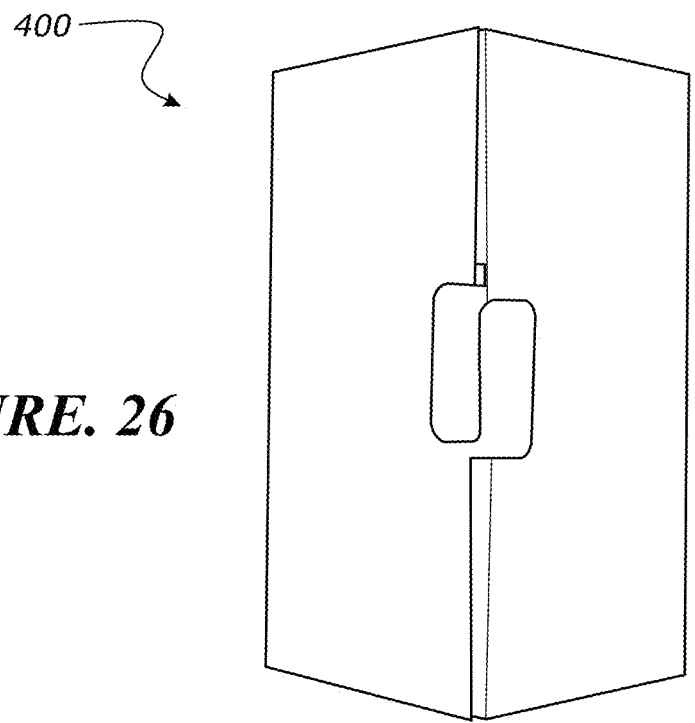
FIGS. 26-27 show a carton of FIG. 25 without the bag.

As shown in FIGS. 28 to 29, the carton 400 may comprise two separate sheets, preferably punched sheets of cardboard although many other suitable materials may be used. When assembled as shown in FIGS. 26-27, the carton 400 forms at least two compartments 410, 420 for use in packaging an item, namely a respiratory mask.

Referring to FIGS. 28-29, the two sheets may be a front/first compartment sheet 401 that is adapted to form a front or first compartment 410, and a rear/second compartment sheet 402 that is adapted to form a rear or second compartment 420.

Figure 36:
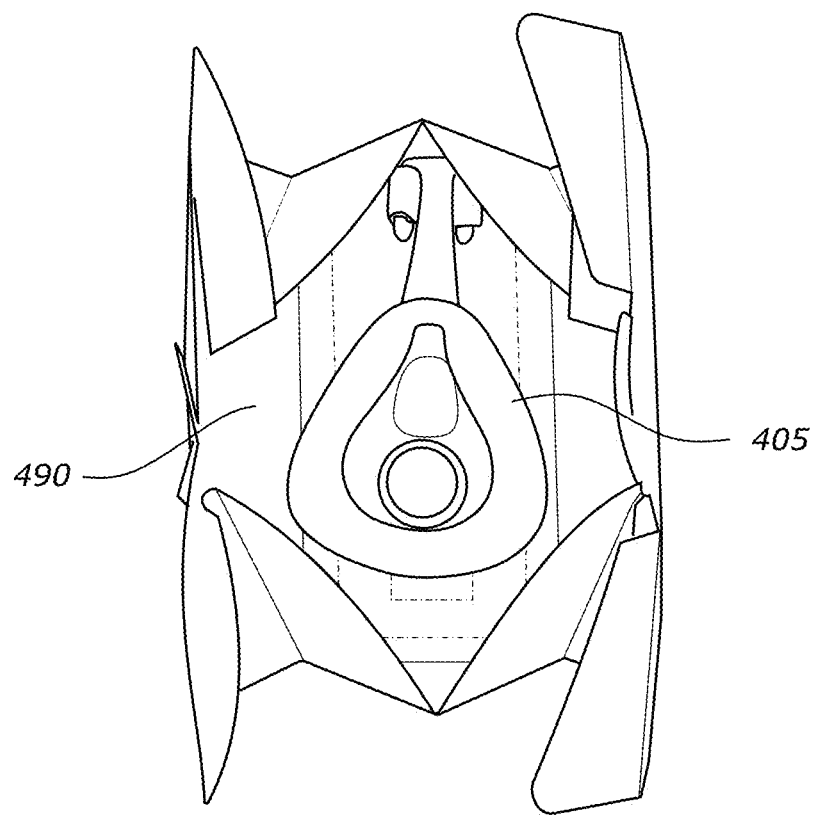

The first compartment sheet 401 may comprise an internal panel or internal wall or main panel 412 which is also called a central panel 412 that may be adapted to form a rear wall to the first compartment 410. As shown in FIG. 28, a first side panel 418 and a second side panel 419 may extend oppositely to each other from lateral sides of the central panel 412. Similarly, a first front flap 428 and a second front flap 429 may extend from the lateral sides of the first and second side panels 418, 419 respectively. The front compartment sheet 401 may also comprise a collapsible top flap 414 and a bottom flap 416. As shown with dashed lines in FIG. 28, the fold lines 417 may be include two vertical fold lines 417a, 417b that are spaced apart and parallel to each other and extend between the outermost edge of the top flap 414 to the outermost edge of the bottom flap 412. Similarly, as shown, the fold lines 417 may also include two horizontal fold lines 417c, 417d that are also spaced apart and are parallel to each other and extend between the outermost edge of the first front flap 428 to the outermost edge of the second front flap 429. Two spaced apart and vertical fold lines 417m, 417n are also formed between the central panel 412 and each of the side panels 418, 419 respectively as shown. Together these vertical fold lines define central panel 412 and side panels 418, 419. Further as shown, four diagonal fold lines 417e, 417f, 417g, 417h are formed in the top flap 414 and further four diagonal lines 417i, 417j, 417k, 417l are formed in the bottom flap 416. Specifically, the top flap 414 two V shaped fold lines are formed by the diagonal fold lines 417e, 417f, 417g, 417h and in the bottom flap 416, two V shaped fold lines are formed by fold lines 417i, 417j, 417k, 417l. The two V shaped fold lines in each of the top flap 414 and the bottom flat 416 are adjacent to each other so that they together form a W-shaped feature in each of the top and bottom flaps 414, 416 as shown. In each of the top flap 412 and the bottom flap 416, the two V shaped feature extend between the outermost edge of the respective flap 414, 416 to the horizontal fold line 417c, 417d that is proximal to the outermost edge of the respective flap 414, 416. The V shaped features do not extend beyond the vertical fold lines 417a, 417b as shown in FIG. 28. Having such a configuration of fold lines can allow the top flap 414 and a bottom flap 416 to be collapsible as shown in FIG. 36. The top and bottom flaps 414, 416 may be configured to fold to enclose a top portion and a bottom portion of the first compartment 410.

The second compartment sheet 402 may comprise a rear panel 432 that may be configured to form a rear wall. As shown in FIG. 29, a first side flap 438 and a second side flap 439 may extend from the lateral sides of the rear panel 432. A top flap 434 may extend from a top of the rear panel 432 and a bottom flap 436 may be located opposite to the top flap 434 extending from the bottom of the rear panel 432.

In use, the first compartment sheet 401 and second compartment sheet 402 may each comprise at least one fastening means that are configured to engage with each other to fasten the first and second compartments 410, 420.

The fastening means of the first compartment sheet 401 may comprise a plurality of fastener slots 440 that may be spaced around an edge of the central panel 412. Only one fastening slot 440 is shown in FIG. 28. Similarly, the fastening means of the second compartment sheet 402 may comprise a plurality of fastener tabs 441 that are spaced around the perimeter of the second compartment sheet 402. The plurality of fastener tabs 441 of the second compartment sheet 402 may be configured to engage with the plurality of fastener slots 440 on the first compartment sheet 401 to fasten the front/front and rear/second compartments 410, 420 together, during use.

The plurality of fastener slots 440 and the plurality of fastener tabs 441 can provide a friction fit. It can therefore be appreciated that no adhesives or permanent fasteners may be required for the carton 400 to remain in a closed configuration as shown in FIGS. 26-27.

As shown in FIG. 25, The carton 400 may be configured to be placed in a bag 80 as an insert.

The central panel 412 may include at least one respiratory mask retention feature 450 that is configured to retain a respiratory mask. Respiratory mask retention feature(s) 450 may comprise a plurality of features that are configured to retain a respiratory mask. Respiratory mask retention feature 450 can be located in a central location of the central panel 412.

Figure 31:
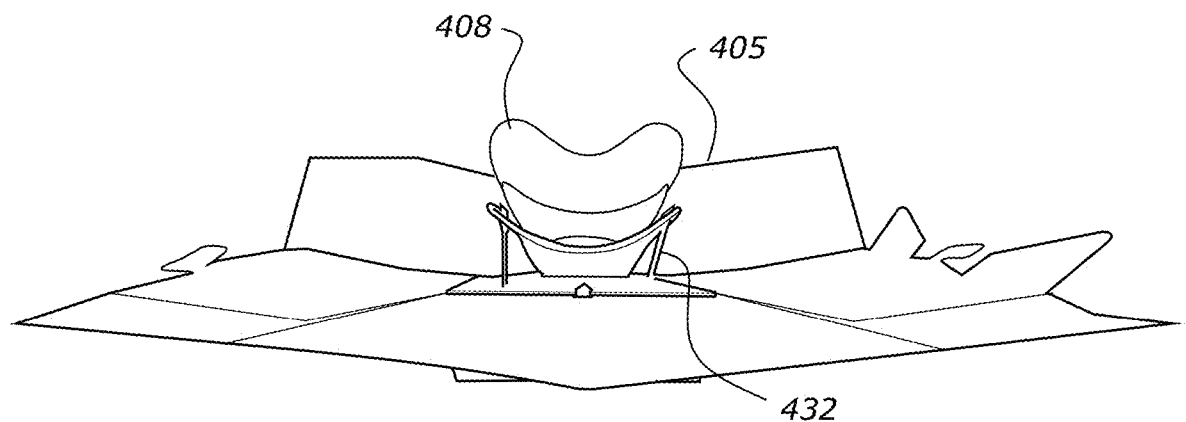
FIGS. 31-32 show retention features of the carton of FIG. 25.
Figure 32:
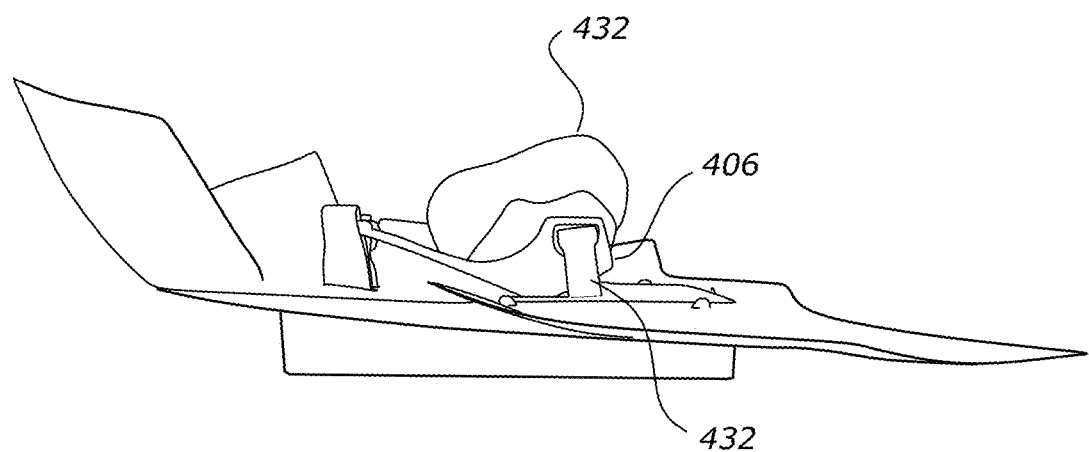
Figure 33:
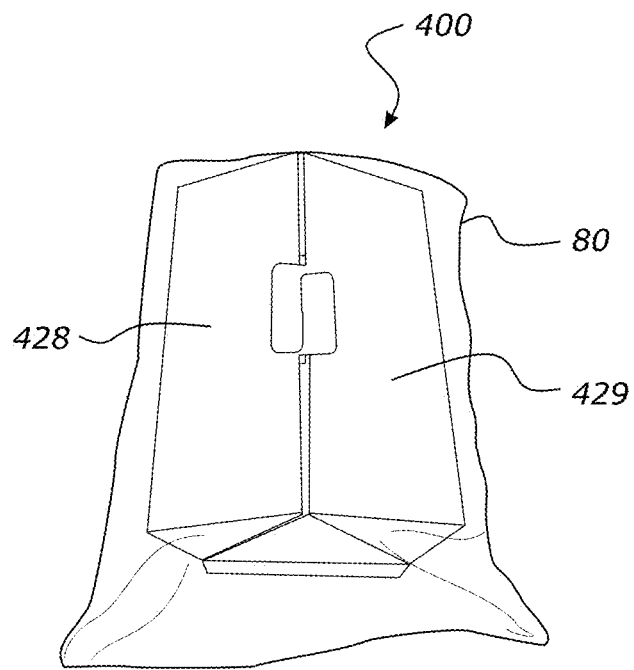
FIGS. 33-37 and 38A-38E show an example of a process of unpacking where the packaging system uses the carton of FIG. 25.

In this example, Respiratory mask retention feature 450 comprises a plurality of features to retain respiratory mask 405. See FIG. 31. As shown in FIG. 30, the mask retention feature 450 may comprise a cut-out 451 hereinafter referred to as an aperture 451 through which an inlet component such as elbow or inlet tube of a respiratory mask can pass, and retention arms/arms 432 that may be configured to be bent away from the central panel 412 to engage with a lower headgear of a respiratory mask frame 406. This is shown in FIGS. 31-32.

The frame 406 and the seal 408 of respiratory mask 405 may be configured to be fully enclosed within the front/first compartment 410 with the seal 408 facing the front. The headgear straps of respiratory mask can be attached to the frame 406 at one location (i.e. the forehead support).

Seal 408 of respiratory mask 405 may be presented towards the user so that the seal 405 is the first part of respiratory mask that is visible to the user when opening the carton. Alternatively, it may be positioned the other way around.

The central panel 412 may include a removable panel 434 (preferably including respiratory mask retention feature) that may be configured to be removed to detach respiratory mask 405.

The central panel 412 may comprise a perforated feature 433 or a perforated line that defines the removable panel 434 and may enable the removable panel 434 to be removed from the central panel 412.

The removable panel 434 may comprise a finger grip region 435 to provide a means for gripping the removable panel. Finger grip region 435 is sized and shaped to be readily gripped by a user, and may be a circular or polygonal tab foldably attached to removable panel 434. Alternatively, the circular or polygonal tab of the finger grip region 435 may comprise a perforated perimeter such that it can be pushed through into the second compartment 420 to form an aperture through which a user's finger can be inserted to grip the removable panel 434.

As shown in FIG. 28, the first and second front flaps may include interlocking means such as fastener tabs 446 adapted to interlock and secure the front compartment 410 in a closed configuration.

The interlocking means may comprise closure tabs 447 extending from an edge of one of the front flaps. As shown in n FIG. 28, the closure tabs 447 may extend from an edge of the second front flap 429. The closure tabs 447 are configured to be overlapped by the first front flap 428 when in the closed configuration.

The rear wall formed by the rear panel 402 may include information such as but not limited to manufacturing, traceability and legal information.

One example of a process of unpacking the packaging system that uses the fourth preferred embodiment of the carton 400 will now be described with reference to FIGS. 33-37 and 38a-38e.

Figure 34:
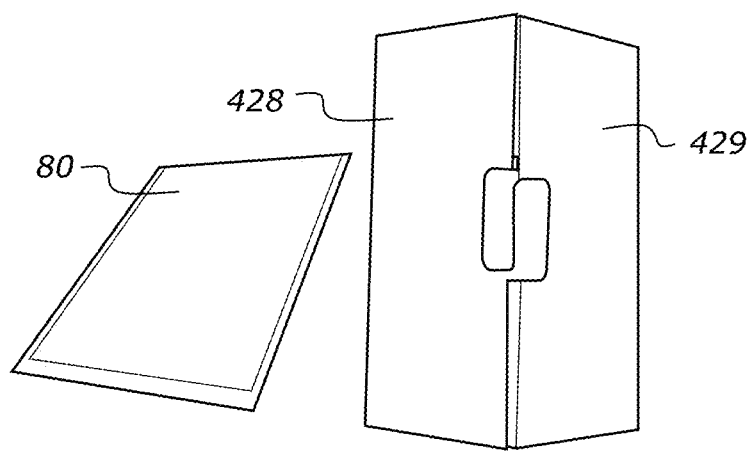
Figure 35:
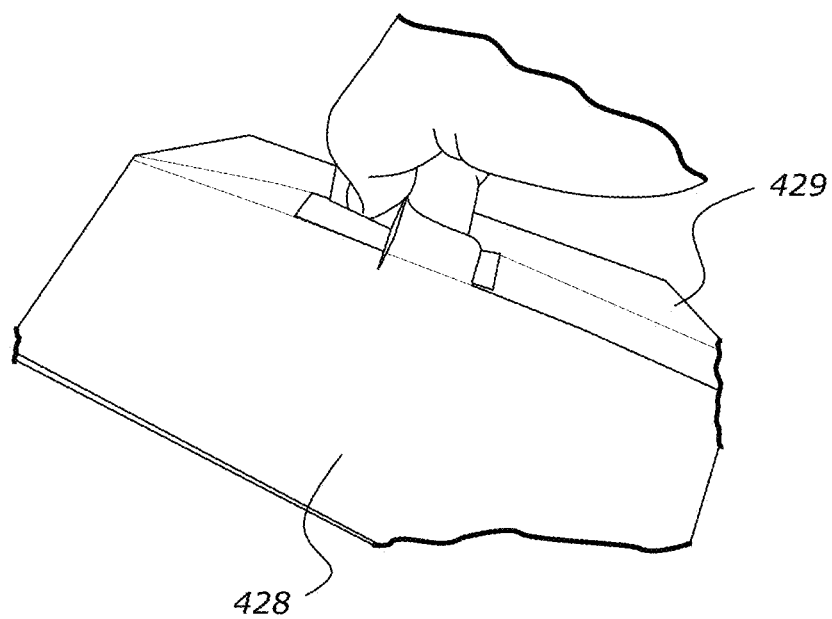
Figure 37:
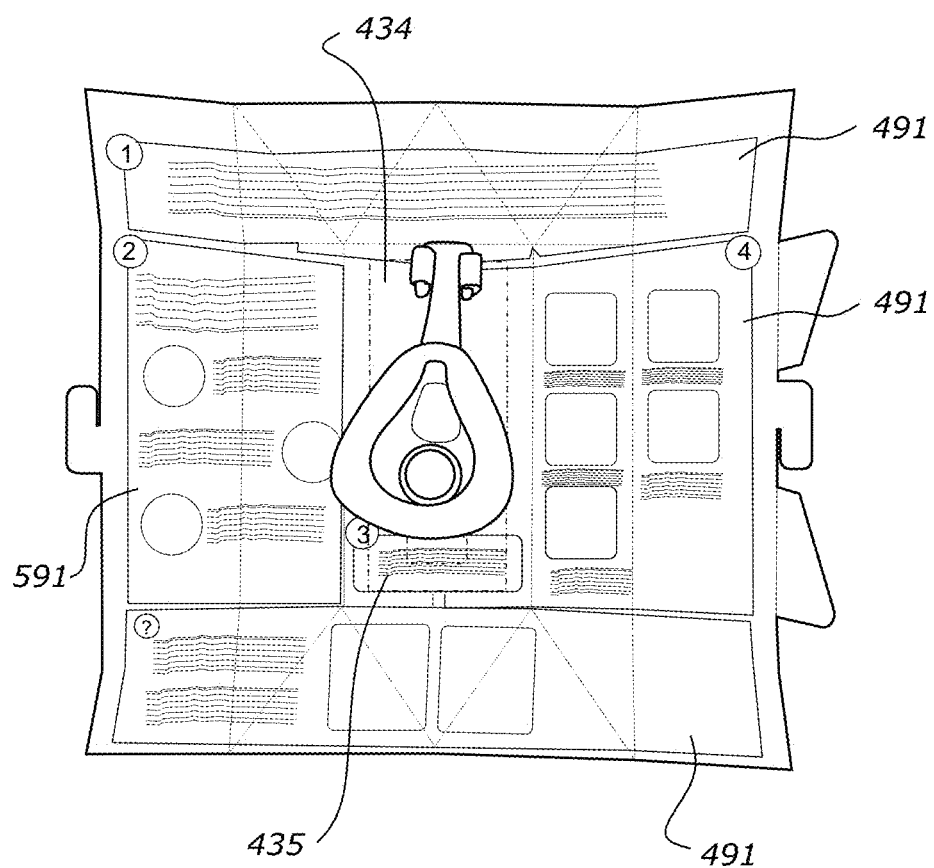
Figure 38A:
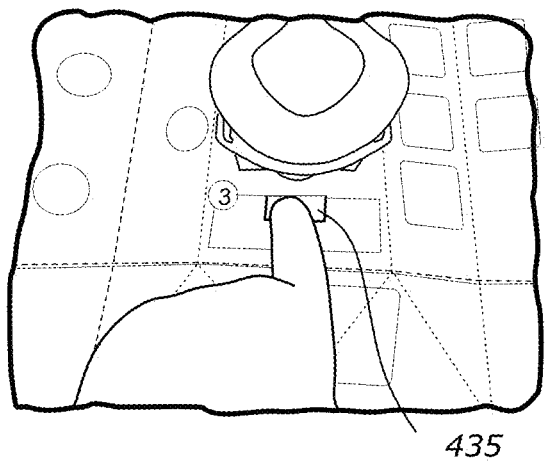
Figure 38B:
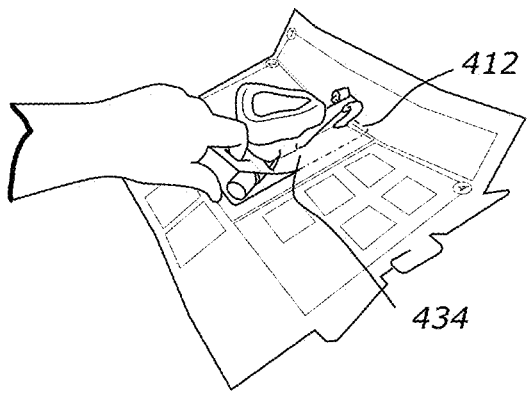
Figure 38C:
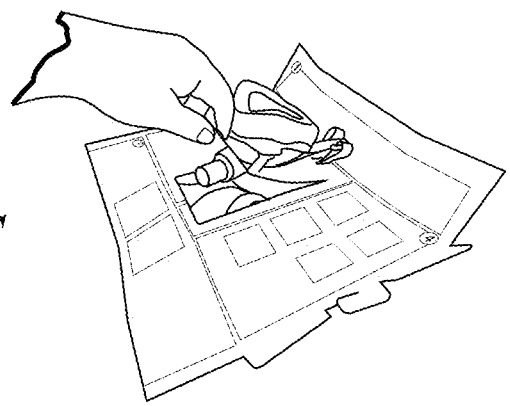
Figure 38D:
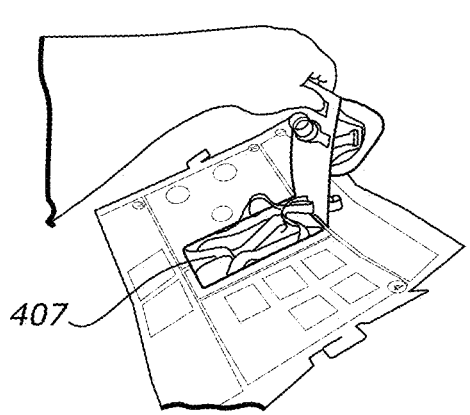
Figure 38E:
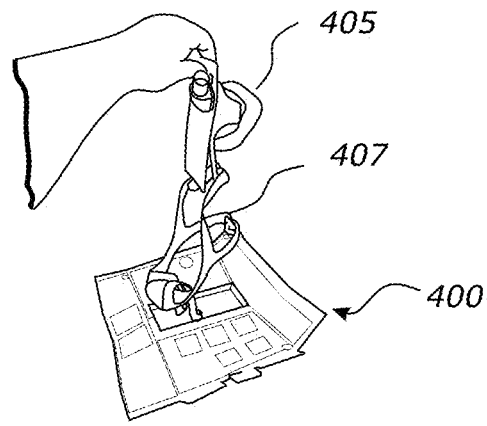

The following steps may be performed for unpacking where the packaging system uses carton 400:
1. Remove box/carton 400 from bag as shown in FIG. 34. Once, this step is performed, the bag 80 may be discarded as it contains no further information.
2. Release fasteners to open front flaps 428, 429 of front compartment 410 as shown in FIG. 35. Performing this step will reveal respiratory mask 405 and a quick reference guide 490 as shown in FIG. 36.
3. Front compartment 410 is opened out flat to present information blocks 491 that are arranged around respiratory mask as shown in FIG. 37. The information blocks 491 may be arranged around the respiratory mask in an order that is intuitive to follow such that the information is presented to the user in a staged and/or paced order.
4. Once the user has read all the quick reference information or is ready, respiratory mask 405 can be removed from the box/carton by:
   a. Pushing the finger grip region 435 through into the rear compartment to form an aperture (see FIG. 38A)
   b. Inserting finger through the finger grip aperture and lifting/tearing the removable panel 434 from the central panel 412 (see FIGS. 38B-38D)
   c. Lifting the respiratory mask 405 to remove the headgear 407 from the rear/second compartment 420 (see FIG. 38D)
   d. Removing the respiratory mask 405 from the retention feature in the removable panel (see FIGS. 38D and 38E).
   e. Removing the quick reference guide and/or any other item from the rear compartment. The carton 400 may then be discarded.

FIGS. 39A, 39B, 39C, 40A, 40B and 40C show an example/embodiment of a packaging carton 500 according to a fifth preferred embodiment of the present invention.

Figure 39A:
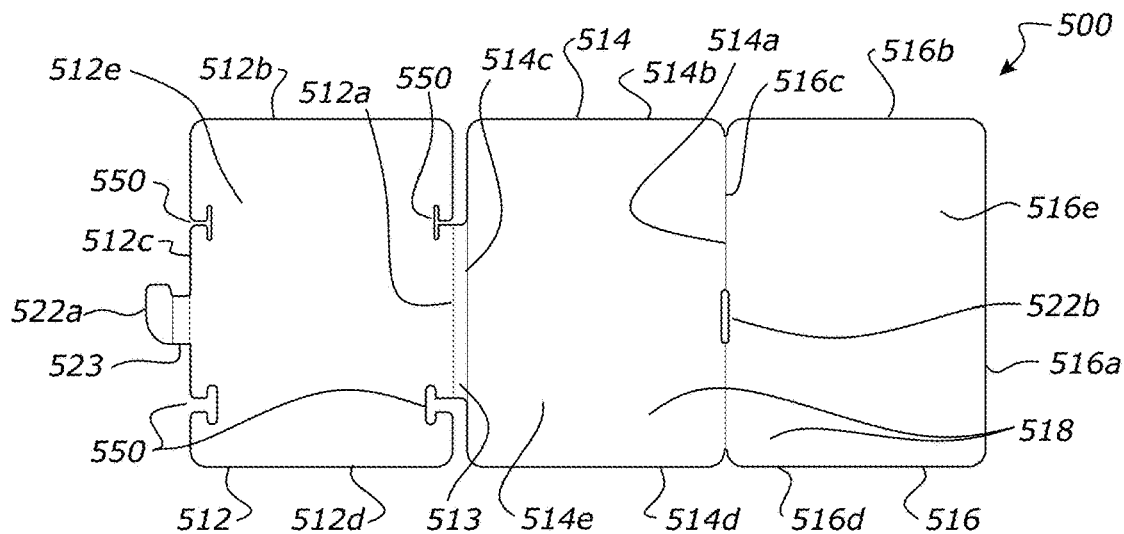
FIG. 39A shows a carton according to a fifth preferred embodiment of the present invention that may be packaged inside a bag, where the carton is in an open position with the front surfaces of the panels of the cartons shown.
Figure 39B:
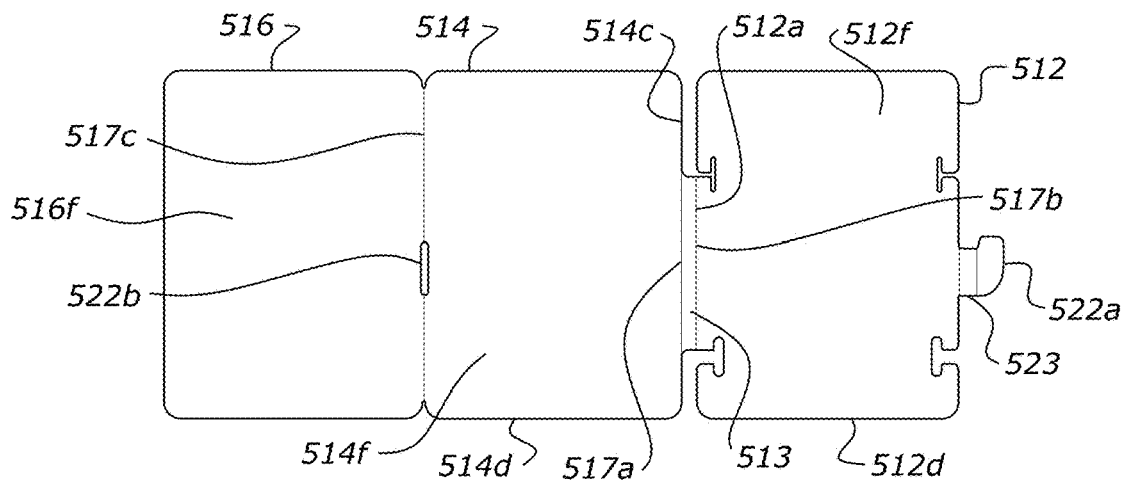
FIG. 39B shows the rear surfaces of the panels of the carton of FIG. 39A in the open position.

FIG. 39A shows front surfaces 512e, 514e, 516e of the carton 500 comprising three panels 512, 514 and 516. Panels 514 and 516 are formed as a flap 518 that is hinged to the panel 512. Similarly, FIG. 39B shows rear surfaces 512f, 514f, 516f of the carton 500 comprising three panels 512, 514 and 516. In FIGS. 39A and 39B, the carton 500 is shown in an open position.

As shown in FIGS. 39A and 39B, first panel 512 of the carton 500 is a central panel 512 for the carton 500. The central panel 512 acts as a main panel from which the second and third panels 514, 516 depend. As it can be seen from FIGS. 39A, 39B the central panel 512 as referred herein is not located at the centre of the carton 500. The panel 512 is referred to as the central panel 512 because it is the primary/main panel for mask retention. As shown in FIGS. 39A and 39B, the central panel 512 has a respiratory mask retaining feature 550 that is configured to retain the respiratory mask 505 to the central panel 512. The carton 500 may comprise a flap 518 extending from an edge of the central panel 512. The flap 518 may be configured to be folded towards the central panel 512 and over at least a portion of the respiratory mask (in this case a folded over a headgear of the respiratory mask) in a closed configuration. Similarly, the flap 518 may be configured to be folded away from the central panel in an open configuration as shown in FIGS. 39A and 39B. The respiratory mask retaining feature 550 may be configured to retain the respiratory mask to the central panel when the flap is in either an open position (as shown in FIGS. 39A, 39B, 40B and 40C) or a closed position as shown in FIG. 40A.

The carton 500 is formed of a sheet material, preferably a cardboard or a punched sheet of cardboard.

Unlike the cartons described in the previous embodiments that folds to form two compartments, carton 500 of this fifth preferred embodiment folds to form only one or a single compartment, i.e. compartment 510 that is adapted to contain headgear assembly or headgear 507 of the respiratory mask 505. The flap 518 and consequently the compartment 510 are configured to be opened first to reveal the headgear 507 of the respiratory mask 505 and present information in sequential order or stages. The sequential order may be predetermined by the manufacturer/supplier of the respiratory mask 505. The compartment 510 is configured to be accessible from at least one side of the central panel 512.

The carton 500 is formed of a sheet material that is configured to form a single compartment 510 for use in packaging an item such as respiratory mask 505.

As shown in FIG. 39A, the central panel 512 is an external panel having at least a first side 512a, a second side (top side) 512b, a third side 512c and a fourth side (bottom side) 512d. The central panel 512 also has a front surface 512e and a rear surface 512f. As shown in FIG. 39A, the first side 512a is a first edge, the second side 512b is the second edge, the third side 512c is the third edge and the fourth side 512d is the fourth edge of the central panel 512.

The flap 518 is hinged and extends from the first side 512a of the central panel 512. The flap 518 comprises or is formed of two panels, namely the second panel 514, referred to hereinafter as an intermediate panel 514 the third panel 516, referred to hereinafter as a rear panel 516.

The intermediate panel 514 may have at least a first side 514a, a second side (top side) 514b, a third side 514c and a fourth side (bottom side) 514d. The intermediate panel 514 also has a front surface 514e and a rear surface 514f. As shown in FIG. 39A, the first side 514a is a first edge, the second side 514b is the second edge, the third side 514c is the third edge and the fourth side 514d is the fourth edge of the intermediate panel 514.

The rear panel 516 may have at least a first side 516a, a second side (top side) 516b, a third side 516c and a fourth side (bottom side) 516d. The rear panel 516 also has a front surface 516e and a rear surface 516f. As shown in FIG. 39A, the first side 516a is a first edge, the second side 516b is the second edge, the third side 516c is the third edge and the fourth side 516d is the fourth edge of the rear panel 516.

The intermediate panel 514 is hinged and extends from the first side 514a of the central panel 512 via a spacer 513 discussed later. Similarly, a rear panel 516 is hinged and extends from the intermediate panel 514, specifically from the first side 514a of the second panel which is opposite to the third side 514c of the intermediate panel 514.

Figure 39C:
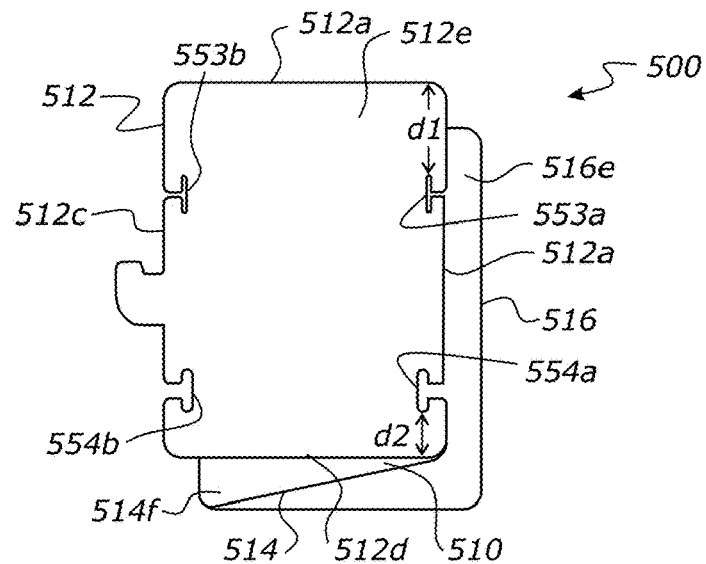
FIG. 39C shows the carton of FIG. 39A in a partially closed or collapsed or folded condition.

When the carton 500 is in a closed configuration as shown in FIG. 40A, the rear panel 516 may be configured to be folded over the front surface 514e of the intermediate panel 514 or in a first direction so that the front surface 514e of the intermediate panel 514e and the front surface 516e of the rear panel face each other. Similarly, the central panel 512 may be configured to be folded over the rear 514f surface of the intermediate panel 514 so that the rear surface of the central panel 512 faces the rear surface 514f of the intermediate panel 514. Therefore, the carton 500 may folded as Z-fold/accordion fold as shown in FIG. 39C. As shown in FIG. 39C, when folded, the central panel 512 becomes the front panel. Of course, many other suitable ways of folding the carton 500 may be possible. As shown, the overall size of the panels 512, 514, 516 are same or substantially the same and each of the panels 512, 514, 516 are generally rectangular in shape preferably with rounded corners. Rounded corners help to prevent curling. Also, since the corners are rounded and not sharp corners, that can help prevent puncturing or damaging of a bag (e.g. a plastic bag) when the carton 500 is inserted or packaged inside such a bag.

As shown in FIG. 39B the carton 500 may comprise fold lines 517a, 517b, 517c. The fold lines 517a, 517b, 517c may allow the panels 512, 514, 516 to be hinged. The fold lines 517a, 517b, 517c may be formed vertically as shown in FIG. 39B. As shown, a spacer 513 may be located between the central panel 512 and the intermediate panel 514, specifically between the first side 512a of the central panel 512 and the third side 514c of the intermediate panel 514. The spacer 513 may be of a rectangular or a substantially rectangular shape and the central panel 512 and the intermediate panel 514 are connected to each other by the spacer 513. The height of the spacer 513 may be smaller than the height of the central panel 512 and the intermediate panel 514. For example, the height of the spacer 513 may be at least half the height of the central and intermediate panels 512, 514. The height of each of the panels 512, 514, 516 may be approximately 235 mm. The spacer 513 may be located more proximal to the fourth sides of the central panel 512 and the intermediate panel 514 than the second sides of the central panel 512 and the intermediate panel 514. Fold lines 517a, 517b are vertically formed on two sides of the spacer 513. The spacer 513 allows spacing between the central panel 512 and the intermediate panel 514. Such spacing between the panels 512, 514 makes the packaging protrude to give the packaging a more appealing profile, i.e. a box shaped profile. The fold line 517c may be vertically formed between the intermediate panel 514 and the rear panel 516 as shown.

The compartment 510 may be configured to be partially enclosed. For example, the compartment 510 may be configured to be open at least at one edge such as a top edge and a bottom edge.

The central panel 512 may comprise at least one panel retention feature and the fold line 517c located between the intermediate panel 514 and the rear panel 516 may comprise at least one complementary feature that is adapted to engage with the panel retention feature thereby allowing the intermediate panel 516 and the central panel 512 to be fastened together.

As shown in FIGS. 39A and 39B, the panel retention feature can be in the form of a retention tab 522a that is adapted to be received by complementary feature in the form of a retention slot 522b. The retention slot 522b is formed at a portion of the fold line 517c and is located at the same height as the retention tab 522a. As shown, a retention tab spacer 523 that is rectangular or substantially rectangular in shape connects the retention tab 522a with the central panel 512. More specifically, retention tab spacer 523 connects the retention tab 522a with the third side 512c of the central panel. The retention tab spacer 523 is orthogonal to the retention tab 522a and provides spacing between the retention tab 522a and the central panel 512. The retention tab 522a together with the retention tab spacer 523 form a hook shaped or substantially hook shaped feature as shown.

The central panel 512 may include a respiratory mask retaining feature 550 that is configured to retain respiratory mask 507. The respiratory mask retaining feature 550 may comprise a plurality of features or geometries that are configured to work together retain respiratory mask 505 to the carton 500.

As shown in FIG. 39C, the central panel may comprise a respiratory mask retaining feature 550 in the form of a plurality of (preferably four) cut-outs, namely upper cut-outs 553a, 553b and lower cut-outs 554a, 554b. The cut-outs 553a, 553b, 554a, 554b may be configured to receive and optionally frictionally retain straps of respiratory mask 505 or more preferably, straps of a headgear 507 of respiratory mask 505 as shown in FIG. 40A. The cut-outs 553a, 553b, 554a, 554b are in the form of slots. Each of the cut-outs is T-shaped in the embodiment shown in FIG. 39C.

One upper cut-out 553a and one lower cut-out 554a are spaced apart from each other at a distance and extend from the first side 512a of the central panel 512 in a direction that is towards the third side 512c of the central panel 512 but terminate at about a quarter of the total distance from the first side to the centre of the central panel 512. Similarly, another upper cut-out 553b and another lower cut-out 554b are also spaced apart from each other at a distance and extend from the third side 512c of the central panel in a direction that is towards the first side 512a of the central panel 512 but terminate at about a quarter of the total distance from third side to the centre of the central panel 512. The distance between the upper cut-out 553a and the lower cut-out 554a is same or substantially the same as the distance between the upper cut-out 553b and lower cut-out 554b. When viewed from a first side 512a of the central panel 512 towards the third side 512c of the central panel 512, the cut-outs 553a,554a are T-shaped and the other two cut-outs 553b, 554b are inverted T-shaped. The upper cut-outs 553a, 553b are located at a distance d1 from the top side (i.e. second side 512a) the central panel 512 and the lower cut-outs 554a, 554b are located at a distance d2 from the bottom side (i.e. fourth side 512d) of the central panel 512. Preferably, distance d1 is greater than the distance d2. The spacer 513 as described above extends lengthwise along the first side 512a of the central panel 522 between the upper cut-out 553a and lower cut-out 554b.

To secure the respiratory mask 505 to the carton 500, the mask 500 is placed on the front surface 512e of the central panel 512 and straps of the headgear 507 are inserted into the cutouts 553a, 553b 554a, 554b. Specifically, the upper straps 507a are inserted into upper cutouts 553a, 553b and the lower straps 507b are inserted to the lower cutouts 554a, 554b as shown in FIG. 40A. T-shaped cut-outs 553a, 553b, 554a, 554b provide a retention feature to prevent the straps 507a, 507b from falling out of the cut-outs 553a, 553b, 554a, 554b. As shown in FIGS. 39A to 39C, the upper cut-outs 553a, 553b for the upper straps 507a may be smaller and narrower than the lower cut-outs 554a, 554b for the lower straps 507b. This is because, in this example, the lower cut-outs 554a, 554b are to receive and retain folded sections of the lower straps 507b whereas the upper cut-outs 553a, 553b are to receive and retain non-folded sections of the upper straps 507a. Since the folded sections have increased thickness as compared to the non-folded sections, the lower cut-outs 554a, 554b into which the folded sections are to be inserted and retained needs to be larger and wider than the upper cut-outs 553a, 553b into which non-folded sections of the upper straps 507a are to be inserted and retained. However, depending upon the thickness of the headgear straps or the portions of the headgear straps that are to be inserted into and retained, the size of the upper cutouts 553a, 553b may of same, smaller or larger than the size of the lower cutouts 554a, 554b.

The positioning and shape of any retention features above may be varied to suit any respiratory masks that require packaging.

From the above, it can be appreciated that no adhesives or permanent fasteners may be required for the carton 500 to remain in a closed configuration as shown in Figures. In alternative embodiments, it may be desirable to seal the carton, such as with adhesive or mechanical fasteners (for example, pins, clips, or staples).

Each of the central panel 512, intermediate panel 514, rear panel 516 may provide space for printing information or instructions for the user. The instructions can be any instructions such as but not limited to first set-up instructions, fitting instructions, mask parts information, cleaning instructions, mask parts replacement instructions, and additional support information. The information may also be manufacturing, traceability and legal information. It may also contain a machine-readable code e.g. a Quick Response code (QR code) that can be scanned by a suitable device such as a smartphone camera to translate to useful information such as displaying a text to the user, opening a URL etc.

In summary, insert or carton 500 may include three foldable panels 512, 514, 516, each having a front surface 512e, 514e, 516e and a rear surface 512f, 514f, 516f, therefore a total of six surfaces. The central panel 512 may retain the mask 505 and can be folded over an adjacent panel, i.e. intermediate panel 514 to form a compartment 510 that may be adapted to contain the headgear 507 of the mask 505. At least one or each of the six surfaces may contain printed information 515 or instructions for the user. The retention tab 522a may be configured to be opened/released from the retention slot 522b to reveal the inner surfaces and present printed information in stages. The retention tab 522a may prevent the carton 500 from unfolding and may maintain the compartment 510 for the straps 507a, 507b of the headgear 507 to be retained. The item retaining feature that is a respiratory mask retaining feature 550 may comprise a plurality of slots/cut-outs namely upper cut-outs 553a, 553b and lower cut-outs 554a, 554b that can receive and frictionally retain the straps of the headgear 507. The rear panel 516 may fold or unfold without the need to remove/release the retention tab 522a from the retention slot 521a and also without the need to remove the mask 505. The compartment 510 is formed by the central panel 510 folding in a direction towards the intermediate panel 514, and by inserting the retention tab 522a that is connected to the central panel 512 into the retention slot 522b located at a fold line 517 formed between the intermediate panel 514 and the rear panel 516. The compartment 510 is partially enclosed and can be opened along a top and a bottom edge. The mask 507 is secured onto the central panel 512 by feeding the headgear straps 507a, 507b behind the central panel 512 into the compartment 510 through the cutouts 553a, 553b, 554a, 554b located at the central panel 510. Cushion module and the frame of the respiratory mask 505 are supported on the front surface 512a of the central panel 512. The shape and positioning of the cutouts 553a, 553b, 554a, 554b can be varied to suit any respiratory mask that requires packaging.

The packaging carton 500 as described in the fifth preferred embodiment includes several advantages. The surface area of the cardboard to make the carton 500 can be reduced as the carton 500 only contains a single compartment. The carton 500 is easy to assemble and disassemble. The structure is less susceptible to damage which means that thinner cardboard may be used, and such thinner carton may still be sufficient to maintain packaging structure. The design is simple and provides sufficient space at the surface of the panels 512, 514, 516 for presenting information to the user thereby minimising the need of extra components such as a quick reference guide. The information may be presented in a sequential order. Since, the headgear 507 can be attached to the mask assembly but is hidden until the mask 505 is removed from the carton 500, that can help prevent any confusion and tangling or disassembly.

Figure 41:
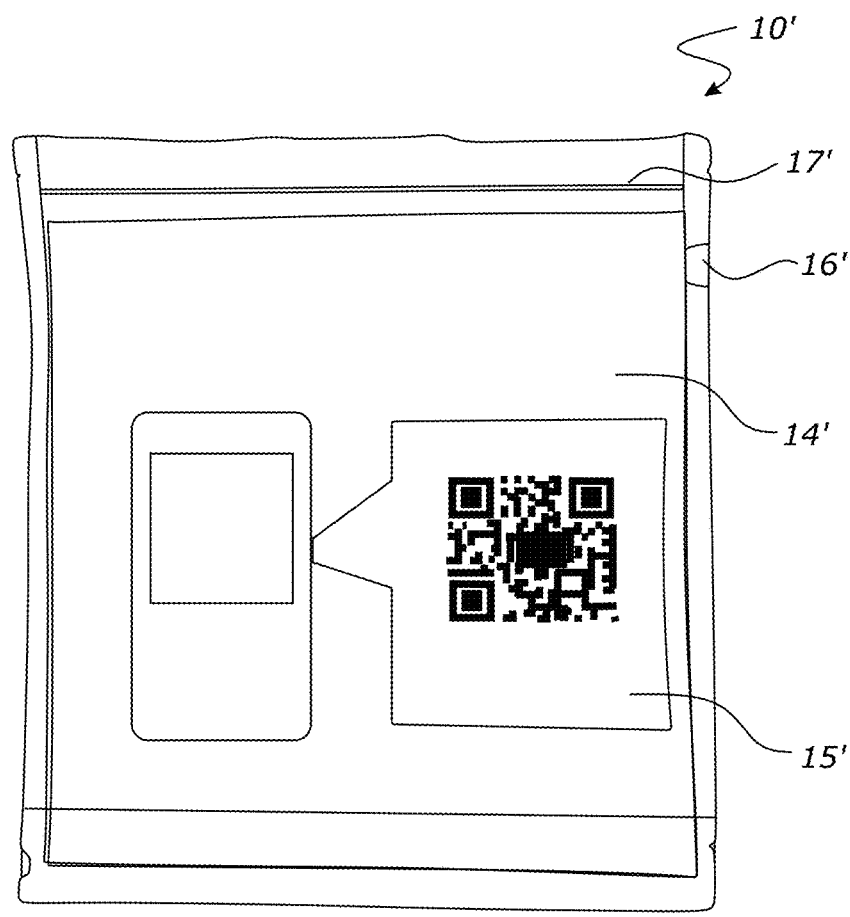
FIG. 41 shows a side elevation view of another preferred embodiment of a bag that can be used in a packaging system according to the present invention.

The carton 500 may be configured to be placed in a bag as an insert. Although, any suitable bag may be used, FIG. 41 shows an example of one preferred embodiment of the bag 10' that is suitable for placing the carton 500 inside the bag as an insert. Bag 10' may be disposable but can be made from a material that is recyclable, biodegradable and/or compostable. The bag 10' may not provide any information that the user requires to set-up and use the contained product. Bag 10' may have an expandable base to allow it to stand on a shelf. Base of the bag 10' may comprise gusset formation. There may be no heat sealing on the bottom corners of the gusset formation. Bag 10' can protect items such as respiratory mask from contamination and damage during shipping. Reducing the information on bag 10', i.e., removing product information and instructions, may help to communicate to the user that bag 10' is not intended to be kept and can be thrown away once the item and other collateral has been removed from within bag 10'. A rectangular viewing window may be provided. The front or rear wall of the bag 10' or at least a portion of the front or rear wall may be covered with a sticker/label 14'. The sticker/label may comprise minimal information 15' on it other than regulatory, manufacturing or legal information and possibly generic branding information. The sticker/label may contain a machine-readable code e.g. a Quick Response code (QR code) that can be scanned by a suitable device such as a smartphone camera to translate to useful information such as displaying a text to the user, opening a URL etc.

As shown in FIG. 41, the bag 10' is wider than bag 10 described in FIG. 1. A closure means such as a zip lock 17' may be provided at the opening. The bag 10' may be laser scored at the top which allows it to be easily opened in straight line. Air outlet 16' may be present in the bag 10' preferably underneath the closure means.

Figure 42:
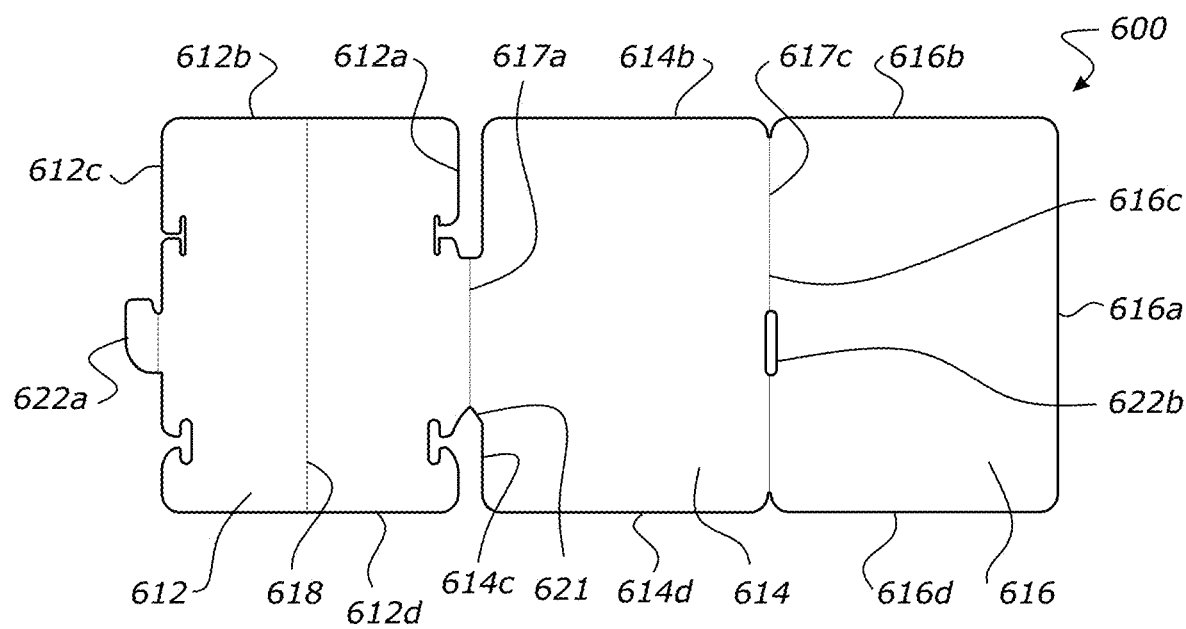
FIG. 42 shows a carton according to a sixth preferred embodiment of the present invention that may be packaged inside a bag, where the carton is in an open position with the front surfaces of the panels of the cartons shown.

FIG. 42 shows an example/embodiment of a carton 600 according to second preferred embodiment of the present invention in an open configuration.

The carton 600 of this sixth preferred embodiment is substantially the same as the carton 500 as described above in the fifth preferred embodiment with some variations which can be identified by comparing FIGS. 39A, 39B and 39C with FIG. 42. In FIG. 42 the features that are similar to those shown in FIGS. 39A, 39b, 39C are identified with the same reference numeral, incremented by 100. Most of the description of the carton 500 of the fifth preferred embodiment, equally applies to the carton of the sixth preferred embodiment and therefore, only the variations will be discussed.

As shown, a fold line 618 is formed along the centre of the central panel 612 extending vertically from the top to the bottom of the central panel 612, i.e from the second side 612a to the fourth side 612d of the central panel 612. The retention tab spacer is not provided in this embodiment, which means there is no space located between the retention tab and the central panel 612. Also, since the spacer 613 only includes only a single fold line 617a at the centre, there will be no box shaped profile when the central panel 612 is folded over the intermediate panel and the retention tab 622*a* is inserted inside the retention slot 622*b*, and instead the profile will be a curve shape profile.

The retention slot 622*b* may be larger in size as compared to the retention slot 522*b* of the previous embodiment. The increase in size in the retention slot 622 is to allow more room for insertion of the retention tab 622*a* whose overall length may be larger than that of the retention tab 522*a* of the previous embodiment. Also, the retention slot 622*b* may extend slightly to the rear panel 616 rather than being symmetrically formed along the fold line.

The height of each of the three panels 612, 614 and 616 is preferably about 235 mm and the length of the carton 600 in the fully extended/open position as shown in FIG. 42 is preferably about 566 mm.

At least the bottom portion of the spacer 613 may preferably comprise a triangular cut 621 in order to eliminate the presence of sharp edge when the central panel 612 is folded over the intermediate panel 614 or vice versa.

The inlet portions 653*a*', 653*b*', 653*c*', 653*d*' of the slots or T-shaped cutouts 653*a*, 653*b*, 654*a*, 654*c* may be rounded and are opened up for aesthetic reasons as well as for facilitating easy insertion of the headgear straps.

FIGS. 43A to 43B and 44A to 44D show an example/embodiment of a packaging carton 700 according to a seventh preferred embodiment of the present invention.

Figure 43A:
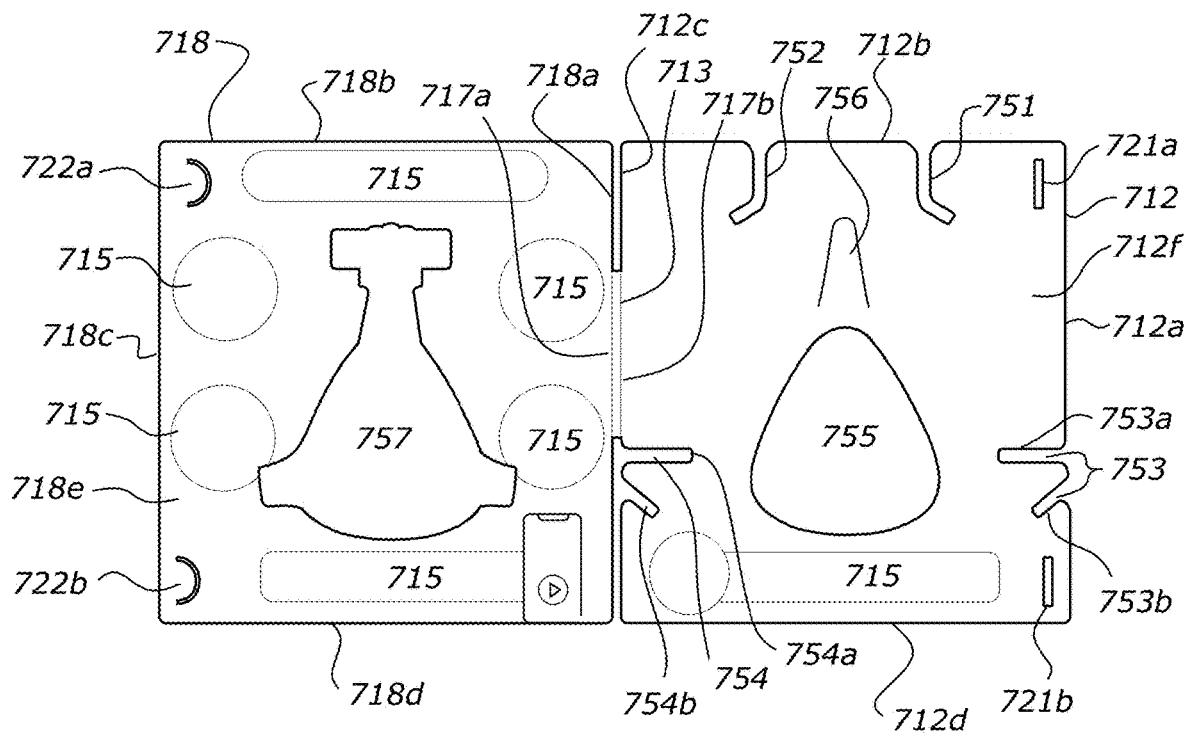
FIG. 43A shows a carton according to a seventh preferred embodiment of the present invention that may be packaged inside a bag, where the carton is in an open position with the front surfaces of the panels of the cartons shown.
Figure 43B:
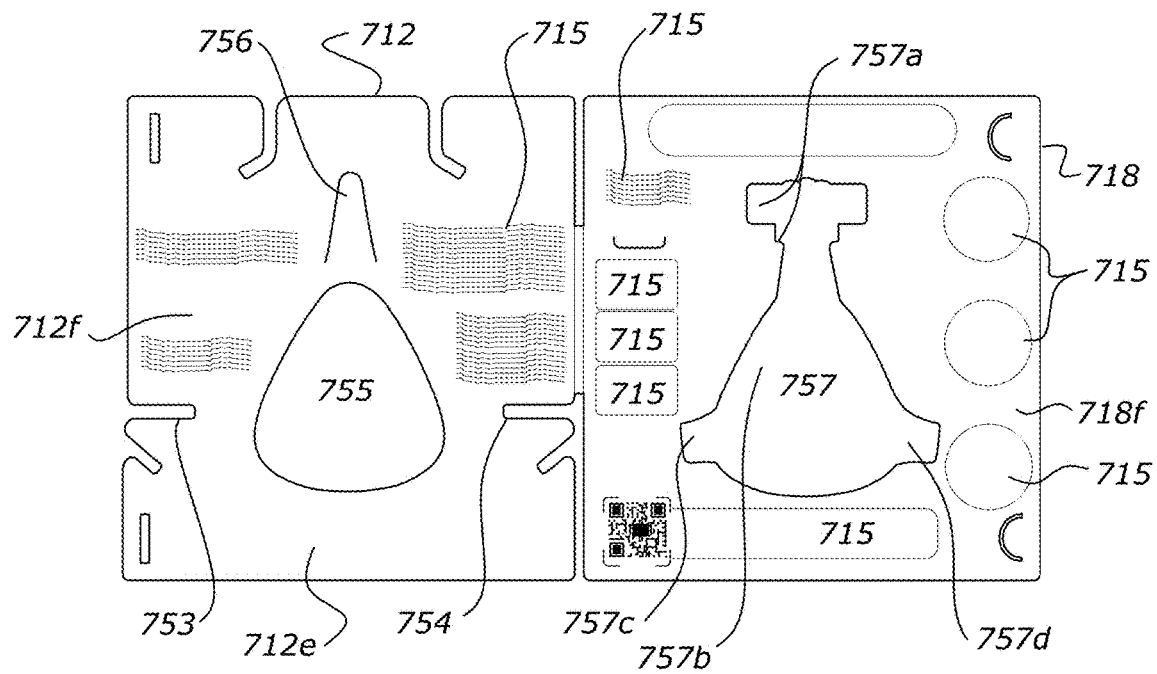
FIG. 43B shows the rear surfaces of the panels of the carton of FIG. 43A in the open position.

As shown in FIGS. 43A, 43B, the carton 700 may comprise a rear panel which is a main panel referred hereinafter as a central panel 712. As it can be seen from FIGS. 43A and 43B, the central panel 712 as referred herein is not located at the centre of the carton 700. The panel 712 is referred to as the central panel 712 because it is the primary/main panel for mask retention. As shown in FIGS. 43A, 43B, the central panel has a respiratory mask retaining feature (described later) that is configured to retain the respiratory mask 705 to the central panel 712. The carton 700 may comprise at least one flap which is a front panel 718 extending from an edge (third side 712*c*) of the central panel 712. The flap which is a the front panel 718 may be configured to be folded towards the central panel 712 and over at least a portion of the respiratory mask in a closed configuration. Similarly, the flap/front panel 718 may be configured to be folded away from the central panel 712 in an open configuration. The respiratory mask retaining feature may be configured to retain the respiratory mask to the central panel 712 when the flap 718 is in either an open position or a closed position.

The carton 700 may be formed of a sheet material, preferably a cardboard or a punched sheet of cardboard.

The carton 700 of the present embodiment folds to form only one compartment, i.e. compartment 710 (shown in FIG. 44D) that is adapted to contain parts of the respiratory mask 705 such as parts of headgear assembly or headgear 707. The flap/front panel 514 and consequently the compartment 710 is configured to be opened first to reveal the headgear 707 of the respiratory mask 705 and present information 715 in sequential order or stages. The sequential order may be predetermined by the manufacturer/supplier of the respiratory mask 705. The compartment 710 is configured to be accessible from at least one side of the central panel 712.

The carton 700 is formed of a sheet material that is configured to form a single compartment 710 for use in packaging an item such as respiratory mask 705. As shown in FIGS. 43A, 43B, the central panel 712 has at least a first side 712*a*, a second side (top side) 712*b*, a third side 712*c* and a fourth side (bottom side) 712*d*. The central panel 512 also has a front surface 712*e* and a rear surface 712*f*. As shown in FIG. 43A, the first side 712*a* is a first edge, the second side 712*b* is the second edge, the third side 712*c* is the third edge and the fourth side 712*d* is the fourth edge of the central panel 712.

The front panel 718 also has at least a first side 718*a*, a second side (top side) 718*b*, a third side 718*c* and a fourth side (bottom side) 718*d*. The central panel 512 also has a front surface 712*e* and a rear surface 712*f*. As shown in FIG. 43A, the first side 718*a* is a first edge, the second side 718*b* is the second edge, the third side 718*c* is the third edge and the fourth side 718*d* is the fourth edge of the central panel 712.

The front panel 718 is hinged and extends from the third side 712*c* of the central panel 712 via a spacer 713 as discussed later.

When the carton 700 is in a closed configuration as shown in FIG. 40D, the front panel 718 may be configured to be folded over the front surface 712*e* of the central panel 719 or in a first direction so that the front surface 712*e* of the central panel 712 and the rear surface 718*f* of the front panel 718 face each other. As shown, the overall size of the panels 712, 718 are the same or substantially the same and each of the panels 712, 718 may be generally rectangular or square in shape preferably with rounded corners. Rounded corners help to prevent curling. Also, since the corners are rounded and not sharp corners, that can help prevent puncturing or damaging of a bag (e.g. a plastic bag) when the carton 700 is inserted or packaged inside such a bag.

As shown, a spacer 713 may be located between the central panel 712 and the front panel 518, specifically between the third side 712*c* of the central panel 712 and first side 718*a* of the front panel 718. The spacer 713 may be of a rectangular or substantially a rectangular shape and the central panel 712 and the first panel 718 are connected to each other by the spacer 713. The height of the spacer 713 may be less than the height of the central panel 712 and the front panel 718. The height of each of the panels 712, 718 may be approximately 235 mm. Fold lines 717*a*, 717*b* are vertically formed on two opposite sides of the spacer 713. The spacer 713 allows spacing between the between the central panel 712 and the front panel 718. Such spacing between the panels 712, 714 make the packaging protrude to give a packaging a more appealing profile, i.e. a box shape profile. The fold lines 717*a*, 717*b* may allow the panels 712 and 718 to be hinged.

The compartment 710 may be configured to be partially enclosed. For example, the compartment 710 may be configured to be open at least at one edge/side such as a bottom edge/side.

The central panel 712 may comprise at least one and preferably two front panel retention features and the front panel 712 comprises at least one and preferably two complementary features that are adapted to engage with the front panel retention feature thereby allowing the front panel 718 and the central panel 712 to be fastened together.

As shown in FIG. 43A, the front panel retention features can be in the form of two spaced apart retention slots 721*a*, 721*b* that are adapted to be received by complementary features in the form of two spaced apart retention tabs 722*a*, 722*b*. Retention tab 722*a* is configured to be received by retention slot 721*a* and retention tab 722*b* is configured to be received by retention slot 721*b*. The retention slots 721*a*, 721*b* may be located on the central panel 712 proximal to the first side 712*a* of the central panel. The retention slot 721*a* may be located near the corner of the first side 712*a* and the second side 712*b* of the central panel 712 and the retention slot 721b may be located near the corner of the first side 712a and the fourth side 712c of the central panel 712. Retention tabs 722a and 722b may be located on the front panel 718 proximal to the third side 718c of the front panel 718. The retention slot 721a may be located at the same height as the retention tab 722a and the retention slot 721b may be located at the same height as the retention tab 722b. The retention tabs 722a, 722b are shown as semi-circular tabs to secure the front panel 718 to the rear panel which is the central panel 712. However, tabs may be of any suitable shape and size. Similarly, it may be possible that the retentions slots 721a, 721b are located on the front panel 718 and the retention tabs 722a, 722b are located on the central panel 712.

The central panel 712 may include a respiratory mask retaining feature that is configured to retain an item or an assembly of an item. The respiratory mask retaining feature may comprise a plurality of features or geometries that are configured to work together to retain respiratory mask 705 to the carton 700.

As shown in FIG. 43A, the central panel 712 may comprise the respiratory mask retaining feature in the form of a plurality of cut-outs that are slots, namely upper slots 751, 752 and lower slots 753 and 754 may be configured to receive and optionally frictionally retain straps of respiratory mask 705 or more preferably, straps of a headgear 707 of respiratory mask 705. The respiratory mask retaining feature may also comprise an opening in the form of an aperture/cut-out 755 located at the central panel 712 for securing mask seal and cushion. Further, a headgear retention tab 756 which is also a respiratory mask retention feature is presented at the central panel 712 for securing the positioning of the rear panel of the headgear 707.

The upper slots 751, 752 are spaced apart from each other. The upper slot 751 is proximal to the first side 712a of the central panel but is spaced at a distance from the first side 712c of the central panel 712. The upper slot 751 first extends vertically in a downward direction (i.e towards the direction of the centre of the panel) from the second side 712b of the central panel 712 and then extends towards the direction of the third side 712c of the central panel 712 at an angle. Similarly, upper slot 752 is proximal to the third side 712c of the central panel but is spaced at a distance from the third side 71c of the central panel 712. The upper slot 752 first extends vertically in a downward direction (i.e towards the direction of the centre of the panel) from the second side 712b of the central panel 712 and then extends towards the direction of the first side 712c of the central panel 712 at an angle. The size of both the upper slots 751 and 752 are same or substantially the same. The distance between the upper slot 751 and first side 712a of the central panel 712 may be same as the distance between the upper slot 752 and the third side 712c of the central panel 712

Figure 44A:
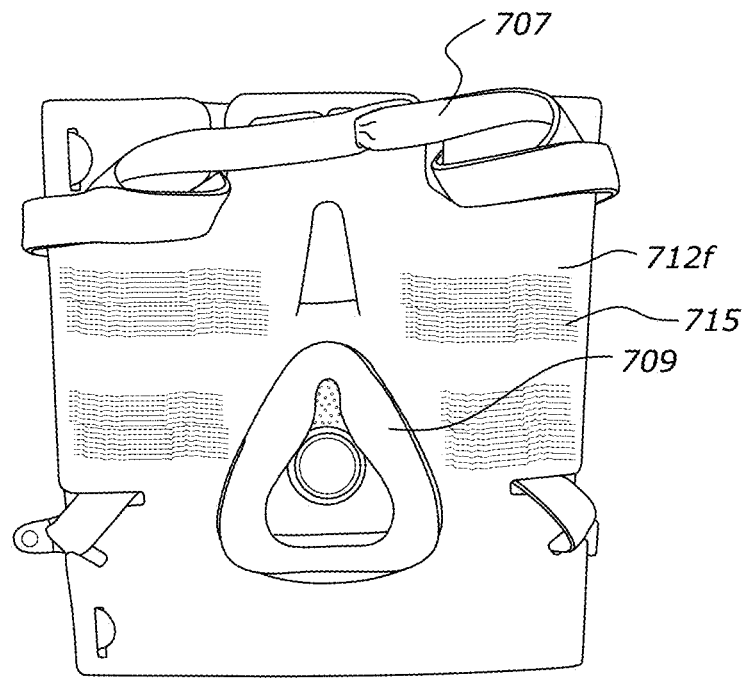
FIG. 44A shows a rear view of the carton of FIG. 43A in a closed configuration with the respiratory mask retained by the carton.
Figure 44B:
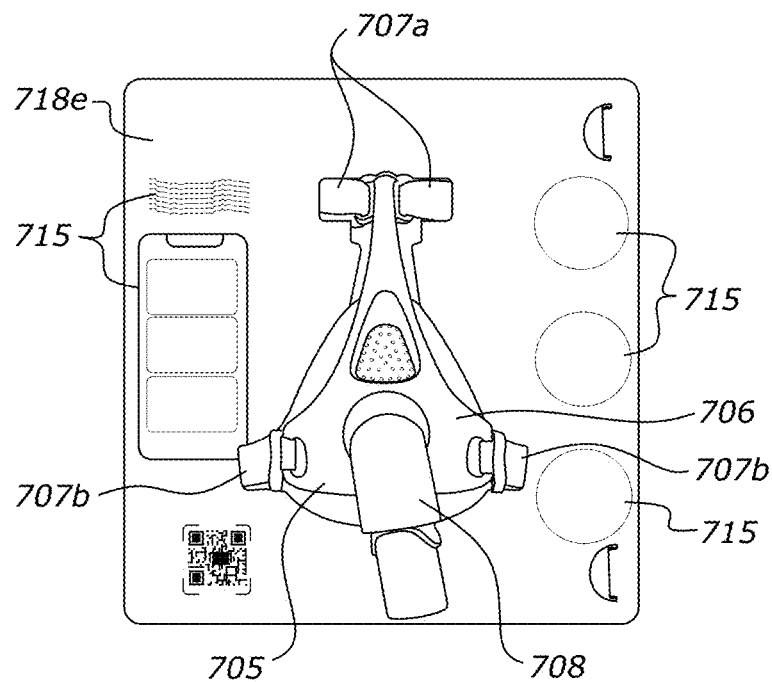
FIG. 44B shows a rear view of the carton of FIG. 43A in a closed configuration with the respiratory mask retained by the carton.
Figure 44C:
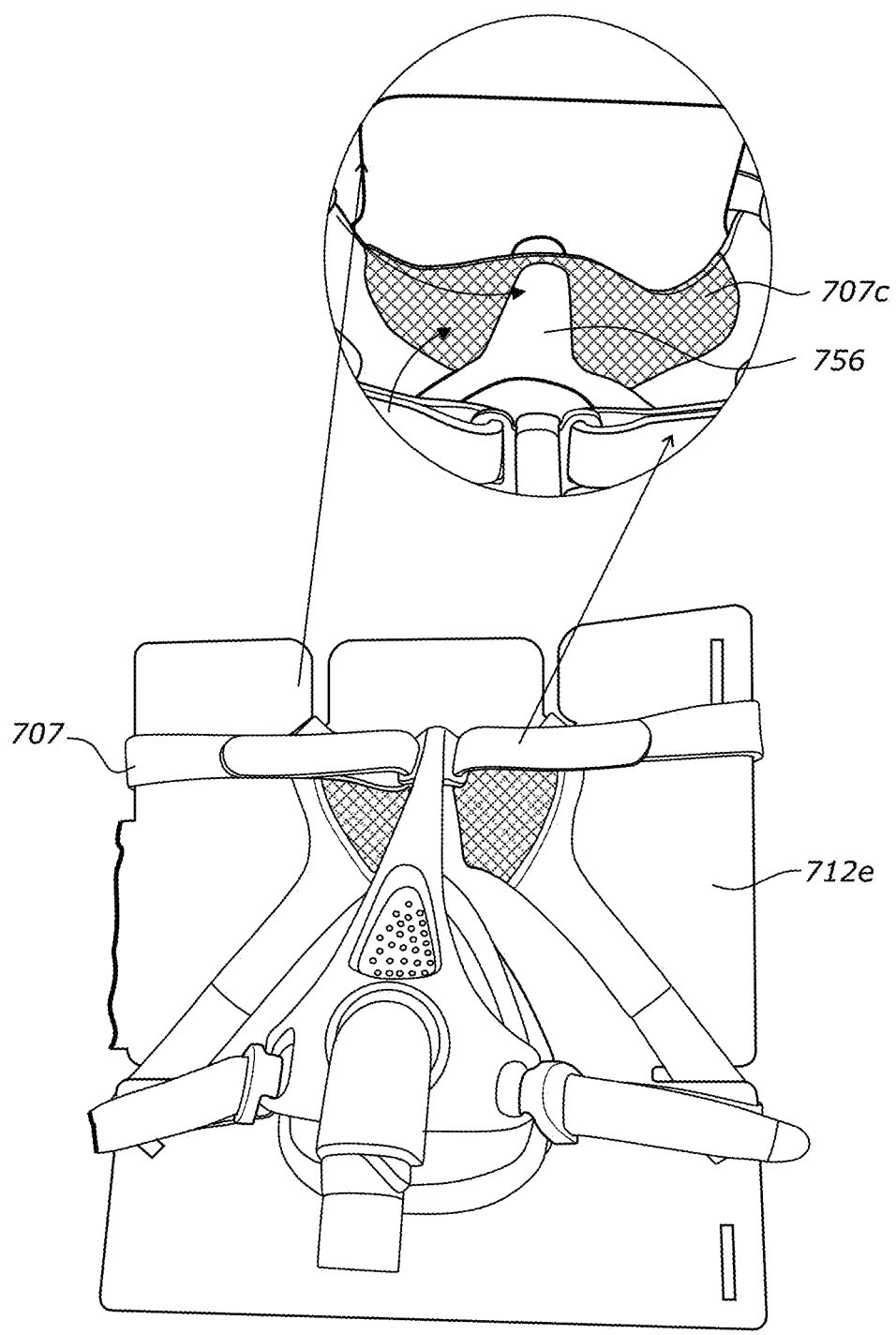
FIG. 44C shows how a head gear retention tab can be used to secure the positioning of the rear panel of the headgear of respiratory mask when the respiratory mask is retained by the carton of FIG. 43A.

The head gear retention tab 756 is located between the cut out 755 and the upper slots 751, 752 and is formed as a tongue extending from the central panel 712 at a location that is between the two upper slots 751, 752. The headgear retention tab 756 is generally triangular or trapezoidal in shape and has a rounded top portion. FIG. 44C shows how the head gear retention tab 756 can be used to secure the positioning of the rear panel 707c of the headgear 707 of respiratory mask 705 when the respiratory mask 705 is retained by the carton 700.

A first opening or aperture hereinafter referred to as a first cut-out 755 is located below the head gear retention tab 756 and is generally triangular or trapezoidal but with rounded corners. The cut-out 755 can be shaped as a Reuleaux triangle. In fact, the shape of the cut-out 755 can be any suitable shape as long as it is suitable for securing mask as shown in FIG. 44A. The cut-out 755 is located at or near the centre portion of the central panel 712 and is spaced at a distance from all sides of the central panel 712. A cut-out 755 may be sized and shaped in such a way that at least a portion of the cushion module 709 may protrude out of the cut-out 755 when the mask 705 is packaged by the carton 700 as shown in FIG. 44A.

The lower slots 753, 754 are also spaced apart from each other. The lower slot 753 comprises two portions, the first portion 753a and the second portion 753b. The first portion 753a extends horizontally from the first side 712a of the central panel 712 towards the direction of the third side 712c of the central panel 712 but terminates at a distance from the cut-out 755. The second portion 753b is located below the first portion 753a and is spaced apart from the first portion 753a. The second portion 753b extends from the first side 712a of the central panel 712 and is angled away from the first portion 753a. The angle between the first side 712a of the central panel 712 and the second portion 753b may be less than 75 degrees, preferably about 60 degrees. The portion of the sides located between the first portion 753a and second portion 753b is preferably rounded to avoid sharp corners. Preferably, the first portion 753a is longer than the second portion 753b. Similarly, the lower slot 754 also comprises two portions, the first portion 754a and the second portion 754b. The first portion 754a extends horizontally from the third side 712c of the central panel 712 towards the direction of the first side 712a of the central panel 712 but terminates at a distance from the cut-out 755. The second portion 754b is located below the first portion 754a and is spaced apart from the first portion 754a. The second portion 754b extends from the third side 712c of the central panel 712 and is angled away from the first portion 754a. The angle between the third side 712c of the central panel 712 and the second portion 754b may be less than 75 degrees, preferably about 60 degrees. The portion of the sides located between the first portion 754a and second portion 754b is preferably rounded to avoid sharp corners. Preferably, the first portion 753a is longer than the second portion 753b.

Figure 44D:
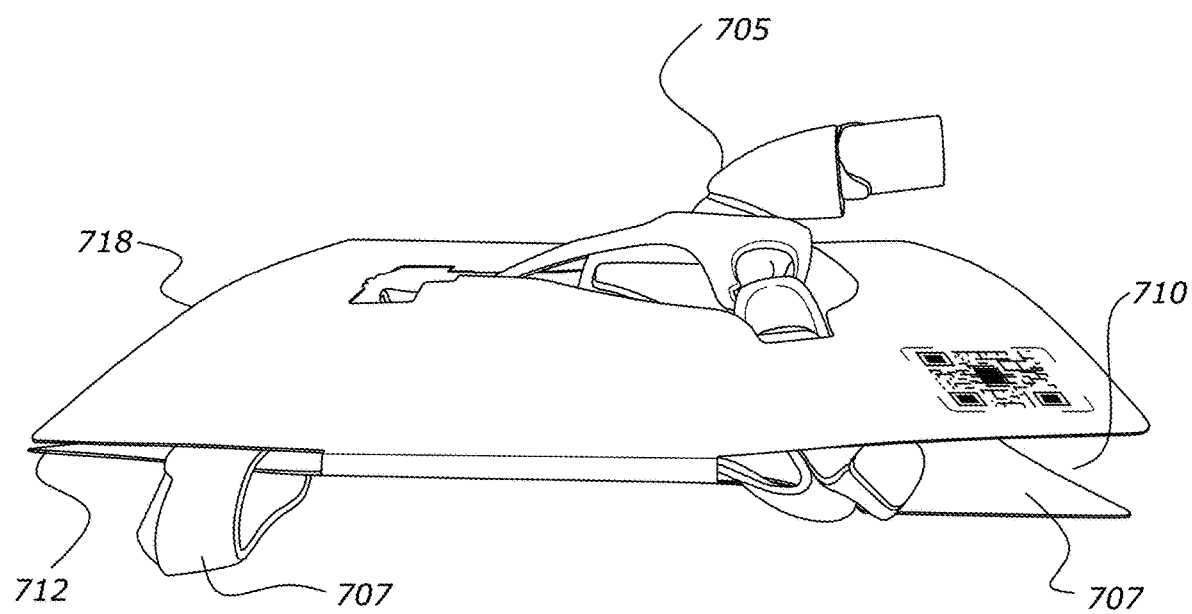
FIG. 44D shows a side view of the carton of FIG. 43A in a closed configuration with the respiratory mask retained by the carton.

The front panel 718 also comprises an opening in the form of a second aperture 757/a second cut-out 757 for further securing the respiratory mask 705. The cut-out 757 can be of any suitable shape and size that allows a portion of the patient interface or mask frame and inlet conduit or elbow to protrude out through the second cut-out 757 when the carton 700 is in closed position with at least the headgear of the mask secured to the central panel 712. This is shown in FIGS. 44B and 44D. The second cut-out 757 is located at or near the centre portion of the front panel 718 and is spaced at a distance from all sides of the front panel 718. As shown, the second cut-out 757 may comprise a T-shaped or substantially T-shaped portion 757a proximal to the second side 718b of the front panel 718 through which portions of the upper straps 707a of the headgear 707 of the mask 705 can protrude out as shown in FIGS. 44B and 44D. The central portion 757b is shaped as a frame of the mask 705 and so that the frame 706 of the mask 705 can protrude out of the central portion 705 as shown in FIGS. 44B and 44D. Upper and lower strap slots 757c and 757d are formed on the two lateral sides of the central portion 757b to allow lower straps 707b of the headgear 707 of the mask 705 to protrude out as shown in FIGS. 44B and 44D. The lower strap slots 757c, 757d are angled to better retain the lower straps 707b in an assembled state with the frame 706 of the mask 705.

The positioning and shape of any retention features above may be varied to suit any respiratory masks that require packaging.

From the above, it can be appreciated that no adhesives or permanent fasteners may be required for the carton 700 to remain in a closed configuration as shown in Figures. In alternative embodiments, it may be desirable to seal the carton, such as with adhesive or mechanical fasteners (for example, pins, clips, or staples).

Each of the central panel 712 and the front panel 718 may provide space for printing information or instructions for the user. The instructions 715 can be any instructions such as but not limited to first set-up instructions, fitting instructions, mask parts information, cleaning instructions, mask parts replacement instructions, and additional support information. The information may also be manufacturing, traceability and legal information. It may also contain a machine-readable code e.g. a Quick Response code (QR code) that can be scanned by a suitable device such as a smartphone camera to translate to useful information such as displaying a text to the user, opening a URL etc.

In summary, insert or carton 700 may include two foldable panels 712, 718, each having a front surface 712e, 518e and a rear surface 712f, 718f, therefore a total of four surfaces. The central panel 712 may retain the mask 705 and can be folded over with an adjacent panel, i.e. front panel 718 to form a compartment 710 that may be adapted to contain the at least a portion of the headgear 707 of the mask 705. At least one or each of the four surfaces may contain printed information 715 or instructions for the user. The retention tabs 722a, 722b may be configured to be opened/released from the retention slots 721a, 721b to reveal the inner surfaces and present information in stages. The retention tabs 722a, 722b may prevent the carton 700 from unfolding and may maintain the compartment 710 for the portion of the straps 707a, 707b of the headgear 707 to be retained. The item retaining feature is a respiratory mask retaining feature and may comprise a plurality of slots 751, 752, 753, 754 that can receive and frictionally retain the straps of the headgear 707. The compartment 710 is formed by the front panel 718 folding in a direction towards the central panel 712, and by inserting the retention tabs 722a, 722b located at the front panel 718 into the retention slots 721a, 721b located at the central panel 712. The mask 707 is secured onto the central panel 712, attached by feeding the headgear straps 707a, 707b behind the central panel 712 into the compartment 710 through the slots 751, 752, 753, 754 located at the central panel 710. The mask 507 is also secured by the cut out 755 formed on central panel 712 and cushion module and seal of the mask 105 partially protrude out from the cut-out 755 as shown in FIG. 44A. Similarly, the cut-out 757 formed at the front panel 718 allows the further securing the respiratory mask 705 and also allows a portion of the patient interface/frame 706 and elbow 708 of the mask 705 to protrude out through the cut-out when the carton 700 is in closed position in which the front panel 718 of the carton is folded towards a front surface of the central panel that retains the mask. The shape and positioning of the slots 751, 752, 753, 754 and cut-outs 755, 757 can be varied to suit any respiratory mask that requires packaging.

The packaging carton 700 as described in the seventh preferred embodiment includes several advantages. The surface area of the cardboard to make the carton 700 can be reduced as the carton 700 only contains a single compartment. The carton 700 is easy to assemble and disassemble. The structure is less susceptible to damage which means that thinner cardboard may be used, and such thinner carton may still be sufficient to maintain packaging structure. The design is simple and provides sufficient space at the surface of the panels 712, 718 for presenting information to the user thereby minimising the need of extra components such as a quick reference guide. The information may be presented in a sequential order. Since, the headgear 707 can be attached to the mask assembly but is hidden until the mask 705 is removed from the carton 700, that can help prevent any confusion and tangling or disassembly.

The carton 700 may be configured to be placed in a bag as an insert. Although, any suitable bag may be used such as the bag 10' as described above.

While the foregoing description of the preferred embodiments are directed to packaging or respiratory mask, the packaging system or carton may equally be suitable for packaging of many other item or item assemblies, although retention of the respiratory mask is most preferred and is what the packaging is mainly intended to be used for.

It will of course be realised that while the foregoing has been given by way of illustrative example of the present invention, all such modifications and variations thereto as would be apparent to a person skilled in the art are deemed to fall within the broad scope and ambit of the various aspects if invention as is hereinbefore described and/or defined in the claims.

The invention claimed is:

1. A packaging carton for a respiratory mask, the packaging carton comprising:
   a central panel having at least one respiratory mask retaining feature configured to retain the respiratory mask to the central panel,
   at least one flap extending from an edge of the central panel, and
   at least one retention tab that is configured to be received by at least one retention slot,
   wherein the at least one flap is configured to be folded towards the central panel and over at least a portion of the respiratory mask in a closed configuration, and to be folded away from the central panel in an open configuration, and the at least one respiratory mask retaining feature is configured to retain the respiratory mask to the central panel when the at least one flap is in either the open configuration or the closed configuration,
   wherein the at least one respiratory mask retaining feature comprises a plurality of T-shaped cutouts configured to receive and frictionally retain straps of the respiratory mask or straps of a headgear of the respiratory mask,
   wherein each of the plurality of T-shaped cutouts extend from an outer edge of the central panel, and
   wherein at least one of the plurality of T-shaped cutouts is located along a periphery of the packaging carton in an unfolded condition.

2. The packaging carton of claim 1, wherein in the closed configuration, the packaging carton is adapted to form a first compartment configured to receive a first portion of the respiratory mask, and a second compartment configured to receive a second portion of the respiratory mask.

3. The packaging carton of claim 2, wherein the first compartment is configured to at least partially enclose the respiratory mask, and the second compartment is configured to retain a user instruction booklet.

4. The packaging carton of claim 1, wherein the at least one flap is foldable over the central panel.

5. The packaging carton of claim 2, wherein the first compartment is formed by the central panel, a pair of opposing side flaps and a top flap extending from the central panel.

6. The packaging carton of claim 5, wherein the pair of opposing side flaps, and the top flap are foldable over the central panel.

7. The packaging carton of claim 2, wherein the second compartment is formed by at least the central panel and a rear panel.

8. The packaging carton of claim 2, wherein the second compartment comprises open sides.

9. The packaging carton of claim 2, wherein the second compartment includes rear side flaps configured to fold such that the second compartment is enclosed at the sides.

10. The packaging carton of claim 1, wherein the packaging carton is formed from a single sheet of material.

11. The packaging carton of claim 1, wherein the packaging carton is made from a cardboard and/or a punched sheet(s) of a cardboard and/or a plastic material.

12. The packaging carton of claim 2, wherein the first and second compartments are formed without adhesives or permanent fasteners.

13. The packaging carton of claim 1, wherein in the closed configuration, the packaging carton is adapted to form a single compartment that is configured to receive at least a portion of the respiratory mask.

14. The packaging carton of claim 13, wherein the portion of the respiratory mask includes at least a portion of a headgear.

15. The packaging carton of claim 1, wherein the central panel and the at least one flap have surfaces provided with printed information.

16. The packaging carton of claim 13, wherein the single compartment is formed by at least the central panel and the at least one flap.

17. The packaging carton of claim 1, wherein the at least one flap comprises at least two panels, the at least two panels being an intermediate panel and a rear panel, the intermediate panel being located between the central panel and the rear panel and is foldable towards the central panel and the rear panel.

18. The packaging carton of claim 1, wherein the packaging carton is configured to be placed in a bag.

19. The packaging carton of claim 18, wherein the bag is made from a recyclable, biodegradable and/or compostable material.

20. A respiratory mask packaging carton that is formed of a single sheet material configured to form at least one compartment for use in packaging a respiratory mask, the respiratory mask packaging carton comprising:
a main panel that is connected to at least one flap that is configured to be folded over the main panel to form the at least one compartment, the main panel comprising at least one respiratory mask retaining feature that is configured to retain the respiratory mask to the main panel, and
a retention tab and a retention slot, wherein the retention tab is configured to be opened or released from the retention slot,
wherein the at least one respiratory mask retaining feature comprises a plurality of T-shaped cutout features, wherein each of the plurality of T-shaped cutout features extend from an outer edge of the main panel, and wherein at least one of the plurality of T-shaped cutout features is located along a periphery of the respiratory mask packaging carton in an unfolded condition.

21. The respiratory mask packaging carton of claim 20, wherein the respiratory mask packaging carton comprises at least three foldable panels including the main panel, each of the at least three foldable panels having a front surface and a rear surface.

22. The respiratory mask packaging carton of claim 21, wherein when the retention tab is opened or released from the retention slot, inner surfaces of the at least three foldable panels are revealed to present printed information in stages.

23. The respiratory mask packaging carton of claim 22, wherein the at least one compartment is formed by the main panel folding in a direction towards an intermediate panel that is located adjacent the main panel and between the main panel and a rear panel, and by inserting the retention tab that is connected to the main panel into the retention slot located at or near a fold line formed between the intermediate panel and the rear panel.

24. The respiratory mask packaging carton of claim 20, wherein the main panel and the at least one flap each have a front surface and a rear surface.

25. The respiratory mask packaging carton of claim 24, wherein the packaging carton comprises at least two retention tabs and at least two retention slots, wherein the at least two retention tabs are configured to be opened or released from the at least two retention slots to reveal inner surfaces of the panels to present printed information in stages.

26. The respiratory mask packaging carton of claim 25, wherein the at least one compartment is formed by folding a front panel that is located adjacent the main panel in a direction towards the main panel, and by inserting the at least two retention tabs that are located at the front panel into the at least two retention slots located at the main panel.

27. The packaging carton of claim 1, wherein the plurality of T-shaped cutouts are vertically arranged and parallel to a longitudinal axis of the central panel.

28. The packaging carton of claim 1, wherein at least one of the plurality of T-shaped cutouts are positioned in an upper portion and at least one of the plurality of T-shaped cutouts are positioned in a lower portion of the central panel, and wherein the at least one of the plurality of T-shaped cutouts in the upper portion are smaller than the at least one of the plurality of T-shaped cutouts in the lower portion.

* * * * *